United States Patent [19]
Fujiwara et al.

[11] Patent Number: 5,658,917
[45] Date of Patent: Aug. 19, 1997

[54] ISOQUINOLINES HAVING ADENOSINE UPTAKE INHIBITOR ACTIVITY

[75] Inventors: Shigeki Fujiwara; Daisuke Machii; Haruki Takai; Hiromi Nonaka, all of Sunto-gun; Hiroshi Kase, Koganei; Kozo Yao, Sunto-gun; Michiyo Kawakage, Inazawa, all of Japan; Hideaki Kusaka, Pittsburgh, Pa.; Akira Karasawa, Sunto-gun, Japan

[73] Assignee: Kyowa Hakko Kogyo Co., Ltd., Tokyo, Japan

[21] Appl. No.: 430,234

[22] Filed: Apr. 28, 1995

Related U.S. Application Data

[62] Division of Ser. No. 318,876, Oct. 17, 1994, Pat. No. 5,624,926.

[30] Foreign Application Priority Data

Feb. 18, 1993 [JP] Japan ................................ 5-028830

[51] Int. Cl.$^6$ .................... C07D 401/14; A61K 31/445; A61K 31/505; A61K 31/50
[52] U.S. Cl. .................... 514/259; 514/248; 514/267; 514/245; 544/284; 544/237; 544/250; 544/212; 544/234; 544/233; 544/247; 544/245
[58] Field of Search .......................... 544/284; 514/259

[56] References Cited

U.S. PATENT DOCUMENTS

| | | | |
|---|---|---|---|
| 4,166,117 | 8/1979 | Vincent et al. | 424/251 |
| 4,668,683 | 5/1987 | Takai et al. | 514/259 |
| 4,680,296 | 7/1987 | Manoury et al. | 514/259 |
| 5,504,088 | 4/1996 | Sugimoto et al. | 514/259 |

FOREIGN PATENT DOCUMENTS

| | | |
|---|---|---|
| 0009465 | 4/1980 | European Pat. Off. . |
| 076082 | 4/1984 | Japan . |
| 167277 | 6/1990 | Japan . |

OTHER PUBLICATIONS

Nomoto, Y. et al., Chem. Pharm. Bull., vol. 38, No. 6 (1990) 1591–95. Month of publication not provided.

Young, M.A. et al. Am. J. Physiol., 261, H1570–H1577 (1991). Month of publication not provided.

Dorion, M. et al. J. Cardiovasc. Pharmacol. 19, 69–77 (1992). Month of publication not provided.

Remington's Pharm. Sci., (Phila. Coll. Pharm., Phila. (1992) 1286–1292. Month of publication not provided.

Primary Examiner—Mukund J. Shah
Assistant Examiner—King Lit Wong
Attorney, Agent, or Firm—Fitzpatrick, Cella, Harper & Scinto

[57] ABSTRACT

The present invention relates to an adenosine uptake inhibitor and an agent for the myocardium protection or the prevention or treatment of inflammatory edema, comprising a 1,2,3,4-tetrahydro-2,4-dioxoquinazoline derivative represented by formula (I):

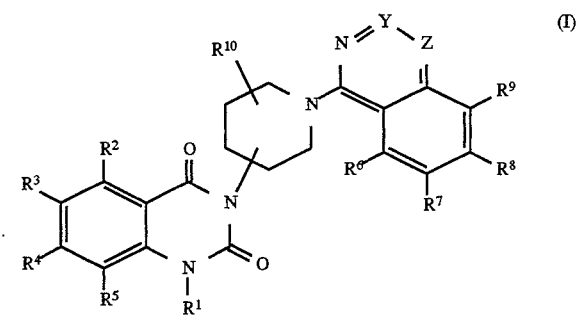

wherein $R^1$ represents hydrogen, substituted or unsubstituted lower alkyl, alkenyl, or substituted or unsubstituted aralkyl; $R^2$, $R^3$, $R^4$, and $R^5$ independently represent hydrogen, halogen, amino, mono- or di(lower alkyl)amino, lower alkanoylamino, nitro, cyano, substituted or unsubstituted lower alkyl, hydroxy, lower alkoxy, lower alkylthio, carboxy, lower alkoxycarbonyl, lower alkanoyl, aralkyloxy, or lower alkanoyloxy; $R^6$, $R^7$, $R^8$, and $R^9$ independently represent hydrogen, hydroxy, substituted or unsubstituted lower alkoxy, or aralkyloxy, or any adjoining two of them are combined to form methylenedioxy; $R^{10}$ represents hydrogen or lower alkyl; and Y and Z independently represent N or C—$R^{11}$ (wherein $R^{11}$ represents hydrogen, substituted or unsubstituted lower alkyl, or halogen), or a pharmaceutically acceptable salt thereof as an active ingredient.

8 Claims, No Drawings

ISOQUINOLINES HAVING ADENOSINE UPTAKE INHIBITOR ACTIVITY

This application is a division of application Ser. No. 08/318,876, filed Oct. 17, 1994, now U.S. Pat. No. 5,624,926.

TECHNICAL FIELD

The present invention relates to a drug containing a 1,2,3,4-tetrahydro-2,4-dioxoquinazoline derivative or a pharmaceutically acceptable salt thereof as an active ingredient, which inhibits nucleoside uptake of the cells to increase an extracellular adenosine concentration and is therefore useful for the protection of myocardium against myocardosis due to anoxemia or hypoxia, such as ischemia and reperfusion disorders, and for the prevention or treatment of inflammation, such as leg and foot edema.

BACKGROUND ART

With respect to 1,2,3,4-tetrahydro-2,4-dioxoquinazoline derivatives having a 1-(6,7-dimethoxy-4-quinazolinyl)-4-piperidinyl group at the 3-position, those having a hydrogen atom, a chlorine atom or a nitro group at the 6-position are described in Chem. Pharm. Bull., 38, 1591–1595 (1990). Further, it is known that a compound having adenosine uptake inhibitory activity exhibits myocardium protecting activity [Circul., 80, 1400–1411 (1989); Am. J. Physiol., H1570–1577 (1991); J. Cardiovasc. Pharmacol., 20, 173–178 (1992)].

DISCLOSURE OF THE INVENTION

The present invention relates to an adenosine uptake inhibitor and an agent for the myocardium protection or the prevention or treatment of inflammatory edema which contain as an active ingredient a 1,2,3,4-tetrahydro-2,4-dioxoquinazoline derivative represented by formula (I):

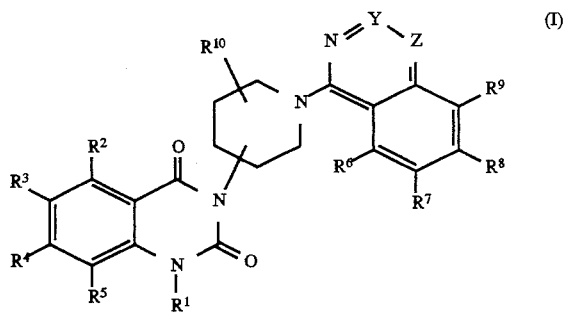

wherein $R^1$ represents hydrogen, substituted or unsubstituted lower alkyl, alkenyl, or substituted or unsubstituted aralkyl; $R^2$, $R^3$, $R^4$, and $R^5$ independently represent hydrogen, halogen, amino, mono- or di(lower alkyl)amino, lower alkanoylamino, nitro, cyano, substituted or unsubstituted lower alkyl, hydroxy, lower alkoxy, lower alkylthio, carboxy, lower alkoxycarbonyl, lower alkanoyl, aralkyloxy, or lower alkanoyloxy; $R^6$, $R^7$, $R^8$, and $R^9$ independently represent hydrogen, hydroxy, substituted or unsubstituted lower alkoxy, or aralkyloxy, or any adjoining two of them are combined to form methylenedioxy; $R^{10}$ represents hydrogen or lower alkyl; and Y and Z independently represent N or C—$R^{11}$ (wherein $R^{11}$ represents hydrogen, substituted or unsubstituted lower alkyl, or halogen), or a pharmaceutically acceptable salt thereof.

The present invention also relates to a method for protecting myocardium or preventing or treating inflammatory edema and a method for preventing or treating diseases caused by adenosine uptake, which comprise administering an effective amount of a 1,2,3,4-tetrahydro-2,4-dioxoquinazoline derivative represented by formula (I) or a pharmaceutically acceptable salt thereof.

The present invention further relates to the use of a 1,2,3,4-tetrahydro-2,4-dioxoquinazoline derivative represented by formula (I) or a pharmaceutically acceptable salt thereof for the preparation of a pharmaceutical composition which is useful for the protection of myocardium, the prevention or treatment of inflammatory edema, and the prevention or treatment of diseases caused by adenosine uptake.

Furthermore, the present invention relates to the use of a 1,2,3,4-tetrahydro-2,4-dioxoquinazoline derivative represented by formula (I) or a pharmaceutically acceptable salt thereof for the protection of myocardium, the prevention or treatment of inflammatory edema, and the prevention or treatment of diseases caused by adenosine uptake.

The present invention also provides a 1,2,3,4-tetrahydro-2,4-dioxoquinazoline derivative represented by formula (I-a):

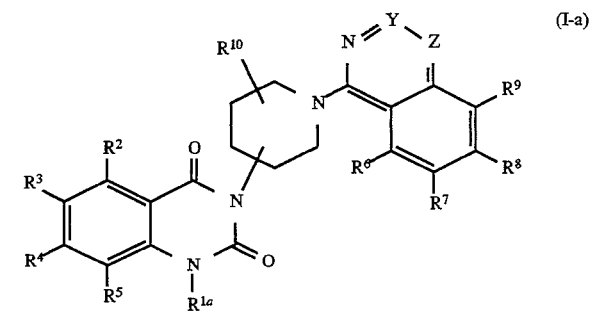

wherein $R^{1a}$ represents substituted or unsubstituted lower alkyl, alkenyl, or substituted or unsubstituted aralkyl; and $R^2$, $R^3$, $R^4$, $R^5$, $R^6$, $R^7$, $R^8$, $R^9$, $R^{10}$, Y, and Z have the same meanings as defined above, and a pharmaceutically acceptable salt thereof.

The compounds represented by formula (I) and the compounds represented by formula (I-a) are hereinafter referred to as Compounds (I) and Compounds (I-a), respectively. The same applies to the compounds of other formula numbers.

In the definitions of the groups in formula (I) and formula (I-a), the lower alkyl and the lower alkyl moiety of the mono- or di(lower alkyl)amino, lower alkanoylamino, lower alkoxy, lower alkylthio, lower alkoxycarbonyl, lower alkanoyl and lower alkanoyloxy mean a straight-chain or branched alkyl group having 1 to 8 carbon atoms, such as methyl, ethyl, propyl, isopropyl, butyl, isobutyl, sec-butyl, tert-butyl, pentyl, isopentyl, hexyl, heptyl, and octyl. The alkenyl means a straight-chain or branched alkenyl group having 2 to 6 carbon atoms, such as vinyl, allyl, methacryl, crotyl, 3-butenyl, 2-pentenyl, 4-pentenyl, 2-hexenyl, and 5-hexenyl. The aralkyl and the aralkyl moiety of the aralkyloxy mean an aralkyl group having 7 to 13 carbon atoms, such as benzyl, phenethyl, and benzhydryl. The halogen includes fluorine, chlorine, bromine, and iodine.

The substituted lower alkyl and the substituted lower alkoxy each has 1 to 3 independently selected substituents. Examples of the substituents are halogen, nitro, cyano, hydroxy, lower alkoxy, carboxy, lower alkoxycarbonyl, lower alkanoyl, cycloalkyl, amino, mono- or di(lower alkyl)amino, and phthalimide. The substituted aralkyl has 1 to 3 independently selected substituents on the benzene ring thereof. Examples of the substituents are halogen, lower alkyl, nitro, cyano, amino, mono- or di(lower alkyl)amino, hydroxy, lower alkoxy, carboxy, lower alkoxycarbonyl, lower alkanoyl, methylenedioxy, and trifluoromethyl.

In the definitions of the substituents, the halogen, lower alkoxy, lower alkoxycarbonyl, lower alkanoyl, mono- or di(lower alkyl)amino, and lower alkyl have the same meanings as defined above. The cycloalkyl means a cycloalkyl group having 3 to 8 carbon atoms, such as cyclopropyl, cyclobutyl, cyclopentyl, cyclohexyl, cycloheptyl, and cyclooctyl.

The pharmaceutically acceptable salts of Compounds (I) and Compounds (I-a) include pharmaceutically acceptable acid addition salts, metal salts, ammonium salts, organic amine addition salts, and amino acid addition salts.

Examples of the pharmaceutically acceptable acid addition salts of Compounds (I) and Compounds (I-a) are inorganic acid addition salts such as hydrochloride, sulfate, and phosphate, and organic acid addition salts such as acetate, maleate, fumarate, tartrate, citrate, and methanesulfonate. Examples of the pharmaceutically acceptable metal salts are alkali metal salts such as sodium salt and potassium salt, alkaline earth metal salts such as magnesium salt and calcium salt, aluminum salt, and zinc salt. Examples of the pharmaceutically acceptable ammonium salts are ammonium salt and tetramethylammonium salt. Examples of the pharmaceutically acceptable organic amine addition salts are salts with morpholine and piperidine. Examples of the pharmaceutically acceptable amino acid addition salts are salts with lysine, glycine, and phenylalanine.

The processes for producing Compounds (I) are described below.

Process 1: Process for producing Compound (I-b)
[Compound (I) in which $R^1$ is hydrogen]

Compound (I-b) can be prepared by the following reaction steps:

(In the formulae, $X^a$ represents chlorine, bromine, iodine, methanesulfonyloxy, benzenesulfonyloxy, or toluenesulfonyloxy; and $R^2$, $R^3$, $R^4$, $R^5$, $R^6$, $R^7$, $R^8$, $R^9$, $R^{10}$, Y, and Z have the same meanings as defined above.)

The starting Compound (II) can be obtained according to the method described in Chem. Pharm. Bull., 34, 1907–1916 (1986).

(Step 1)

The ethoxycarbonyl group of Compound (II) is hydrolyzed in the presence of an acid, such as sulfuric acid, hydrochloric acid, or hydrobromic acid, in an appropriate solvent, such as water, a lower alcohol, e.g., methanol, ethanol, or isopropanol, a cyclic ether, e.g., tetrahydrofuran (THF) or 1,4-dioxane, or a mixture thereof, at a temperature of room temperature to the boiling point of the solvent used for 10 minutes to 48 hours. Then, Compound (I-b) can be obtained by reaction of the hydrolysis product with Compound (III) [South African Patent No. 67 06512 (1968); Chem. Pharm. Bull., 38, 2179–2183 (1990)] in the presence of a base, such as a tertiary amine, e.g., triethylamine or pyridine, or an alkali metal carbonate, e.g., sodium carbonate or potassium carbonate, in an appropriate solvent, such as a lower alcohol, e.g., methanol, ethanol or isopropanol, a cyclic ether, e.g., THF or 1,4-dioxane, dimethylformamide (DMF), dimethyl sulfoxide (DMSO), or a mixture thereof, at a temperature of room temperature to the boiling point of the solvent used for 10 minutes to 48 hours according to the method described in Chem. Pharm. Bull., 38, 1591–1595 (1990) or Chem. Pharm. Bull., 38, 2179–2183 (1990).

Process 2: Process for producing Compound (I-a)
[Compound (I) in which $R^1$ is substituted or unsubstituted lower alkyl, alkenyl, or substituted or unsubstituted aralkyl]

Compound (I-a) can be prepared by the following reaction step.

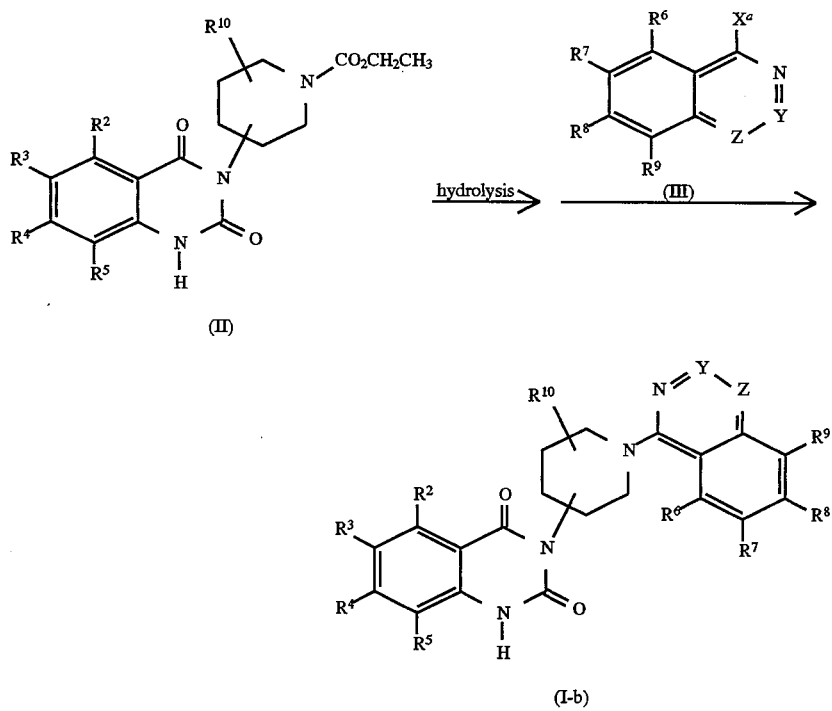

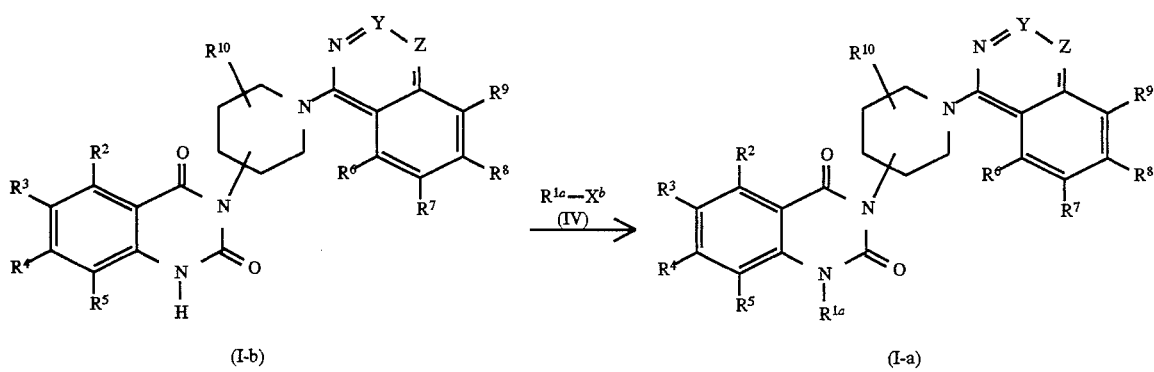

(In the formulae, $X^b$ represents chlorine, bromine, iodine, methanesulfonyloxy, benzenesulfonyloxy, or toluenesulfonyloxy; and $R^{1a}$, $R^2$, $R^3$, $R^4$, $R^5$, $R^6$, $R^7$, $R^8$, $R^9$, $R^{10}$, Y, and Z have the same meanings as defined above.)

(Step 2)

Compound (I-a) can be obtained by reaction of Compound (I-b) with 1 to 2 equivalents of Compound (IV) in the presence of 1 to 2 equivalents of a base, such as sodium hydride, potassium carbonate, or cesium carbonate, in an inert solvent, such as THF, DMF, acetone, or methyl ethyl ketone, at a temperature of 0° C. to the boiling point of the solvent used for 10 minutes to 24 hours.

Compound (I-a) can also be prepared by the following reaction steps:

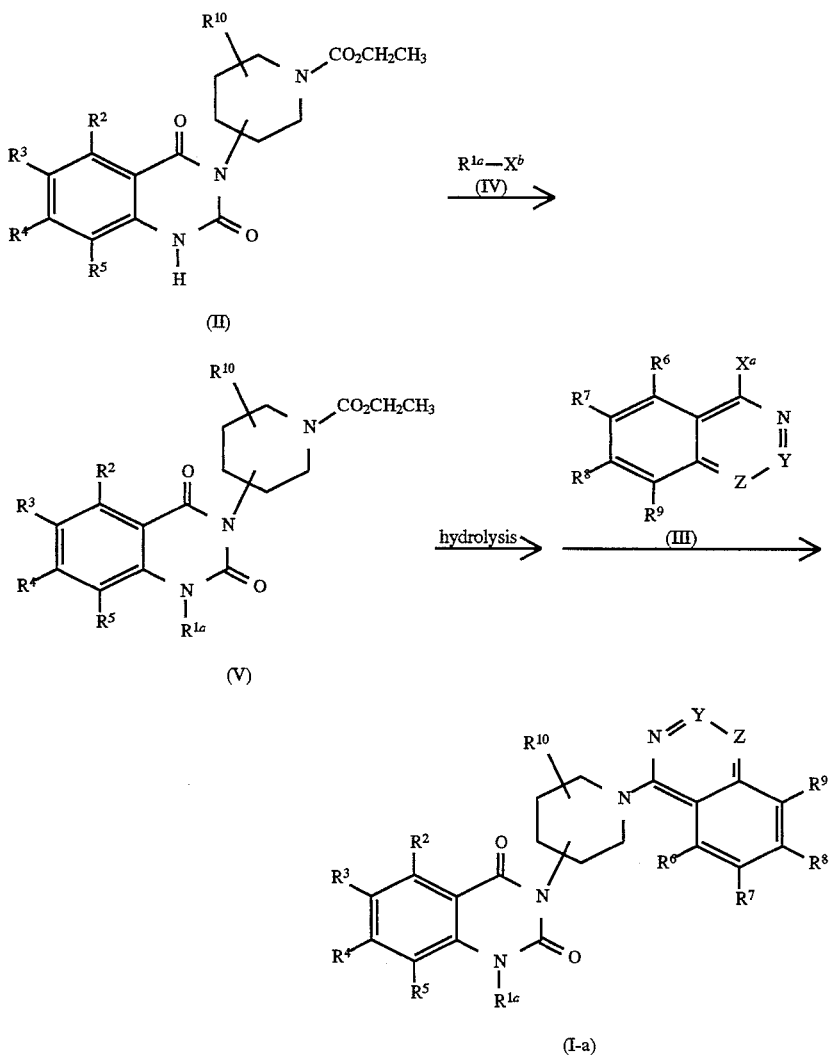

(In the formulae, $X^a$, $X^b$, $R^{1a}$, $R^2$, $R^3$, $R^4$, $R^5$, $R^6$, $R^7$, $R^8$, $R^9$, $R^{10}$, Y, and Z have the same meanings as defined above.)
(Step 3)

Compound (I-a) can be obtained by preparing Compound (V) from Compound (II) by the similar method as in Step 2 and then treating Compound (V) in the similar manner as in Step 1.

Compound (I) having at least one amino, mono- or di(lower alkyl)amino, or lower alkanoylamino group as $R^2$, $R^3$, $R^4$, or $R^5$ can also be prepared by reducing a corresponding Compound (I) having a nitro group as $R^2$, $R^3$, $R^4$, or $R^5$, and if necessary, alkylating or acylating the product. The reduction can be carried out in a conventional manner, for example, by catalytic reduction or reduction using a metal. The catalytic reduction is usually carried out in the presence of a catalyst, such as Raney nickel, palladium on carbon, or platinum oxide, in an appropriate solvent, such as methanol, ethanol, ethyl acetate, dioxane, THF, or acetic acid, at room temperature under an atmospheric pressure for 10 minutes to 48 hours. The reduction using a metal can be carried out in a zinc-acetic acid system, an iron-acetic acid system, an iron-ferric chloride-ethanol-water system, an iron-hydrochloric acid system, a tin-hydrochloric acid system, or the like, at a temperature of room temperature to the boiling point of the solvent used for 10 minutes to 48 hours. The alkylation or acylation of the reduction product is carried out by using a common alkylating agent (such as an alkyl halide, e.g., methyl iodide) or acylating agent (such as an acid anhydride, e.g., acetic anhydride, or an acid halide, e.g., acetyl chloride), if necessary in the presence of a base, such as pyridine, triethylamine, an alkyl metal hydroxide, or an alkyl metal carbonate, and/or a solvent, such as chloroform, dichloromethane, THF, or 1,4-dioxane, at a temperature of 0° C. to the boiling point of the solvent used for 10 minutes to 48 hours.

Compound (I) having at least one hydroxy-substituted alkyl group as $R^2$, $R^3$, $R^4$, or $R^5$ can also be prepared by reducing or alkylating a corresponding Compound (I) having an alkanoyl-substituted alkyl group as $R^2$, $R^3$, $R^4$, or $R^5$. The reduction can be carried out by using a reducing agent, such as lithium aluminum hydride or sodium boron hydride, in an appropriate solvent, such as methanol, ethanol, ethyl acetate, dioxane or THF, usually at a temperature of –78° C. to room temperature for 10 minutes to 48 hours. The alkylation is carried out by using a common organometallic reagent, such as a Grignard reagent, e.g., methylmagnesium bromide or ethylmagnesium chloride, or an organolithium reagent, e.g., methyl lithium or butyl lithium, in an appropriate solvent, such as dioxane, ether, or THF, usually at a temperature of –78° C. to room temperature for 10 minutes to 48 hours.

Compound (I) having at least one carboxyl group as $R^2$, $R^3$, $R^4$, or $R^5$ can also be prepared by subjecting a corresponding Compound (I) having an acetyl group as $R^2$, $R^3$, $R^4$, or $R^5$ to haloform reaction. The haloform reaction can be carried out by using a solution of sodium hypohalogenite prepared from chlorine or bromine and an aqueous solution of sodium hydroxide according to the method described in J. Am. Chem. Soc., 72, 1642 (1950) or the like.

Compound (I) having at least one hydroxyl group as $R^6$, $R^7$, $R^8$, or $R^9$ can also be prepared by subjecting a corresponding Compound (I) having a benzyloxy group as $R^6$, $R^7$, $R^8$, or $R^9$ to the above-mentioned catalytic reduction.

Compound (I) having at least one hydroxyl group as $R^2$, $R^3$, $R^4$, or $R^5$; or $R^6$, $R^7$, $R^8$, or $R^9$ can also be prepared by dealkylating a corresponding Compound (I) having a lower alkoxy group as $R^2$, $R^3$, $R^4$, or $R^5$; or $R^6$, $R^7$, $R^8$, or $R^9$. The dealkylation can be carried out in the presence of an acid, such as hydrobromic acid or hydroiodic acid, with or without a solvent, such as water, acetic acid, or a lower alcohol, e.g., methanol or ethanol; or in the presence of at least an equivalent amount of an alkali metal salt (e.g., a sodium salt or a potassium salt) of a thiol compound, e.g., ethanethiol or thiophenol, in a solvent, such as DMF or DMSO; or in the presence of a Lewis acid, such as boron trichloride, boron tribromide, or aluminum trichloride, in a solvent, such as dichloromethane. The reaction is carried out at a temperature of room temperature to the boiling point of the solvent used and is completed in 30 minutes to 48 hours.

Compound (I) having at least one lower alkoxy group as $R^2$, $R^3$, $R^4$, or $R^5$; or $R^6$, $R^7$, $R^8$, or $R^9$ can also be prepared from a corresponding Compound (I) having a hydroxyl group as $R^2$, $R^3$, $R^4$, or $R^5$; or $R^6$, $R^7$, $R^8$, or $R^9$ by the similar method as in Step 2.

Compound (I) having hydrogen as $R^{10}$ can also be prepared by subjecting a corresponding Compound (I) having halogen as $R^{10}$ to the above-mentioned catalytic reduction.

The intermediates and desired compounds in the above-described processes can be isolated and purified by purification methods conventionally used in organic synthetic chemistry, for example, neutralization, filtration, extraction, drying, concentration, recrystallization, and various kinds of chromatography. The intermediates may be subjected to the subsequent reaction without being purified.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable organic solvent, followed by addition of an acid or a base to form a salt.

Compounds (I) and pharmaceutically acceptable salts thereof may be in the form of adducts with water or various solvents, which can also be used as the drugs of the present invention.

Examples of Compounds (I) obtained by the above-described processes are shown in Tables 1 to 5.

TABLE 1-1

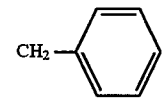

| Compd. No. | $R^1$ | $R^2$ | $R^3$ | $R^4$ | $R^5$ |
|---|---|---|---|---|---|
| 1 | $CH_3$ | H | $NO_2$ | H | H |
| 2 | $CH_2CH_3$ | H | $NO_2$ | H | H |
| 3 | $(CH_2)_2CH_3$ | H | $NO_2$ | H | H |
| 4 | $(CH_2)_3CH_3$ | H | $NO_2$ | H | H |
| 5 | $CH_2CH=CH_2$ | H | $NO_2$ | H | H |
| 6 | $CH_2CO_2CH_2CH_3$ | H | $NO_2$ | H | H |
| 7 | $CH_2CN$ | H | $NO_2$ | H | H |
| 8 | $CH_2$-C$_6$H$_5$ | | H | $NO_2$ | H | H |
| 9 | $CH_2$-C$_6$H$_4$-F | | H | $NO_2$ | H | H |

TABLE 1-1-continued

[Structure with R², R³, R⁴, R⁵ on benzene ring, connected via C=O to N-piperidine-N=C(pyrimidine)(dimethoxyphenyl), with N-R¹ and C=O]

| Compd. No. | R¹ | R² | R³ | R⁴ | R⁵ |
|---|---|---|---|---|---|
| 10 | CH₂-(2,6-dichlorophenyl) | H | NO₂ | H | H |
| 11 | CH₂-(4-nitrophenyl) | H | NO₂ | H | H |
| 12 | CH₂-(4-methoxyphenyl) | H | NO₂ | H | H |

TABLE 1-2

[Structure similar to above]

| Compd. No. | R¹ | R² | R³ | R⁴ | R⁵ |
|---|---|---|---|---|---|
| 13 | CH₂-(4-CO₂CH₃-phenyl) | H | NO₂ | H | H |
| 14 | CH₃ | H | NH₂ | H | H |
| 15 | CH₃ | H | H | H | Cl |
| 16 | CH₂CH₃ | H | CH₃ | H | H |
| 17 | (CH₂)₂CH₃ | H | CH₃ | H | H |
| 18 | CH₃ | H | NO₂ | H | Cl |
| 25 | CH₂CH(CH₃)₂ | H | NO₂ | H | H |
| 26 | CH₂-cyclopropyl | H | NO₂ | H | H |
| 27 | CH₂-cyclohexyl | H | NO₂ | H | H |
| 28 | CH₂CH₂N(CH₃)₂ | H | NO₂ | H | H |
| 29 | CH₂CH₂NH₂ | H | NO₂ | H | H |
| 30 | (CH₂)₃NH₂ | H | NO₂ | H | H |

TABLE 1-3

[Structure similar to above]

| Compd. No. | R¹ | R² | R³ | R⁴ | R⁵ |
|---|---|---|---|---|---|
| 31 | CH(CH₃)₂ | H | NO₂ | H | H |
| 32 | CH(CH₃)CH₂CH₃ | H | NO₂ | H | H |
| 33 | CH₂CH₂-N(phthalimide) | H | NO₂ | H | H |
| 34 | (CH₂)₃-N(phthalimide) | H | NO₂ | H | H |
| 35 | CH₂CH₃ | H | H | H | Cl |
| 36 | CH₂CH₃ | H | NO₂ | Cl | H |
| 37 | CH₂CH₃ | H | NO₂ | H | Cl |
| 38 | (CH₂)₂CH₃ | H | NO₂ | H | Cl |
| 39 | CH₂CH₃ | H | NO₂ | H | NO₂ |
| 40 | CH₃ | H | Cl | H | H |
| 41 | CH₂CH₃ | H | Cl | H | H |
| 42 | (CH₂)₂CH₃ | H | Cl | H | H |

TABLE 1-4

[Structure similar to above]

| Compd. No. | R¹ | R² | R³ | R⁴ | R⁵ |
|---|---|---|---|---|---|
| 43 | CH₂CH₃ | H | Cl | H | NO₂ |
| 44 | (CH₂)₂CH₃ | H | Cl | H | NO₂ |
| 45 | CH₃ | H | Br | H | H |
| 46 | CH₂CH₃ | H | Br | H | H |
| 47 | CH₂CH₃ | H | Br | Cl | H |
| 48 | CH₂CH₃ | H | Br | H | Br |
| 49 | CH₂CH₃ | H | H | Cl | H |
| 50 | CH₃ | H | CH₃ | H | H |
| 51 | (CH₂)₃CH₃ | H | CH₃ | H | H |
| 52 | (CH₂)₄CH₃ | H | CH₃ | H | H |
| 53 | CH₂CH=CH₂ | H | CH₃ | H | H |
| 54 | CH₃ | H | CH₂CH₃ | H | H |

TABLE 1-5

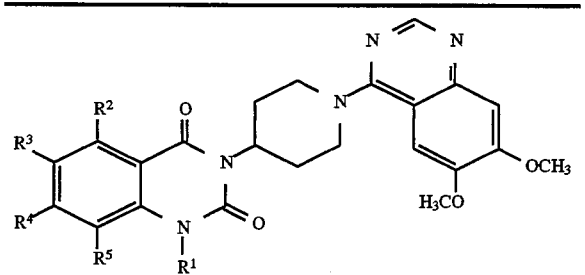

| Compd. No. | $R^1$ | $R^2$ | $R^3$ | $R^4$ | $R^5$ |
|---|---|---|---|---|---|
| 55 | $CH_3$ | H | $(CH_2)_2CH_3$ | H | H |
| 56 | $CH_3$ | H | $CH(CH_3)_2$ | H | H |
| 57 | $CH_3$ | $CH_3$ | H | H | H |
| 58 | $(CH_2)_2CH_3$ | $CH_3$ | H | H | H |
| 59 | $CH_3$ | H | H | H | $CH_3$ |
| 60 | $CH_3$ | H | $CH(OH)CH_3$ | H | H |
| 61 | $CH_3$ | H | $C(CH_3)_2OH$ | H | H |
| 62 | $CH_3$ | H | $CO_2H$ | H | H |
| 63 | $CH_3$ | H | $COCH_3$ | H | H |
| 64 | $CH_2CH_3$ | H | $NH_2$ | H | H |
| 65 | $CH_2CH_3$ | H | $NHCOCH_3$ | H | H |
| 66 | $CH_2CH_3$ | H | OH | H | H |

TABLE 1-6

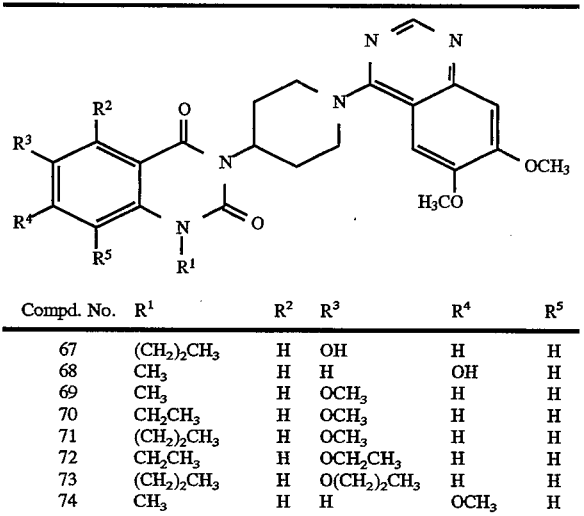

| Compd. No. | $R^1$ | $R^2$ | $R^3$ | $R^4$ | $R^5$ |
|---|---|---|---|---|---|
| 67 | $(CH_2)_2CH_3$ | H | OH | H | H |
| 68 | $CH_3$ | H | H | OH | H |
| 69 | $CH_3$ | H | $OCH_3$ | H | H |
| 70 | $CH_2CH_3$ | H | $OCH_3$ | H | H |
| 71 | $(CH_2)_2CH_3$ | H | $OCH_3$ | H | H |
| 72 | $CH_2CH_3$ | H | $OCH_2CH_3$ | H | H |
| 73 | $(CH_2)_2CH_3$ | H | $O(CH_2)_2CH_3$ | H | H |
| 74 | $CH_3$ | H | H | $OCH_3$ | H |

TABLE 2

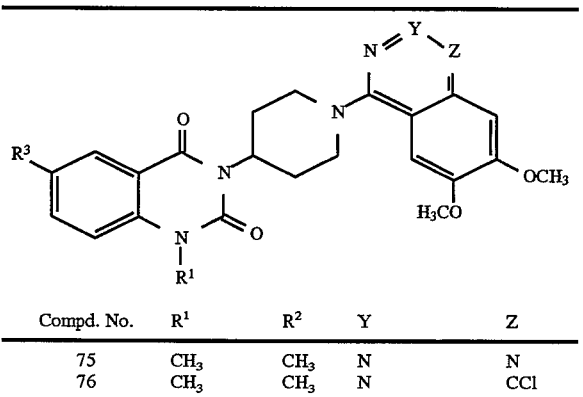

| Compd. No. | $R^1$ | $R^2$ | Y | Z |
|---|---|---|---|---|
| 75 | $CH_3$ | $CH_3$ | N | N |
| 76 | $CH_3$ | $CH_3$ | N | CCl |

TABLE 2-continued

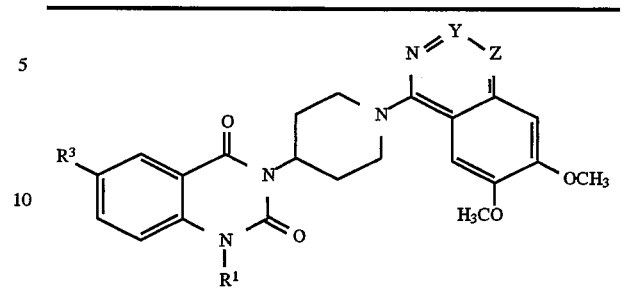

| Compd. No. | $R^1$ | $R^2$ | Y | Z |
|---|---|---|---|---|
| 77 | $CH_3$ | $CH_3$ | N | CH |
| 78 | $CH_3$ | $CH_3$ | CCl | N |
| 79 | $CH_2CH_3$ | $NO_2$ | CCl | N |
| 80 | $CH_3$ | $CH_3$ | $CCH_3$ | N |
| 81 | $CH_2CH_3$ | $NO_2$ | $CCH_3$ | N |
| 82 | $CH_3$ | $CH_3$ | $CCH_2CH_3$ | N |
| 83 | $CH_3$ | $CH_3$ | $CCH(CH_3)_2$ | N |

TABLE 3-1

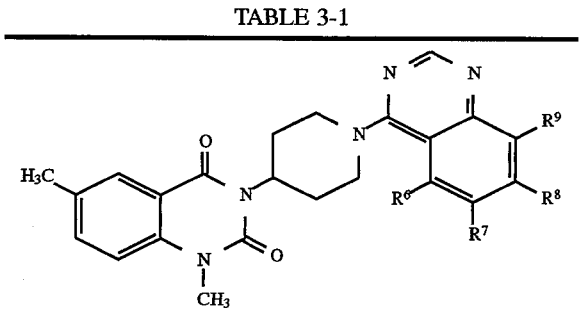

| Compd. No. | $R^6$ | $R^7$ | $R^8$ | $R^9$ |
|---|---|---|---|---|
| 84 | H | $OCH_3$ | H | H |
| 85 | H | H | $OCH_3$ | H |
| 86 | H | $OCH_3$ | $OCH_3$ | $OCH_3$ |
| 87 | H | $OCH_3$ | $OCH_2C_6H_5$ | H |
| 88 | H | $OCH_2C_6H_5$ | $OCH_2C_6H_5$ | H |
| 89 | H | $OCH_3$ | OH | H |
| 90 | H | OH | $OCH_3$ | H |
| 91 | H | $OCH_3$ | $O(CH_2)_2CH_3$ | H |
| 92 | H | $O(CH_2)_2CH_3$ | $OCH_3$ | H |

TABLE 3-2

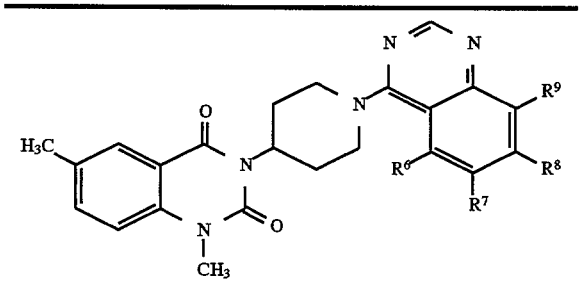

| Compd. No. | $R^6$ | $R^7$ | $R^8$ | $R^9$ |
|---|---|---|---|---|
| 93 | H | $OCH_3$ | $OCH_2CO_2CH_2CH_3$ | H |
| 94 | H | $OCH_2CO_2CH_2CH_3$ | $OCH_3$ | H |
| 95 | H | $OCH_3$ | $OCH_2CO_2H$ | H |
| 96 | H | $OCH_3$ | $OCH_2CH_2N(CH_3)_2$ | H |
| 97 | H | OH | OH | H |
| 98 | H | $OCH_2CH_3$ | $OCH_2CH_3$ | H |

TABLE 3-2-continued
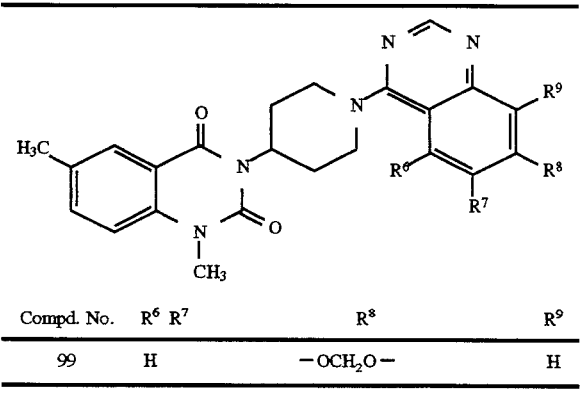
| Compd. No. | R⁶ | R⁷ | R⁸ | R⁹ |
|---|---|---|---|---|
| 99 | H | | —OCH₂O— | H |
TABLE 4
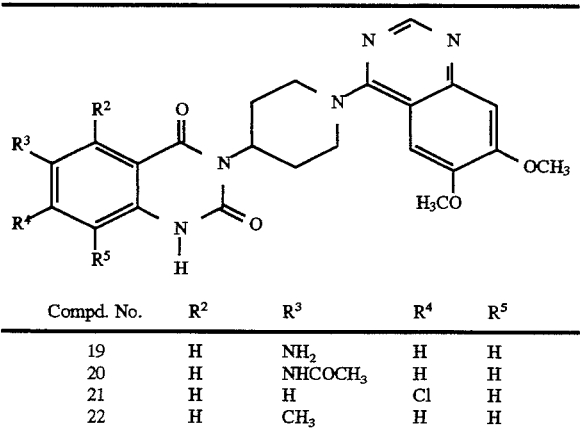
| Compd. No. | R² | R³ | R⁴ | R⁵ |
|---|---|---|---|---|
| 19 | H | NH₂ | H | H |
| 20 | H | NHCOCH₃ | H | H |
| 21 | H | H | Cl | H |
| 22 | H | CH₃ | H | H |
TABLE 4-continued
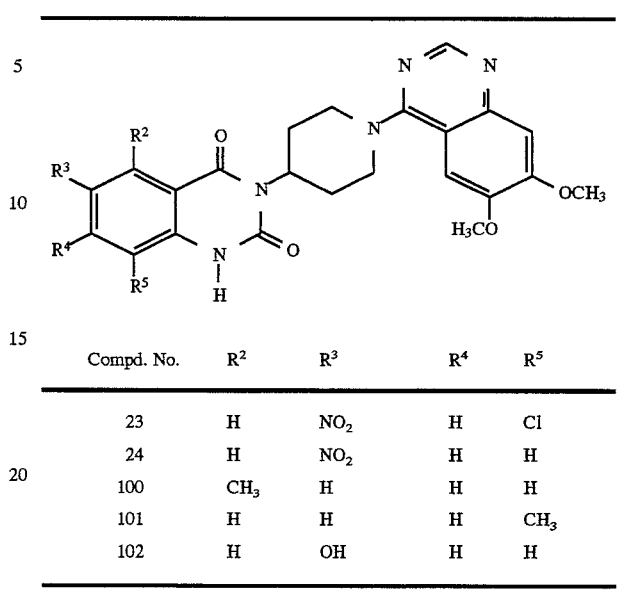
| Compd. No. | R² | R³ | R⁴ | R⁵ |
|---|---|---|---|---|
| 23 | H | NO₂ | H | Cl |
| 24 | H | NO₂ | H | H |
| 100 | CH₃ | H | H | H |
| 101 | H | H | H | CH₃ |
| 102 | H | OH | H | H |
TABLE 5
| Compd. No. |
|---|
| 103 |
| 104 |
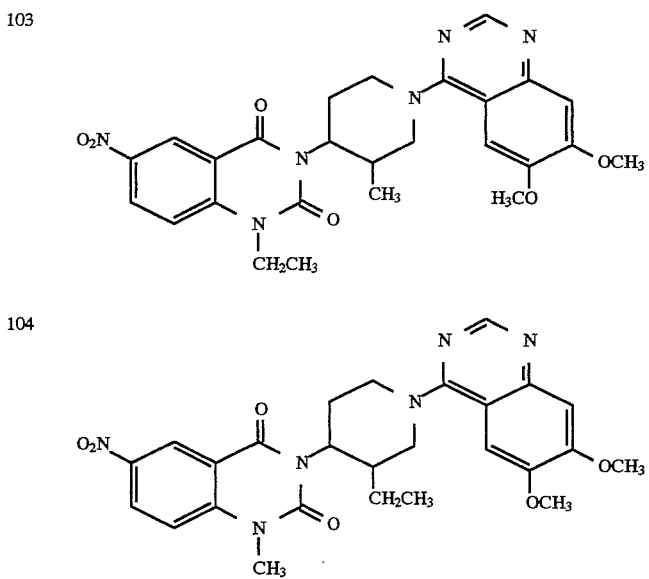

TABLE 5-continued

| Compd. No. | |
|---|---|
| 105 | 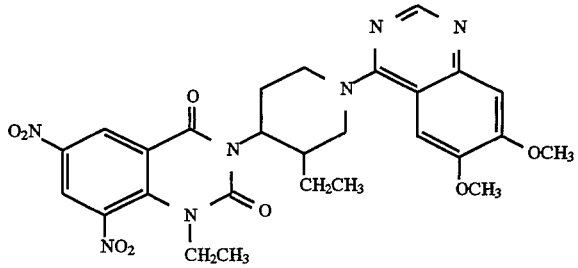 |
| 106 | 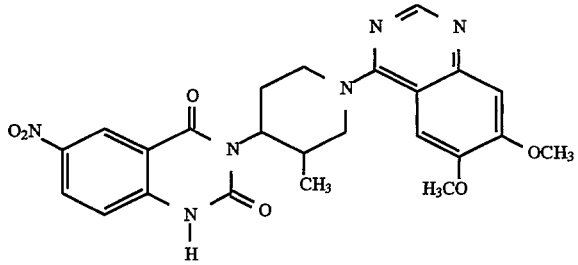 |
| 107 | 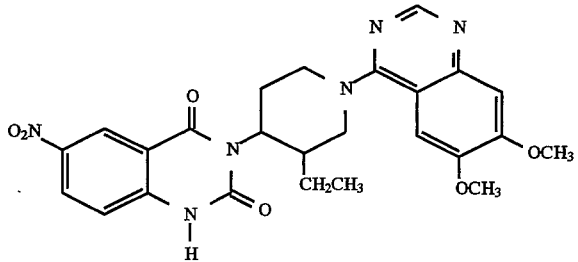 |
| 108 | 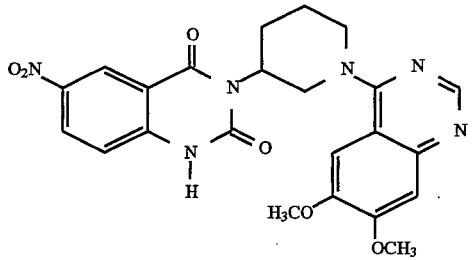 |

The pharmacological activities of typical Compounds (I) are shown below by Test Examples.

Test Example 1 Inhibitory Effect on [$^3$H]-Adenosine Uptake

A blood sample was obtained from a healthy male adult under 40 years of age by brachial venipuncture using a syringe containing citrate and subjected to centrifugation to obtain washed erythrocytes. To 100 μl of an erythrocyte suspension (2.5×10$^9$/ml) was added 10 μl of a 21% DMSO solution of a test compound. After allowing the suspension to stand at room temperature for 1 hour, 100 μl of a [$^3$H]-adenosine solution was added thereto. Ten seconds later, 200 μl of a dilazep solution (1 mg/ml) was added to stop the reaction. The erythrocytes were dissolved in Triton X-100, and the uptake amount of $^3$H was measured with a liquid scintillation counter. The concentration of the test compound which inhibits the [$^3$H]-adenosine uptake by 50% (IC$_{50}$) was calculated. The results obtained are shown in Table 6.

TABLE 6

| Compound No. | [$^3$H]-Adenosine Uptake Inhibition IC$_{50}$ (nM) |
|---|---|
| 1 | 42 |
| 2 | 103 |
| 3 | 62 |
| 6 | 462 |
| 8 | 295 |
| 24 | 38 |
| 45 | 54 |
| 50 | 54 |
| 55 | 171 |
| 63 | 88 |
| 69 | 157 |
| 80 | 127 |

Test Example 2 Inhibitory Effect on [$^3$H]-Nitrobenzylthioinosine (NBI) Binding (an indication of adenosine uptake inhibitory activity)

The cerebral cortex of a male guinea pig of Hartley strain was homogenized with an ice-cooled 50 mM tris-HCl buffer (pH 7.4) in an amount of 25 times (w/v) that of the tissue. The homogenate was centrifuged (30,000×g, 4° C., 20 mins.), and the supernatant was discarded. To the precipitate was added the same amount of the buffer, followed by homogenization and then centrifugation in the same manner as above. The obtained precipitate was suspended in 20 times as much buffer as the precipitate to prepare a suspension for testing.

To a DMSO solution of a test compound were added 1.5 nM of [$^3$H]-NBI and 5 mg (wet basis) of the tissue homogenate, and the mixture was allowed to stand at 25° C. for 30 minutes. To the mixture was added 4 ml of an ice-cooled buffer, followed by rapid filtration with suction through a glass filter (GF/C, produced by Whatman Ltd.) or a Ready filter (produced by Beckman Co.) to stop the reaction. The filter was transferred to a scintillation vial, and after drying, Scintisol EX-H was added thereto. The radioactivity was measured with a liquid scintillation counter. The binding inhibitory activity was expressed in terms of an inhibition constant (Ki value) as calculated according to Cheng-Prusoff's formula. The results obtained are shown in Table 7 below.

TABLE 7

| Compound No. | [$^3$H]-NBI Binding Ki Value (nM) |
| --- | --- |
| 1 | 18 |
| 2 | 18 |
| 3 | 4.3 |
| 24 | 15 |
| 45 | 6.9 |
| 50 | 12 |
| 69 | 11 |

Test Example 3 Inhibitory Effect on Ischemic Paw Edema in Mice

Ischemia followed by reperfusion in the limb of a mouse induces paw edema due to membrane injury in which active oxygen is involved [Arzneim.-Forsch., 41, 469–474 (1991)]. In general, peroxidation of membrane lipid and calcium influx into cells play roles in ischemia-reperfusion injury [Life Science, 29, 1289–1295 (1981); Japan J. Pharmacol., 52, 553–562 (1990)]. It is active oxygen production that triggers these factors, and the source of active oxygen includes endothelial cells and leukocytes [J. Mol. Cell Cardiol., 20 (Suppl. II), 55–63 (1988); Blood, 73, 301–306 (1989)]. As possible mechanisms for suppression of paw edema development, inhibition of activation of leukocytes by adenosine which has increased in the ischemic site, inhibition of active oxygen production which is accompanied by activation of leukocytes, and inhibition of calcium overload due to the cyclic AMP increasing activity of adenosine have been suggested [Am. J. Physiol., 257, H1334–1339 (1989); J. Immunol., 135, 1366–1371 (1985)]. Accordingly, it is believed that a compound effective on an ischemic podedema model in mice as hereinafter described would provide a convenient and useful model for evaluating an adenosine uptake inhibitor.

Experiments were conducted in accordance with the method described in Arzneim.-Forsch., 41, 469–474 (1991). A test compound was suspended in water and orally given to grouped male mice of ddY-strain weighing 25 to 30 g at a dose of 30 mg/kg. One hour later, the left hind limb was bound with a rubber band for 20 minutes to cause ischemia, and 20, 40 and 60 minutes after blood recirculation, the paw thickness was measured with a pair of calipers (Digimatic Caliper manufactured by Mitsutoyo K.K.). The paw edema was determined as the difference in thickness between the left hind paw (ischemia-treated) and the non-treated right one. Each result was expressed in terms of percent suppression of edema in a test compound group on the basis of the edema in a control group. The results obtained are shown in Table 8 below.

TABLE 8

| | Paw Edema Supression Rate (%) | | |
| --- | --- | --- | --- |
| Compound No. | After 20 minutes | After 40 minutes | After 60 minutes |
| 2 | 4.1 ± 2.98 | 9.0 ± 3.79 | 15.5 ± 4.09 |
| 3 | 4.8 ± 4.40 | 11.6 ± 2.68 | 14.9 ± 3.58 |

Test Example 4 Acute Toxicity Test

A test compound was intraperitoneally or orally administered to groups of ddY-strain male mice weighing 20±1 g, each group consisting of three mice. Seven days after the administration, the mortality was observed to obtain a minimum lethal dose (MLD) of the compound. The results obtained are shown in Table 9 below.

TABLE 9

| Compound | MLD (mg/kg) | |
| --- | --- | --- |
| No. | p.o. | i.p. |
| 2 | >300 | >100 |
| 3 | >300 | >100 |

Compounds (I) and pharmaceutically acceptable salts thereof can be formulated into generally employed dose forms, such as tablets, capsules, syrups, injections, drips, and suppositories, and administered orally or parenterally through intramuscular injection, intravenous injection, intraarterial injection, drip infusion, or rectal administration using suppositories. For preparing these dose forms for oral or parenteral administration, generally known techniques are applied. For example, the preparations may contain various excipients, lubricants, binders, disintegrating agents, suspending agents, isotonizing agents, emulsifiers, and the like.

Examples of the carriers which can be used are water, injectable distilled water, physiological saline, glucose, fructose, sucrose, mannitol, lactose, starch, cellulose, methyl cellulose, carboxymethyl cellulose, hydroxypropyl cellulose, alginic acid, talc, sodium citrate, calcium carbonate, calcium hydrogenphosphate, magnesium stearate, urea, silicone resins, sorbitan fatty acid esters, and glycerin fatty acid esters.

The dose varies depending upon the mode of administration, the age, body weight, and conditions of a patient, etc. However, generally, Compound (I) or a pharmaceutically acceptable salt thereof is administered in a dose of 1 to 900 mg/60 kg/day either orally or parenterally.

Certain embodiments of the present invention are illustrated in the following Examples and Reference Examples.

BEST MODE FOR CARRYING OUT THE INVENTION

Example 1

3-[1-(6,7-Dimethoxy-4-quinazolinyl)-4-piperidinyl]-1,2,3,4-tetrahydro-1-methyl-6-nitro-2,4-dioxoquinazoline (Compound 1)

In 1 ml of DMF was dissolved 239 mg (0.5 mmol) of 3-[1-(6,7-dimethoxy-4-quinazolinyl)-4-piperidinyl]-1,2,3,4-tetrahydro-6-nitro-2,4-dioxoquinazoline (Compound 24) obtained in Reference Example 6, and the solution was added dropwise to a solution of 22 mg (0.55 mmol) of 60% sodium hydride in 2 ml of DMF under ice cooling. After stirring for 20 minutes, 0.031 ml (0.5 mmol) of methyl iodide was added thereto, followed by stirring at room temperature for 1 hour. A saturated aqueous solution of ammonium chloride was added to the reaction mixture, and the precipitated solid was collected by filtration. The solid was washed with water, dried by heating, and recrystallized from ethanol/ether to give 152.9 mg (yield: 62%) of Compound 1 as pale yellow crystals.

$^1$H-NMR (CDCl$_3$) δ (ppm): 9.08 (d, 1H, J=2.5 Hz), 8.70 (s, 1H), 8.51 (dd, 1H, J=9.0, 2.5 Hz), 7.32 (d, 1H, J=9.0 Hz), 7.27 (s, 1H), 7.18 (s, 1H), 5.31–5.23 (m, 1H), 4.37–4.32 (br.-d, 2H), 4.04 (s, 3H), 4.02 (s, 3H), 3.67 (s, 3H), 3.25–3.16 (br.-t, 2H), 3.09–2.96 (m, 2H), 1.88–1.83 (br.-d, 2H).

IR (KBr tab.) (cm$^{-1}$): 1710, 1664, 1612, 1504, 1330.

Melting Point (ethanol-ether): 286°–287° C. (decomposition)

Example 2

3-[1-(6,7-Dimethoxy-4-quinazolinyl)-4-piperidinyl]-1-ethyl-1,2,3,4-tetrahydro-6-nitro-2,4-dioxoquinazoline (Compound 2)

The procedure similar to that described in Example 1 was repeated, except that 300 mg (0.63 mmol) of Compound 24 was used and ethyl iodide was used in place of methyl iodide. As a result, 213.1 mg (yield: 67%) of Compound 2 was obtained as pale yellow crystals.

$^1$H-NMR (CDCl$_3$) δ (ppm): 9.09 (d, 1H, J=2.5 Hz), 8.69 (s, 1H), 8.51 (dd, 1H, J=9.0, 2.5 Hz), 7.32 (d, 1H, J=9.0 Hz), 7.29 (s, 1H), 7.18 (s, 1H), 5.31–5.22 (m, 1H), 4.39–4.34 (br.-d, 2H), 4.25 (q, 2H, J=7.5 Hz), 4.04 (s, 3H), 4.02 (s, 3H), 3.26–3.16 (br.-t, 2H), 3.10–2.96 (m, 2H), 1.89–1.84 (br.-d, 2H), 1.40 (t, 3H, J=7.5 Hz).

IR (KBr tab.) (cm$^{-1}$): 1713, 1657, 1610, 1505, 1323.

Melting Point (ether): 267°–268° C.

Example 3

3-[1-(6,7-Dimethoxy-4-quinazolinyl)-4-piperidinyl]-1,2,3,4-tetrahydro-6-nitro-2,4-dioxo-1-propyl-quinazoline (Compound 3)

The procedure similar to that described in Example 1 was repeated, except that 300 mg (0.63 mmol) of Compound 24 was used and propyl iodide was used in place of methyl iodide. As a result, 209.9 mg (yield: 64%) of Compound 3 was obtained as pale yellow crystals.

$^1$H-NMR (CDCl$_3$) δ (ppm): 9.09 (d, 1H, J=2.5 Hz), 8.70 (s, 1H), 8.49 (dd, 1H, J=9.0, 2.5 Hz), 7.29 (d, 1H, J=9.0 Hz), 7.29 (s, 1H), 7.18 (s, 1H), 5.30–5.20 (m, 1H), 4.37–4.32 (br.-d, 2H), 4.12 (dist.-t, 2H), 4.04 (s, 3H), 4.02 (s, 3H), 3.25–3.16 (br.-t, 2H), 3.10–2.96 (m, 2H), 1.88–1.76 (m, 4H), 1.07 (t, 3H, J=7.5 Hz).

IR (KBr tab.) (cm$^{-1}$): 1713, 1667, 1613, 1499, 1450, 1326.

Melting Point (ether): 234°–236° C.

Example 4

1-Butyl-3-[1-(6,7-dimethoxy-4-quinazolinyl)-4-piperidinyl]-1,2,3,4-tetrahydro-6-nitro-2,4-dioxoquinazoline (Compound 4)

The procedure similar to that described in Example 1 was repeated, except that 334.6 mg (0.7 mmol) of Compound 24 was used and butyl iodide was used in place of methyl iodide. As a result, 228.9 mg (yield: 61%) of Compound 4 was obtained as pale yellow crystals.

$^1$H-NMR (CDCl$_3$) δ (ppm): 9.09 (d, 1H, J=2.5 Hz), 8.69 (s, 1H), 8.50 (dd, 1H, J=9.0, 2.5 Hz), 7.32 (d, 1H, J=9.0 Hz), 7.26 (s, 1H), 7.18 (s, 1H), 5.32–5.23 (m, 1H), 4.43–4.38 (br.-d, 2H), 4.18–4.12 (dist.-t, 2H), 4.05 (s, 3H), 4.02 (s, 3H), 3.28–3.19 (br.-t, 2H), 3.08–2.96 (m, 2H), 1.89–1.84 (br.-d, 2H), 1.76–1.68 (m, 2H), 1.56–1.45 (m, 2H), 1.03 (t, 3H, J=7.5 Hz).

IR (KBr tab.) (cm$^1$): 1716, 1673, 1616, 1505, 1453, 1332.

Melting Point (ethyl acetate-ether): 194°–195° C.

Example 5

3-[1-(6,7-Dimethoxy-4-quinazolinyl)-4-piperidinyl]-1,2,3,4-tetrahydro-6-nitro-2,4-dioxo-1-(2-propenyl)-quinazoline (Compound 5)

The procedure similar to that described in Example 1 was repeated, except that 334.6 mg (0.7 mmol) of Compound 24 was used and allyl bromide was used in place of methyl iodide. As a result, 192.8 mg (yield: 53%) of Compound 5 was obtained as pale yellow crystals.

$^1$H-NMR (CDCl$_3$) δ (ppm): 9.09 (d, 1H, J=2.5 Hz), 8.69 (s, 1H), 8.47 (dd, 1H, J=9.0, 2.5 Hz), 7.30 (s, 1H), 7.29 (d, 1H, J=9.0 Hz), 7.18 (s, 1H), 5.94 (ddt, 1H, J=17, 10, 5 Hz), 5.37–5.22 (m, 3H), 4.82 (d, 2H, J=5 Hz), 4.41–4.36 (br.-d, 2H), 4.04 (s, 3H), 4.02 (s, 3H), 3.27–3.18 (br.-t, 2H), 3.10–2.97 (m, 2H), 1.90–1.85 (br.-d, 2H).

IR (KBr tab.) (cm$^{-1}$): 1720, 1672, 1616, 1504, 1468, 1428, 1337.

Melting Point (ethyl acetate-ether): 225°–226° C.

Example 6

3-[1-(6,7-Dimethoxy-4-quinazolinyl)-4-piperidinyl]-1-ethoxycarbonylmethyl-1,2,3,4-tetrahydro-6-nitro-2,4-dioxoquinazoline (Compound 6)

The procedure similar to that described in Example 1 was repeated, except that 300 mg (0.63 mmol) of Compound 24 was used and ethyl bromoacetate was used in place of methyl iodide. As a result, 61.3 mg (yield: 17%) of Compound 6 was obtained as pale yellow crystals.

$^1$H-NMR (CDCl$_3$) δ (ppm): 9.10 (d, 1H, J=2.5 Hz), 8.66 (s, 1H), 8.49 (dd, 1H, J=9.0, 2.5 Hz), 7.26 (s, 1H), 7.16 (s, 1H), 7.08 (d, 1H, J=9.0 Hz), 5.37–5.22 (m, 1H), 4.92 (s, 2H), 4.54–4.49 (br.-d, 2H), 4.29 (q, 2H, J=7.5 Hz), 4.07 (s, 3H), 4.01 (s, 3H), 3.35–3.28 (br.-t, 2H), 3.01–2.95 (m, 2H), 1.95–1.90 (br.-d, 2H), 1.33 (t, 3H, J=7.5 Hz).

IR (KBr tab.) (cm$^{-1}$): 1719, 1671, 1618, 1509, 1468, 1336, 1216.

Melting Point (ether): 201°–202° C.

Example 7

1-Cyanomethyl-3-[1-(6,7-dimethoxy-4-quinazolinyl)-4-piperidinyl]-1,2,3,4-tetrahydro-6-nitro-2,4-dioxoquinazoline (Compound 7)

The procedure similar to that described in Example 1 was repeated, except that 300 mg (0.63 mmol) of Compound 24 was used and bromoacetonitrile was used in place of methyl iodide. As a result, 87.3 mg (yield: 27%) of Compound 7 was obtained as pale yellow crystals.

$^1$H-NMR (CDCl$_3$) δ (ppm): 9.13 (d, 1H, J=2.5 Hz), 8.67 (s, 1H), 8.62 (dd, 1H, J=9.0, 2.5 Hz), 7.38 (d, 1H, J=9.0 Hz), 7.26 (s, 1H), 7.15 (s, 1H), 5.36–5.26 (m, 1H), 5.15 (s, 2H), 4.57–4.52 (br.-d, 2H), 4.07 (s, 3H), 4.02 (s, 3H), 3.37–3.27 (br.-t, 2H), 2.98–2.94 (m, 2H), 2.00–1.94 (br.-d, 2H).

IR (KBr tab.) (cm$^{-1}$): 2250, 1719, 1676, 1614, 1339.

Melting Point (ether): 261°–262° C.

Example 8

1-Benzyl-3-[1-(6,7-dimethoxy-4-quinazolinyl)-4-piperidinyl]-1,2,3,4-tetrahydro-6-nitro-2,4-dioxo-quinazoline (Compound 8)

The procedure similar to that described in Example 1 was repeated, except that 200 mg (0.42 mmol) of Compound 24 was used and benzyl bromide was used in place of methyl iodide. As a result, 190.5 mg (yield: 80%) of Compound 8 was obtained as pale yellow crystals.

$^1$H-NMR (CDCl$_3$) δ (ppm): 9.08 (d, 1H, J=2.5 Hz), 8.66 (s, 1H), 8.47 (dd, 1H, J=9.0, 2.5 Hz), 7.49–7.22 (m, 7H), 7.17 (s, 1H), 5.41 (s, 2H), 5.40–5.37 (m, 1H), 4.56–4.51 (br.-d, 2H), 4.06 (s, 3H), 4.01 (s, 3H), 3.37–3.28 (br.-t, 2H), 3.11–2.98 (m, 2H), 1.97–1.94 (br.-d, 2H).

IR (KBr tab ) (cm$^{-1}$): 1712, 1666, 1616, 1500, 1331.

Melting Point (ether): 159°–162° C.

Example 9

3-[1-(6,7-Dimethoxy-4-quinazolinyl)-4-piperidinyl]-1-(4-fluorobenzyl)-1,2,3,4-tetrahydro-6-nitro-2,4-dioxo-quinazoline (Compound 9)

The procedure similar to that described in Example 1 was repeated, except that 300 mg (0.63 mmol) of Compound 24 was used and 4-fluorobenzyl chloride was used in place of methyl iodide. As a result, 116.9 mg (yield: 32%) of Compound 9 was obtained as pale yellow crystals.

$^1$H-NMR (CDCl$_3$) δ (ppm): 9.09 (d, 1H, J=2.5 Hz), 8.67 (s, 1H), 8.40 (dd, 1H, J=9.0, 2.5 Hz), 7.26–7.02 (m, 7H), 5.37 (s, 2H), 5.37–5.20 (m, 1H), 4.51–4.46 (br.-d, 2H), 4.05 (s, 3H), 4.01 (s, 3H), 3.34–3.25 (br.-t, 2H), 3.12–2.96 (m, 2H), 1.95–1.91 (br.-d, 2H).

IR (KBr tab.) (cm$^{-1}$): 1713, 1667, 1613, 1510, 1503, 1329.

Melting Point (ether): 240°–243° C.

Example 10

1-(2,6-Dichlorobenzyl)-3-[1-(6,7-dimethoxy-4-quinazolinyl)-4-piperidinyl]-1,2,3,4-tetrahydro-6-nitro-2,4-dioxoquinazoline (Compound 10)

The procedure similar to that described in Example 1 was repeated, except that 300 mg (0.63 mmol) of Compound 24 was used and 2,6-dichlorobenzyl bromide was used in place of methyl iodide. As a result, 117.1 mg (yield: 29%) of Compound 10 was obtained as pale yellow crystals.

$^1$H-NMR (CDCl$_3$) δ (ppm): 9.05 (d, 1H, J=2.5 Hz), 8.68 (s, 1H), 8.33 (dd, 1H, J=9.0, 2.5 Hz), 7.39–7.11 (m, 6H), 5.78 (s, 2H), 5.40–5.25 (m, 1H), 4.47–4.44 (br.-d, 2H), 4.05 (s, 3H), 4.01 (s, 3H), 3.31–3.22 (br.-t, 2H), 3.06–2.89 (m, 2H), 1.92–1.87 (br.-d, 2H).

IR (KBr tab.) (cm$^{-1}$): 1718, 1669, 1615, 1503, 1468, 1332.

Melting Point (ether): 231°–234° C.

Example 11

3-[1-(6,7-Dimethoxy-4-quinazolinyl)-4-piperidinyl]-1,2,3,4-tetrahydro-6-nitro-1-(4-nitrobenzyl)-2,4-dioxoquinazoline (Compound 11)

The procedure similar to that described in Example 1 was repeated, except that 300 mg (0.63 mmol) of Compound 24 was used and 4-nitrobenzyl bromide was used in place of methyl iodide. As a result, 145.0 mg (yield: 38%) of Compound 11 was obtained as pale yellow crystals.

$^1$H-NMR (CDCl$_3$) δ (ppm): 9.11 (d, 1H, J=2.5 Hz), 8.68 (s, 1H), 8.40 (dd, 1H, J=9.0, 2.5 Hz), 8.25 (d, 2H, J=8.5 Hz), 7.43 (d, 2H, J=8.5 Hz), 7.37 (s, 1H), 7.17 (s, 1H), 7.12 (d, 1H, J=9.0 Hz), 5.50 (s, 2H), 5.38–5.28 (m, 1H), 4.47–4.42 (br.-d, 2H), 4.04 (s, 3H), 4.01 (s, 3H), 3.67–3.62 (br.-t, 2H), 3.32–3.01 (m, 2H), 1.94–1.90 (br.-d, 2H).

IR (KBr tab.) (cm$^{-1}$): 1714, 1666, 1617, 1332.

Melting Point (diisopropyl ether): 158°–161° C.

Example 12

3-[1-(6,7-Dimethoxy-4-quinazolinyl)-4-piperidinyl]-1,2,3,4-tetrahydro-1-(4-methoxybenzyl)-6-nitro-2,4-dioxoquinazoline (Compound 12)

The procedure similar to that described in Example 1 was repeated, except that 300 mg (0.63 mmol) of Compound 24 was used and 4-methoxybenzyl chloride was used in place of methyl iodide. As a result, 232.5 mg (yield: 62%) of Compound 12 was obtained as pale yellow crystals.

$^1$H-NMR (CDCl$_3$) δ (ppm): 9.08 (d, 1H, J=2.5 Hz), 8.69 (s, 1H), 8.38 (dd, 1H, J=9.0, 2.5 Hz), 7.35 (s, 1H), 7.28 (d, 1H, J=9.0 Hz), 7.20 (d, 2H, J=8.9 Hz), 7.18 (s, 1H), 6.89 (d, 2H, J=8.9 Hz), 5.35 (s, 2H), 5.35–5.30 (m, 1H), 4.45–4.40 (br.-d, 2H), 4.05 (s, 3H), 4.02 (s, 3H), 3.79 (s, 3H), 3.31–3.22 (br.-t, 2H), 3.12–3.03 (m, 2H), 1.94–1.90 (br.-d, 2H).

IR (KBr tab.) (cm$^{-1}$): 1708, 1665, 1613, 1510, 1317.

Melting Point (ethyl acetate-ether): 236°–237° C.

Example 13

3-[1-(6,7-Dimethoxy-4-quinazolinyl)-4-piperidinyl]-1,2,3,4-tetrahydro-1-(4-methoxycarbonylbenzyl)-6-nitro-2,4-dioxoquinazoline (Compound 13)

The procedure similar to that described in Example 1 was repeated, except that 300 mg (0.63 mmol) of Compound 24 was used and 4-methoxycarbonylbenzyl bromide was used in place of methyl iodide. As a result, 101.2 mg (yield: 26%) of Compound 13 was obtained as pale yellow crystals.

$^1$H-NMR (CDCl$_3$) δ (ppm): 9.10 (d, 1H, J=2.5 Hz), 8.68 (s, 1H), 8.37 (dd, 1H, J=9.0, 2.5 Hz), 8.04 (d, 2H, J=8.4 Hz), 7.37 (s, 1H), 7.31 (d, 2H, J=8.4 Hz), 7.17 (s, 1H), 7.15 (d, 1H, J=9.0 Hz), 5.46 (s, 2H), 5.40–5.34 (m, 1H), 4.47–4.42 (br.-d, 2H), 4.04 (s, 3H), 4.01 (s, 3H), 3.91 (s, 3H), 3.32–3.21 (br.-t, 2H), 3.08–3.02 (m, 2H), 1.95–1.91 (br.-d, 2H).

IR (KBr tab.) (cm$^{-1}$): 1716, 1667, 1616, 1330.

Melting Point (ethyl acetate-ether): 146°–150° C.

Example 14

6-Amino-3-[1-(6,7-dimethoxy-4-quinazolinyl)-4-piperidinyl]-1,2,3,4-tetrahydro-1-methyl-2,4-dioxo-quinazoline (Compound 14)

In a solvent mixture of 15 ml of ethanol and 5 ml of water was dissolved 500 mg (1.02 mmol) of Compound 1 obtained in Example 1, and 500 mg of iron and a catalytic amount of ferric chloride were added thereto, followed by heating under reflux for 1 hour. The reaction mixture was filtered while hot by using a filter aid, and the filtrate was concentrated under reduced pressure. Water was added to the residue, and the mixture was adjusted to pH 7 with an aqueous solution of sodium bicarbonate and extracted with chloroform. The organic layer was washed and dried, and the solvent was distilled off under reduced pressure. The residue was purified by silica gel column chromatography (eluent: chloroform/methanol=50/1) and recrystallized from ether to give 275.2 mg (yield: 63%) of Compound 14 as pale yellow crystals.

$^1$H-NMR (CDCl$_3$) δ (ppm): 8.67 (s, 1H), 7.48 (m, 1H), 7.31 (s, 1H), 7.19 (s, 1H), 7.03 (m, 2H), 5.34–5.24 (m, 1H), 4.40–4.35 (br.-d, 2H), 4.04 (s, 3H), 4.01 (s, 3H), 3.55 (s, 3H), 3.25–2.99 (m, 4H), 1.88–1.83 (br.-d, 2H).

IR (KBr tab.) (cm$^{-1}$): 3400 (br.), 1694, 1650, 1505, 1340.

Melting Point (ether): 245°–247° C.

Example 15

8-Chloro-3-[1-(6,7-dimethoxy-4-quinazolinyl)-4-piperidinyl]-1,2,3,4-tetrahydro-1-methyl-2,4-dioxo-quinazoline (Compound 15)

In 10 ml of 48% hydrobromic acid was dissolved 451.8 mg (1.24 mmol) of 8-chloro-3-(1-ethoxycarbonyl-4-piperidinyl)-1,2,3,4-tetrahydro-1-methyl-2,4-dioxoquinazoline (Compound a) obtained in Reference Example 7, and the solution was heated under reflux for 1 hour. After the solvent was distilled off, ethanol was added to the residue, and the precipitated crystals were collected by filtration to give 119.5 mg of crude 8-chloro-1,2,3,4-tetrahydro-1-methyl-2,4-dioxo-3-(4-piperidinyl)quinazoline hydrobromide. The crude product was dissolved in 10 ml of DMF, and 65 mg (0.29 mmol) of 4-chloro-6,7-dimethoxyquinazoline and 122 mg (0.87 mmol) of potassium carbonate were added thereto, followed by heating at 120° C. for 2 hours. To the reaction mixture were added water and dilute hydrochloric acid for neutralization, and the mixture was extracted with chloroform. The organic layer was washed with an aqueous solution of sodium chloride and dried. The solvent was distilled off, and the residue was purified by silica gel column chromatography (eluent: chloroform/methanol=50/1). Ethyl acetate and ether were added to the product, and the precipitated crystals were collected by filtration and washed with ether to give 55.2 mg (yield: 8.9%) of Compound 15 as white crystals.

$^1$H-NMR (CDCl$_3$) δ (ppm): 8.68 (s, 1H), 8.14 (dd, 1H, J=8.0, 1.5 Hz), 7.67 (dd, 1H, J=8.0, 1.5 Hz), 7.28 (s, 1H), 7.19 (dd, 1H, J=8.0, 8.0 Hz), 7.18 (s, 1H), 5.18–5.09 (m, 1H), 4.37–4.31 (br.-d, 2H), 4.03 (s, 3H), 4.01 (s, 3H), 3.83 (s, 3H), 3.33–3.21 (br.-t, 2H), 3.09–2.93 (m, 2H), 1.89–1.85 (br.-d, 2H).

IR (KBr tab.) (cm$^{-1}$): 1704, 1656, 1503, 1460, 1341.

Melting Point (ether): 200°–202° C.

Example 16

3-[1-(6,7-Dimethoxy-4-quinazolinyl)-4-piperidinyl]-1-ethyl-1,2,3,4-tetrahydro-6-methyl-2,4-dioxoquinazoline (Compound 16)

The procedure similar to that described in Example 15 was repeated, except that 850.0 mg (2.37 mmol) of 3-(1-ethoxycarbonyl-4-piperidinyl)-1-ethyl-1,2,3,4-tetrahydro-6-methyl-2,4-dioxoquinazoline (Compound b) obtained in Reference Example 8 was used in place of Compound a, whereby 599.0 mg of crude 1-ethyl-1,2,3,4-tetrahydro-6-methyl-2,4-dioxo-3-(4-piperidinyl)quinazoline hydrobromide was obtained. The product (300.0 mg) was treated in the similar manner as in Example 15 to give 355.4 mg (yield: 62.8%) of Compound 16 as white crystals.

$^1$H-NMR (CDCl$_3$) δ (ppm): 8.68 (s, 1H), 8.02 (d, 1H, J=1.5 Hz), 7.48 (dd, 1H, J=8.4, 1.5 Hz), 7.27 (s, 1H), 7.19 (s, 1H), 7.10 (d, 1H, J=8.4 Hz), 5.32–5.24 (m, 1H), 4.37–4.32 (br.-d, 2H), 4.17 (q, 2H, J=7.0 Hz), 4.03 (s, 3H), 4.01 (s, 3H), 3.23–3.01 (m, 4H), 2.42 (s, 3H), 1.89–1.84 (br.-d, 2H), 1.35 (t, 3H, J=7.0 Hz).

IR (KBr tab.) (cm$^{-1}$): 1698, 1658, 1504, 1429, 1343.

Melting Point (DMF-water): 125°–128° C.

Example 17

3-[1-(6,7-Dimethoxy-4-quinazolinyl)-4-piperidinyl]-1,2,3,4-tetrahydro-6-methyl-2,4-dioxo-1-propyl-quinazoline (Compound 17)

The procedure similar to that described in Example 15 was repeated, except that 1.067 g (2.86 mmol) of 3-(1-ethoxycarbonyl-4-piperidinyl)-1,2,3,4-tetrahydro-6-methyl-2,4-dioxo-1-propyl-quinazoline (Compound c) obtained in Reference Example 9 was used in place of Compound a, whereby 717.2 mg of crude 1,2,3,4-tetrahydro-6-methyl-2,4-dioxo-3-(4-piperidinyl)-1-propylquinazoline hydrobromide was obtained. The product (300.0 mg) was treated in the similar manner as in Example 15 to give 322.6 mg (yield: 56.6%) of Compound 17 as white crystals.

$^1$H-NMR (CDCl$_3$) δ (ppm): 8.68 (s, 1H), 8.02 (d, 1H, J=1.5 Hz), 7.47 (dd, 1H, J=8.4, 1.5 Hz), 7.26 (s, 1H), 7.19 (s, 1H), 7.06 (d, 1H, J=8.4 Hz), 5.32–5.23 (m, 1H), 4.36–4.32 (br.-d, 2H), 4.08–3.97 (dist.-t, 2H), 4.03 (s, 3H), 4.01 (s, 3H), 3.23–3.00 (m, 4H), 2.41 (s, 3H), 1.87–1.75 (m, 4H), 1.04 (t, 3H, J=7.5 Hz).

IR (KBr tab.) (cm$^{-1}$): 1699, 1657, 1505, 1428, 1344.

Melting Point (DMF-water): 113°–116° C.

Example 18

8-Chloro-3-[1-(6,7-dimethoxy-4-quinazolinyl)-4-piperidinyl]-1,2,3,4-tetrahydro-1-methyl-6-nitro-2,4-dioxoquinazoline (Compound 18)

The procedure similar to that described in Example 15 was repeated, except that 510.0 mg (1.24 mmol) of 8-chloro-3-(1-ethoxycarbonyl-4-piperidinyl)-1,2,3,4-tetrahydro-1-methyl-6-nitro-2,4-dioxoquinazoline (Compound d) obtained in Reference Example 10 was used in place of Compound a, whereby 287.8 mg of crude 8-chloro-1,2,3,4-tetrahydro-1-methyl-6-nitro-2,4-dioxo-3-(4-piperidinyl)-quinazoline hydrobromide was obtained. The product (107.2 mg) was treated in the similar manner as in Example 15 to give 74.8 mg (yield: 30.3%) of Compound 18 as pale yellow crystals.

$^1$H-NMR (CDCl$_3$) δ (ppm): 8.97 (d, 1H, J=3.0 Hz), 8.69 (s, 1H), 8.53 (d, 1H, J=3.0 Hz), 7.32 (s, 1H), 7.16 (s, 1H), 5.12–5.11 (m, 1H), 4.41–4.36 (br.-d, 2H), 4.04 (s, 3H), 4.01 (s, 3H), 3.89 (s, 3H), 3.26–3.18 (br.-t, 2H), 3.06–2.91 (m, 2H), 1.89–1.86 (br.-d, 2H).

IR (KBr tab.) (cm$^{-1}$): 1718, 1668, 1607, 1477, 1347.

Melting Point (ethyl acetate-ether): 277°–279° C.

Example 19

1-Cyclopropylmethyl-3-[1-(6,7-dimethoxy-4-quinazolinyl)-4-piperidinyl]-1,2,3,4-tetrahydro-6-nitro-2,4-dioxoquinazoline (Compound 26)

The procedure similar to that described in Example 1 was repeated, except that 300 mg (0.63 mmol) of Compound 24 was used and cyclopropylmethyl bromide was used in place of methyl iodide. As a result, 89 mg (yield: 27%) of Compound 26 was obtained as pale yellow crystals.

$^1$H-NMR (CDCl$_3$) δ (ppm): 9.09 (d, 1H, J=2.5 Hz), 8.64 (s, 1H), 8.53 (dd, 1H, J=9.0, 2.5 Hz), 7.44 (d, 1H, J=9.0 Hz), 7.26 (s, 1H), 7.16 (s, 1H), 5.35–5.25 (m, 1H), 4.50–4.45 (br.-d, 2H), 4.11 (d, 2H, J=7.0 Hz), 4.08 and 4.01 (s for each, 3H), 3.39–3.29 (br.-t, 2H), 3.06–2.91 (m, 2H), 1.95–1.89 (br.-d, 2H), 1.24–1.18 (m, 1H), 0.66–0.51 (m, 4H).

IR (KBr tab.) (cm$^{-1}$): 1713, 1666, 1615, 1511, 1499, 1463, 1336.

Melting Point (ethyl acetate-ether): 193°–195° C.

Example 20

6-Chloro-3-[1-(6,7-dimethoxy-4-quinazolinyl)-4-piperidinyl]-1,2,3,4-tetrahydro-1-methyl-2,4-dioxo-quinazoline (Compound 40)

The procedure similar to that described in Example 1 was repeated, except that 300 mg (0.64 mmol) of 6-chloro-3-[1-(6,7-dimethoxy-4-quinazolinyl)-4-piperidinyl]-1,2,3,4-tetrahydro-2,4-dioxoquinazoline (Compound h) obtained according to the method described in the literature [Chem. Pharm. Bull., 38, 1591–1595 (1990)] was used in place of Compound 24. As a result, 199.2 mg (yield: 65%) of Compound 40 was obtained as white crystals.

$^1$H-NMR (CDCl$_3$) δ (ppm): 8.68 (s, 1H), 8.18 (d, 1H, J=1.5 Hz), 7.63 (dd, 1H, J=9.0, 1.5 Hz), 7.32 (s, 1H), 7.18 (s, 1H), 7.15 (d, 1H, J=9.0 Hz), 5.33–5.21 (m, 1H), 4.40–4.35 (br.-d, 2H), 4.04, 4.01, and 3.59 (s for each, 3H), 3.25–3.16 (br.-t, 2H), 3.10–3.01 (m, 2H), 1.88–1.87 (br.-d, 2H).

IR (KBr tab.) (cm$^{-1}$): 1700, 1650, 1577, 1463, 1342.

Melting Point (ether): 260°–261° C.

Example 21

6-Chloro-3-[1-(6,7-dimethoxy-4-quinazolinyl)-4-piperidinyl]-1-ethyl-1,2,3,4-tetrahydro-2,4-dioxo-quinazoline (Compound 41)

The procedure similar to that described in Example 1 was repeated, except that 300 mg (0.64 mmol) of Compound h was used in place of Compound 24 and ethyl iodide was used in place of methyl iodide. As a result, 145.9 mg (yield: 45%) of Compound 41 was obtained as white crystals.

$^1$H-NMR (CDCl$_3$) δ (ppm): 8.68 (s, 1H), 8.19 (d, 1H, J=1.5 Hz), 7.61 (dd, 1H, J=9.0, 1.5 Hz), 7.33 (s, 1H), 7.18 (s, 1H), 7.14 (d, 1H, J=9.0 Hz), 5.32–5.21 (m, 1H), 4.41–4.36 (br.-d, 2H), 4.17 (q, 2H, J=7.5 Hz), 4.04 and 4.01 (s for each, 3H), 3.24–3.10 (br.-t, 2H), 3.10–2.98 (m, 2H), 1.88–1.82 (br.-d, 2H), 1.35 (t, 3H, J=7.5 Hz).

IR (KBr tab.) (cm$^{-1}$): 1709, 1661, 1575, 1454.

Melting Point (ether): 237°–238° C.

Example 22

6-Chloro-3-[1-(6,7-dimethoxy-4-quinazolinyl)-4-piperidinyl]-1,2,3,4-tetrahydro-2,4-dioxo-1-propyl-quinazoline (Compound 42)

The procedure similar to that described in Example 1 was repeated, except that 300 mg (0.64 mmol) of Compound h was used in place of Compound 24 and propyl iodide was used in place of methyl iodide. As a result, 200.9 mg (yield: 63%) of Compound 42 was obtained as white crystals.

$^1$H-NMR (CDCl$_3$) δ (ppm): 8.68 (s, 1H), 8.18 (d, 1H, J=1.5 Hz), 7.61 (dd, 1H, J=9.0, 1.5 Hz), 7.30 (s, 1H), 7.18 (s, 1H), 7.11 (d, 1H, J=9.0 Hz), 5.32–5.21 (m, 1H), 4.39–4.35 (br.-d, 2H), 4.08–3.95 (m, 2H), 4.04 and 4.01 (s for each, 3H), 3.24–3.10 (br.-t, 2H), 3.10–2.98 (m, 2H), 1.87–1.72 (m, 4H), 1.04 (t, 3H, J=7.4 Hz).

IR (KBr tab.) (cm$^{-1}$): 1704, 1661, 1578, 1451.

Melting Point (ether): 204°–205° C.

Example 23

1-Butyl-3-[1-(6,7-dimethoxy-4-quinazolinyl)-4-piperidinyl]-1,2,3,4-tetrahydro-6-methyl-2,4-dioxo-quinazoline (Compound 51)

The procedure similar to that described in Example 1 was repeated, except that 300 mg (0.67 mmol) of 3-[1-(6,7-dimethoxy-4-quinazolinyl)-4-piperidinyl]-1,2,3,4-tetrahydro-6-methyl-2,4-dioxoquinazoline (Compound 22) obtained in Reference Example 4 was used in place of Compound 24 and butyl iodide was used in place of methyl iodide. As a result, 253.6 mg (yield: 75%) of Compound 51 was obtained as white crystals.

$^1$H-NMR (CDCl$_3$) δ (ppm): 8.67 (s, 1H), 8.02 (d, 1H, J=2.0 Hz), 7.48 (dd, 1H, J=8.5, 2.0 Hz), 7.33 (s, 1H), 7.19 (s, 1H), 7.08 (d, 1H, J=8.5 Hz), 5.34–5.25 (m, 1H), 4.42–4.37 (br.-d, 2H), 4.08–4.04 (dist.-t, 2H), 4.04 and 4.01 (s for each, 3H), 3.26–3.17 (br.-t, 2H), 3.12–3.00 (m, 2H), 2.41 (s, 3H), 1.88–1.84 (br.-d, 2H), 1.77–1.66 (m, 2H), 1.00 (t, 3H, J=7.3 Hz).

IR (KBr tab. ) (cm$^{-1}$): 1700, 1656, 1509, 1314, 1211.

Melting Point (ethyl acetate-ether): 185°–186° C.

Example 24

3-[1-(6,7-Dimethoxy-4-quinazolinyl)-4-piperidinyl]-1,2,3,4-tetrahydro-6-methyl-2,4-dioxo-1-pentyl-quinazoline (Compound 52)

The procedure similar to that described in Example 1 was repeated, except that 300 mg (0.67 mmol) of Compound 22 was used in place of Compound 24 and pentyl iodide was used in place of methyl iodide, whereby a free base of Compound 52 was obtained as an oily substance. The product was dissolved in 10 ml of diethyl ether, and 10 ml of a saturated solution of hydrogen chloride in ethyl acetate was added dropwise to the solution. The precipitated crystals were collected by filtration, washed with diethyl ether, and dried to give 204.7 mg (yield: 55%) of the hydrochloride of Compound 52 as white crystals.

$^1$H-NMR (DMSO-d$_6$) δ (ppm): 8.82 (s, 1H), 7.85 (s, 1H), 7.59 (d, 1H, J=8.5 Hz), 7.37 (s, 2H), 7.36 (d, 1H, J=8.5 Hz), 5.40–5.20 (m, 1H), 4.83–4.77 (br.-d, 2H), 4.06–4.04 (m, 2H), 4.00 and 3.96 (s for each, 3H), 3.71–3.63 (br.-t, 2H), 2.74–2.70 (m, 2H), 2.36 (s, 3H), 1.93–1.89 (br.-d, 2H), 1.65–1.45 (m, 2H), 1.40–1.25 (m, 4H), 0.89 (dist.-t, 3H).

IR (KBr tab. ) (cm$^{-1}$): 1692, 1643, 1511, 1313, 1217.

Melting Point (ether): 240°–243° C.

Example 25

3-[1-(6,7-Dimethoxy-4-quinazolinyl)-4-piperidinyl]-1,2,3,4-tetrahydro-6-methyl-2,4-dioxo-1-(2-propenyl)-quinazoline (Compound 53)

The procedure similar to that described in Example 1 was repeated, except that 300 mg (0.67 mmol) of Compound 22 was used in place of Compound 24 and allyl bromide was used in place of methyl iodide. As a result, 187.8 mg (yield: 58%) of Compound 53 was obtained as white crystals.

$^1$H-NMR (CDCl$_3$) δ (ppm): 8.67 (s, 1H), 8.02 (d, 1H, J=2.0 Hz), 7.45 (dd, 1H, J=8.5, 2.0 Hz), 7.31 (s, 1H), 7.19 (s, 1H), 7.06 (d, 1H, J=8.5 Hz), 5.97 (ddt, 1H, J=17.0, 10.0, 5.0 Hz), 5.31–5.17 (m, 3H), 4.75 (d, 2H, J=5.0 Hz), 4.39–4.35 (br.-d, 2H), 4.04 and 4.01 (s for each, 3H), 3.25–2.99 (m, 4H), 2.41 (s, 3H), 1.89–1.85 (br.-d, 2H).

IR (KBr tab.) (cm$^{-1}$): 1699, 1656, 1505, 1452, 1335, 1214.

Melting Point (ether): 178°–181° C.

Example 26

3-[1-(6,7-Dimethoxy-4-quinazolinyl)-4-piperidinyl]-1,2,3,4-tetrahydro-1,5-dimethyl-2,4-dioxoquinazoline (Compound 57)

The procedure similar to that described in Example 1 was repeated, except that 300 mg (0.67 mmol) of 3-[1-(6,7-dimethoxy-4-quinazolinyl)-4-piperidinyl]-1,2,3,4-tetrahydro-5-methyl-2,4-dioxoquinazoline (Compound 100) obtained in Reference Example 11 was used in place of Compound 24. As a result, 226.8 mg (yield: 73%) of Compound 57 was obtained as white crystals.

$^1$H-NMR (CDCl$_3$) δ (ppm): 8.68 (s, 1H), 7.51 (dd, 1H, J=8.0, 7.0 Hz), 7.29 and 7.25 (s for each, 1H), 7.07–7.04 (m, 2H), 5.32–5.23 (m, 1H), 4.39–4.34 (br.-d, 2H), 4.04, 4.01, and 3.58 (s for each, 3H), 3.23–3.02 (m, 4H), 2.81 (s, 3H), 1.88–1.83 (br.-d, 2H).

IR (KBr tab.) (cm$^{-1}$): 1696, 1654, 1481, 1343, 1212.

Melting Point (ethyl acetate-ether): 230°–231° C.

Example 27

3-[1-(6,7-Dimethoxy-4-quinazolinyl)-4-piperidinyl]-1,2,3,4-tetrahydro-5-methyl-2,4-dioxo-1-propyl-quinazoline (Compound 58)

The procedure similar to that described in Example 1 was repeated, except that 300 mg (0.67 mmol) of Compound 100 was used in place of Compound 24 and propyl iodide was used in place of methyl iodide. As a result, 238.8 mg (yield: 73%) of Compound 58 was obtained as white crystals.

$^1$H-NMR (CDCl$_3$) δ (ppm): 8.68 (s, 1H), 7.49 (dd, 1H, J=8.0, 7.0 Hz), 7.26 and 7.19 (s for each, 1H), 7.05–7.02 (m, 2H), 5.30–5.21 (m, 1H), 4.38–4.33 (br.-d, 2H), 4.06 (dist.-t, 2H), 4.03 and 4.02 (s for each, 3H), 3.22–3.03 (m, 4H), 2.82 (s, 3H), 1.87–1.73 (m, 4H), 1.04 (t, 3H, J=7.5 Hz).

IR (KBr tab.) (cm$^{-1}$): 1675, 1602, 1506, 1452, 1429, 1212.

Melting Point (ethyl acetate-ether): 163°–164° C.

Example 28

3-[1-(6,7-Dimethoxy-4-quinazolinyl)-4-piperidinyl]-1,2,3,4-tetrahydro-1,8-dimethyl-2,4-dioxoquinazoline (Compound 59)

The procedure similar to that described in Example 1 was repeated, except that 300 mg (0.67 mmol) of 3-[1-(6,7-dimethoxy-4-quinazolinyl)-4-piperidinyl]-1,2,3,4-tetrahydro-8-methyl-2,4-dioxoquinazoline (Compound 101) obtained in Reference Example 12 was used in place of Compound 24. As a result, 185.2 mg (yield: 61%) of Compound 59 was obtained as white crystals.

$^1$H-NMR (CDCl$_3$) δ (ppm): 8.68 (s, 1H), 8.06 (dd, 1H, J=8.0, 1.5 Hz), 7.46 (dd, 1H, J=7.0, 1.5 Hz), 7.26 and 7.20 (s for each, 1H), 7.17 (dd, 1H, J=8.0, 7.0 Hz), 5.19–5.12 (m, 1H), 4.36–4.31 (br.-d, 2H), 4.03, 4.01, and 3.67 (s for each, 3H), 3.22–3.01 (m, 4H), 2.61 (s, 3H), 1.89–1.85 (br.-d, 2H).

IR (KBr tab.) (cm$^{-1}$): 1697, 1649, 1508, 1462, 1343.

Melting Point (ether): 238°–246° C.

Example 29

3-[1-(6,7-Dimethoxy-4-quinazolinyl)-4-piperidinyl]-1,2,3,4-tetrahydro-1-isobutyl-6-nitro-2,4-dioxoquinazoline (Compound 25)

The procedure similar to that described in Example 15 was repeated, except that 160.1 mg (0.38 mmol) of 3-(1-ethoxycarbonyl-4-piperidinyl)-1,2,3,4-tetrahydro-1-isobutyl-6-nitro-2,4-dioxoquinazoline (Compound i) was used in place of Compound a, whereby 177.8 mg of crude 1,2,3,4-tetrahydro-1-isobutyl-6-nitro-2,4-dioxo-3-(4-piperidinyl)quinazoline hydrobromide was obtained. The product (170.0 mg) was treated in the similar manner as in Example 15 to give 69.6 mg (yield: 36%) of Compound 25 as pale yellow crystals.

$^1$H-NMR (CDCl$_3$) δ (ppm): 9.09 (d, 1H, J=2.5 Hz), 8.68 (s, 1H), 8.48 (dd, 1H, J=9.0, 2.5 Hz), 7.39 (s, 1H), 7.27 (d, 1H, J=9.0 Hz), 7.17 (s, 1H), 5.34–5.24 (m, 1H), 4.46–4.42 (br.-d, 2H), 4.05 and 4.01 (s for each, 3H), 4.02 (d, 2H, J=8.0 Hz), 3.33–3.21 (br.-t, 2H), 3.07–2.96 (m, 2H), 2.21–2.15 (m, 1H), 1.90–1.85 (br.-d, 2H), 1.03 (d, 6H, J=7.0 Hz).

IR (KBr tab.) (cm$^{-1}$): 1713, 1665, 1613, 1502, 1429, 1332.

Melting Point (ethyl acetate-ether): 146°–147° C.

Example 30

1-Cyclohexylmethyl-3-[1-(6,7-dimethoxy-4-quinazolinyl)-4-piperidinyl]-1,2,3,4-tetrahydro-6-nitro-2,4-dioxo-quinazoline (Compound 27)

The procedure similar to that described in Example 15 was repeated, except that 208.0 mg (0.45 mmol) of 1-cyclohexylmethyl-3-(1-ethoxycarbonyl-4-piperidinyl)-1,2,3,4-tetrahydro-6-nitro-2,4-dioxoquinazoline (Compound j) was used in place of Compound a, whereby 269.3 mg of crude 1-cyclohexylmethyl-1,2,3,4-tetrahydro-6-nitro-2,4-dioxo-3-(4-piperidinyl)quinazoline hydrobromide was obtained. The product (250 mg) was treated in the similar manner as in Example 15 to give 79.9 mg (yield: 34%) of Compound 27 as pale yellow crystals.

$^1$H-NMR (CDCl$_3$) δ (ppm): 9.09 (d, 1H, J=3.0 Hz), 8.68 (s, 1H), 8.49 (dd, 1H, J=9.0, 3.0 Hz), 7.39 (s, 1H), 7.28 (d, 1H, J=9.0 Hz), 7.17 (s, 1H), 5.33–5.24 (m, 1H), 4.46–4.41 (br.-d, 2H), 4.05 and 4.02 (s for each, 3H), 4.02 (d, 2H, J=7.0 Hz), 3.30–3.20 (br.-t, 2H), 3.07–2.88 (m, 2H), 1.89–1.70 (m, 8H), 1.23–1.18 (m, 5H).

IR (KBr tab.) (cm$^{-1}$): 1667, 1615, 1502, 1330.

Melting Point (ethyl acetate-ether): 135°–136° C.

Example 31

3-[1-(6,7-Dimethoxy-4-quinazolinyl)-4-piperidinyl]-1-(2-dimethylaminoethyl)-1,2,3,4-tetrahydro-6-nitro-2,4-dioxoquinazoline (Compound 28)

The procedure similar to that described in Example 15 was repeated, except that 460.0 mg (1.10 mmol) of 1-(2-dimethylaminoethyl)-3-(1-ethoxycarbonyl-4-piperidinyl)-1,2,3,4-tetrahydro-6-nitro-2,4-dioxoquinazoline (Compound k) was used in place of Compound a, whereby 348.1 mg of crude 1-(2-dimethylaminoethyl)-1,2,3,4-tetrahydro-6-nitro-2,4-dioxo-3-(4-piperidinyl)quinazoline hydrobromide was obtained. The product (200 mg) was treated in the similar manner as in Example 15 to give 71.7 mg (yield: 21%) of Compound 28 as pale yellow crystals.

¹H-NMR (CDCl₃) δ (ppm): 9.09 (d, 1H, J=2.6 Hz), 8.70 (s, 1H), 8.50 (dd, 1H, J=9.5, 2.6 Hz), 7.41 (d, 1H, J=9.5 Hz), 7.27 (s, 1H), 7.18 (s, 1H), 5.30–5.15 (m, 1H), 4.40–4.25 (m, 4H), 4.04 and 4.02 (s for each, 3H), 3.25–3.15 (br.-t, 2H), 3.15–2.93 (m, 2H), 2.70–2.60 (br.-t, 2H), 2.37 (s, 6H), 1.88–1.82 (br.-d, 2H).

IR (KBr tab.) (cm⁻¹): 1714, 1667, 1617, 1504, 1453, 1333.

Melting Point (ethyl acetate-ether): 113°–114° C.

Example 32

8-Chloro-3-[1-(6,7-dimethoxy-4-quinazolinyl)-4-piperidinyl]-1-ethyl-1,2,3,4-tetrahydro-2,4-dioxoquinazoline (Compound 35)

The procedure similar to that described in Example 15 was repeated, except that 388.0 mg (1.02 mmol) of 8-chloro-3-(1-ethoxycarbonyl-4-piperidinyl)-1-ethyl-1,2,3,4-tetrahydro-2,4-dioxoquinazoline (Compound l) was used in place of Compound a, whereby 301.8 mg of crude 8-chloro-1-ethyl-1,2,3,4-tetrahydro-2,4-dioxo-3-(4-piperidinyl)-quinazoline hydrobromide was obtained. The product (300.0 mg) was treated in the similar manner as in Example 15 to give 158.6 mg (yield: 32%) of Compound 35 as white crystals.

¹H-NMR (CDCl₃) δ (ppm): 8.69 (s, 1H), 8.18 (dd, 1H, J=8.5, 1.5 Hz), 7.69 (dd, 1H, J=8.5, 1.5 Hz), 7.27 (s, 1H), 7.18 (s, 1H), 7.18 (dd, 1H, J=8.5, 8.5 Hz), 5.19–5.09 (m, 1H), 4.44 (q, 2H, J=7.0 Hz), 4.37–4.32 (br.-d, 2H), 4.04 and 4.02 (s for each, 3H), 3.22–3.13 (br.-t, 2H), 3.09–3.00 (m, 2H), 1.89–1.85 (br.-d, 2H), 1.50 (t, 3H, J=7.0 Hz).

IR (KBr tab.) (cm⁻¹): 1709, 1656, 1449, 1335.

Melting Point (ethyl acetate-ether): 211°–212° C.

Example 33

8-Chloro-3-[1-(6,7-dimethoxy-4-quinazolinyl)-4-piperidinyl]-1-ethyl-1,2,3,4-tetrahydro-6-nitro-2,4-dioxoquinazoline (Compound 37)

The procedure similar to that described in Example 15 was repeated, except that 300.0 mg (0.71 mmol) of 8-chloro-3-(1-ethoxycarbonyl-4-piperidinyl)-1-ethyl-1,2,3,4-tetrahydro-6-nitro-2,4-dioxoquinazoline (Compound m) was used in place of Compound a, whereby 219.4 mg of crude 8-chloro-1-ethyl-1,2,3,4-tetrahydro-6-nitro-2,4-dioxo-3-(4-piperidinyl)quinazoline hydrobromide was obtained. The product (200.0 mg) was treated in the similar manner as in Example 15 to give 163.3 mg (yield: 47%) of Compound 37 as pale yellow crystals.

¹H-NMR (CDCl₃) δ (ppm): 9.01 (d, 1H, J=2.6 Hz), 8.70 (s, 1H), 8.54 (d, 1H, J=2.6 Hz), 7.28 (s, 1H), 7.17 (s, 1H), 5.20–5.08 (m, 1H), 4.51 (q, 2H, J=6.6 Hz), 4.37–4.33 (br.-d, 2H), 4.04 and 4.02 (s for each, 3H), 3.24–3.15 (br.-t, 2H), 3.06–2.97 (m, 2H), 1.90–1.84 (br.-d, 2H), 1.54 (t, 3H, J=6.6 Hz).

IR (KBr tab.) (cm⁻¹): 1718, 1666, 1482, 1430, 1338.

Melting Point (ethyl acetate-ether): 254°–255° C.

Example 34

8-Chloro-3-[1-(6,7-dimethoxy-4-quinazolinyl)-4-piperidinyl]-1,2,3,4-tetrahydro-6-nitro-2,4-dioxo-1-propylquinazoline (Compound 38)

The procedure similar to that described in Example 15 was repeated, except that 300.0 mg (0.68 mmol) of 8-chloro-3-(1-ethoxycarbonyl-4-piperidinyl)-1,2,3,4-tetrahydro-6-nitro-2,4-dioxo-1-propylquinazoline (Compound n) was used in place of Compound a, whereby 119.4 mg of crude 8-chloro-1,2,3,4-tetrahydro-6-nitro-2,4-dioxo-3-(4-piperidinyl)-1-propylquinazoline hydrobromide was obtained. The product (110.0 mg) was treated in the similar manner as in Example 15 to give 45.1 mg (yield: 13%) of Compound 38 as pale yellow crystals.

¹H-NMR (CDCl₃) δ (ppm): 9.01 (d, 1H, J=2.6 Hz), 8.68 (s, 1H), 8.53 (d, 1H, J=2.6 Hz), 7.35 (s, 1H), 7.17 (s, 1H), 5.20–5.10 (m, 1H), 4.44–4.38 (m, 4H), 4.05 and 4.02 (s for each, 3H), 3.30–3.15 (br.-t, 2H), 3.08–2.90 (m, 2H), 1.89–1.71 (m, 4H), 0.98 (t, 3H, J=7.5 Hz).

IR (KBr tab.) (cm⁻¹): 1669, 1606, 1453, 1338.

Melting Point (ethyl acetate-ether): 209°–210° C.

Example 35

6-Chloro-3-[1-(6,7-dimethoxy-4-quinazolinyl)-4-piperidinyl]-1-ethyl-1,2,3,4-tetrahydro-8-nitro-2,4-dioxoquinazoline (Compound 43)

The procedure similar to that described in Example 15 was repeated, except that 600.0 mg (1.53 mmol) of 6-chloro-3-(1-ethoxycarbonyl-4-piperidinyl)-1-ethyl-1,2,3,4-tetrahydro-8-nitro-2,4-dioxoquinazoline (Compound o) was used in place of Compound a, whereby 480.3 mg of crude 6-chloro-1-ethyl-1,2,3,4-tetrahydro-8-nitro-2,4-dioxo-3-(4-piperidinyl)-quinazoline hydrobromide was obtained. The product (480.0 mg) was treated in the similar manner as in Example 15 to give 396.8 mg (yield: 48%) of Compound 43 as pale yellow crystals.

¹H-NMR (CDCl₃) δ (ppm): 8.69 (s, 1H), 8.38 (d, 1H, J=2.5 Hz), 7.86 (d, 1H, J=2.5 Hz), 7.31 (s, 1H), 7.17 (s, 1H), 5.18–5.12 (m, 1H), 4.40–4.36 (br.-d, 2H), 4.04 and 4.01 (s for each, 3H), 3.88 (q, 2H, J=7.0 Hz), 3.25–3.16 (br.-t, 2H), 3.06–2.91 (m, 2H), 1.91–1.87 (br.-d, 2H), 1.28 (t, 3H, J=7.0 Hz).

IR (KBr tab.) (cm⁻¹): 1713, 1666, 1575, 1504, 1476, 1431, 1343.

Melting Point (ether): 254°–256° C.

Example 36

6-Chloro-3-[1-(6,7-dimethoxy-4-quinazolinyl)-4-piperidinyl]-1,2,3,4-tetrahydro-8-nitro-2,4-dioxo-1-propylquinazoline (Compound 44)

The procedure similar to that described in Example 15 was repeated, except that 600.0 mg (1.41 mmol) of 6-chloro-3-(1-ethoxycarbonyl-4-piperidinyl)-1,2,3,4-tetrahydro-8-nitro-2,4-dioxo-1-propylquinazoline (Compound p) was used in place of Compound a, whereby 415.1 mg of crude 6-chloro-1,2,3,4-tetrahydro-8-nitro-2,4-dioxo-3-(4-piperidinyl)-1-propylquinazoline hydrobromide was obtained. The product (410.0 mg) was treated in the similar manner as in Example 15 to give 174.5 mg (yield: 23%) of Compound 44 as pale yellow crystals.

¹H-NMR (CDCl₃) δ (ppm): 8.69 (s, 1H), 8.38 (d, 1H, J=2.5 Hz), 7.86 (d, 1H, J=2.5 Hz), 7.35 (s, 1H), 7.16 (s, 1H), 5.20–5.10 (m, 1H), 4.42–4.38 (br.-d, 2H), 4.05 and 4.01 (s for each, 3H), 3.85–3.79 (dist.-t, 2H), 3.26–3.17 (br.-t, 2H), 3.06–2.92 (m, 2H), 1.91–1.87 (br.-d, 2H), 1.70–1.56 (m, 2H), 0.83 (t, 3H, J=7.3 Hz).

IR (KBr tab.) (cm⁻¹): 1714, 1671, 1476, 1431, 1342.

Melting Point (ethyl acetate-ether): 255°–257° C.

Example 37

6-Bromo-3-[1-(6,7-dimethoxy-4-quinazolinyl)-4-piperidinyl]-1,2,3,4-tetrahydro-1-methyl-2,4-dioxoquinazoline (Compound 45)

The procedure similar to that described in Example 15 was repeated, except that 397.3 mg (0.97 mmol) of 6-bromo-3-(1-ethoxycarbonyl-4-piperidinyl)-1,2,3,4-tetrahydro-1-methyl-2,4-dioxoquinazoline (Compound q) was used in place of Compound a, whereby 210.0 mg of crude 6-bromo-1,2,3,4-tetrahydro-1-methyl-2,4-dioxo-3-(4-piperidinyl) quinazoline hydrobromide was obtained. The product (203.5 mg) was treated in the similar manner as in Example 15 to give 48.6 mg (yield: 10%) of Compound 45 as white crystals.

$^1$H-NMR (CDCl$_3$) δ (ppm): 8.68 (s, 1H), 8.33 (d, 1H, J=2.0 Hz), 7.76 (dd, 1H, J=9.0, 2.0 Hz), 7.31 (s, 1H), 7.18 (s, 1H), 7.07 (d, 1H, J=9.0 Hz), 5.31–5.23 (m, 1H), 4.40–4.35 (br.-d, 2H), 4.04, 4.01, and 3.58 (s for each, 3H), 3.25–3.16 (br.-t, 2H), 3.10–2.96 (m, 2H), 1.88–1.84 (br.-d, 2H).

IR (KBr tab.) (cm$^{-1}$): 1698, 1655, 1465, 1343.

Melting Point (ether): 258°–260° C.

Example 38

6-Bromo-3-[1-(6,7-dimethoxy-4-quinazolinyl)-4-piperidinyl]-1-ethyl-1,2,3,4-tetrahydro-2,4-dioxoquinazoline (Compound 46)

The procedure similar to that described in Example 15 was repeated, except that 300.0 mg (0.71 mmol) of 6-bromo-3-(1-ethoxycarbonyl-4-piperidinyl)-1-ethyl-1,2,3,4-tetrahydro-2,4-dioxoquinazoline (Compound r) was used in place of Compound a, whereby 131.9 mg of crude 6-bromo-1-ethyl-1,2,3,4-tetrahydro-2,4-dioxo-3-(4-piperidinyl) quinazoline hydrobromide was obtained. The product (130.0 mg) was treated in the similar manner as in Example 15 to give 75.1 mg (yield: 20%) of Compound 46 as white crystals.

$^1$H-NMR (CDCl$_3$) δ (ppm): 8.68 (s, 1H), 8.34 (d, 1H, J=2.5 Hz), 7.75 (dd, 1H, J=8.9, 2.5 Hz), 7.34 (s, 1H), 7.18 (s, 1H), 7.09 (d, 1H, J=8.9 Hz), 5.31–5.24 (m, 1H), 4.42–4.38 (br.-d, 2H), 4.16 (q, 2H, J=7.0 Hz), 4.04 and 4.01 (s for each, 3H), 3.26–3.17 (br.-t, 2H), 3.06–3.01 (m, 2H), 1.88–1.83 (br.-d, 2H), 1.35 (t, 3H, J=7.0 Hz).

IR (KBr tab.) (cm$^{-1}$): 1704, 1659, 1505, 1484, 1451, 1429, 1339.

Melting Point (ethyl acetate-ether): 249°–250° C.

Example 39

6,8-Dibromo-3-[1-(6,7-dimethoxy-4-quinazolinyl)-4-piperidinyl]-1-ethyl-1,2,3,4-tetrahydro-2,4-dioxoquinazoline (Compound 48)

The procedure similar to that described in Example 15 was repeated, except that 180.0 mg (0.43 mmol) of 6,8-dibromo-3-(1-ethoxycarbonyl-4-piperidinyl)-1-ethyl-1,2,3,4-tetrahydro-2,4-dioxoquinazoline (Compound s) was used in place of Compound a, whereby 112.3 mg of crude 6,8-dibromo-1-ethyl-1,2,3,4-tetrahydro-2,4-dioxo-3-(4-piperidinyl)-quinazoline hydrobromide was obtained. The product (95.3 mg) was treated in the similar manner as in Example 15 to give 37.5 mg (yield: 16%) of Compound 48 as white crystals.

$^1$H-NMR (CDCl$_3$) δ (ppm): 8.69 (s, 1H), 8.31 (d, 1H, J=2.5 Hz), 8.03 (d, 1H, J=2.5 Hz), 7.33 (s, 1H), 7.17 (s, 1H), 5.09–5.05 (m, 1H), 4.45 (q, 2H, J=7.0 Hz), 4.44–4.36 (br.-d, 2H), 4.04 and 4.01 (s for each, 3H), 3.24–3.15 (br.-t, 2H), 3.04–2.92 (m, 2H), 1.90–1.85 (br.-d, 2H), 1.47 (t, 3H, J=7.0 Hz).

IR (KBr tab.) (cm$^{-1}$): 1708, 1667, 1504, 1451, 1428, 1332.

Melting Point (ether): 229°–230° C.

Example 40

7-Chloro-3-[1-(6,7-dimethoxy-4-quinazolinyl)-4-piperidinyl]-1-ethyl-1,2,3,4-tetrahydro-6-nitro-2,4-dioxoquinazoline (Compound 36)

The procedure similar to that described in Example 15 was repeated, except that 200.0 mg (0.47 mmol) of 7-chloro-3-(1-ethoxycarbonyl-4-piperidinyl)-1-ethyl-1,2,3,4-tetrahydro-6-nitro-2,4-dioxoquinazoline (Compound t) was used in place of Compound a, whereby 150.6 mg of crude 7-chloro-1-ethyl-1,2,3,4-tetrahydro-6-nitro-2,4-dioxo-3-(4-piperidinyl)-quinazoline hydrobromide was obtained. The product (145.0 mg, 0.31 mmol) was suspended in 10 ml of methanol, and 70 mg (0.31 mmol) of 4-chloro-6,7-dimethoxyquinazoline and 0.11 ml (0.78 mmol) of triethylamine were added thereto, followed by heating under reflux for 1 hour. After the reaction mixture was cooled to room temperature, water was added, and the precipitated crystals were collected by filtration, washed successively with water, methanol, and ether, and dried. Recrystallization of the resulting crude crystals from methanol/water gave 144.6 mg (yield from Compound t: 60%) of Compound 36 as pale yellow crystals.

$^1$H-NMR (CDCl$_3$) δ (ppm): 8.83 (s, 1H), 8.69 (s, 1H), 7.32 (s, 1H), 7.31 (s, 1H), 7.17 (s, 1H), 5.28–5.19 (m, 1H), 4.40–4.35 (br.-d, 2H), 4.19 (q, 1H, J=7.4 Hz), 4.04 and 4.01 (s for each, 3H), 3.26–3.17 (br.-t, 2H), 3.07–2.97 (m, 2H), 1.88–1.84 (br.-d, 2H), 1.40 (t, 3H, J=7.4 Hz).

IR (KBr tab.) (cm$^{-1}$): 1715, 1662, 1610, 1502, 1449, 1335.

Melting Point (methanol-water): 216°–217° C.

Example 41

3-[1-(6,7-Dimethoxy-4-quinazolinyl)-4-piperidinyl]-1,2,3,4-tetrahydro-1,6-dimethyl-2,4-dioxoquinazoline (Compound 50)

The procedure similar to that described in Example 15 was repeated, except that 6.2 g (18.0 mmol) of 3-(1-ethoxycarbonyl-4-piperidinyl)-1,2,3,4-tetrahydro-1,6-dimethyl-2,4-dioxoquinazoline (Compound u) was used in place of Compound a, whereby 6.1 g of crude 1,2,3,4-tetrahydro-1,6-dimethyl-2,4-dioxo-3-(4-piperidinyl) quinazoline hydrobromide (Compound v) was obtained. The product (2.0 g) was treated in the similar manner as in Example 40 to give 2.46 g of crude Compound 50 as white crystals. The crystals were suspended in 100 ml of methanol, and a saturated solution of hydrogen chloride in ethyl acetate was added thereto in excess, followed by stirring at room temperature for 10 minutes. The precipitated crystals were collected by filtration and recrystallized from methanol/water to give 2.2 g (yield from Compound u: 69%) of the hydrochloride of Compound 50 as white crystals.

$^1$H-NMR (CDCl$_3$) δ (ppm): 8.60 (s, 1H), 8.00 (d, 1H, J=1.5 Hz), 7.72 (s, 1H), 7.50 (dd, 1H, J=8.4, 1.5 Hz), 7.17 (s, 1H), 7.10 (d, 1H, J=8.4 Hz), 5.43–5.34 (m, 1H), 4.73–4.68 (br.-d, 2H), 4.09, 4.00, and 3.58 (s for each, 3H), 3.44–3.35 (br.-t, 2H), 3.05–2.99 (m, 2H), 2.42 (s, 3H), 1.95–1.92 (br.-d, 2H).

IR (KBr tab.) (cm$^{-1}$): 1695, 1649, 1508, 1474, 1362.

Example 42

3-[1-(6,7-Dimethoxy-4-quinazolinyl)-4-piperidinyl]-1,2,3,4-tetrahydro-1-isopropyl-6-nitro-2,4-dioxoquinazoline (Compound 31)

The procedure similar to that described in Example 15 was repeated, except that 100.0 mg (0.25 mmol) of 3-(1-ethoxycarbonyl-4-piperidinyl)-1,2,3,4-tetrahydro-1-isopropyl-6-nitro-2,4-dioxoquinazoline (Compound w) was used in place of Compound a, whereby 103.5 mg of crude 1,2,3,4-tetrahydro-1-isopropyl-6-nitro-2,4-dioxo-3-(4-piperidinyl)quinazoline hydrobromide was obtained. The product was treated in the similar manner as in Example 40 to give 44.4 mg (yield: 36%) of Compound 31 as pale yellow crystals.

$^1$H-NMR (CDCl$_3$) δ (ppm): 9.08 (d, 1H, J=2.5 Hz), 8.68 (s, 1H), 8.48 (dd, 1H, J=8.5, 2.5 Hz), 7.47 (d, 1H, J=8.5 Hz), 7.37 (s, 1H), 7.18 (s, 1H), 5.30–5.15 (m, 1H), 5.10–4.95 (m, 1H), 4.45–4.40 (br.-d, 2H), 4.05 and 4.02 (s for each, 3H), 3.28–3.20 (br.-t, 2H), 3.08–2.95 (m, 2H), 1.90–1.86 (br.-d, 2H), 1.65 (d, 6H, J=7.0 Hz).

IR (KBr tab.) (cm$^{-1}$): 1713, 1667, 1612, 1494, 1321.

Melting Point (ethyl acetate-ether): 216°–217° C.

Example 43

1-(sec-Butyl)-3-[1-(6,7-dimethoxy-4-quinazolinyl)-4-piperidinyl]-1,2,3,4-tetrahydro-6-nitro-2,4-dioxoquinazoline (Compound 32)

The procedure similar to that described in Example 42 was repeated, except that 107.0 mg (0.25 mmol) of 1-(sec-butyl)-3-(1-ethoxycarbonyl-4-piperidinyl)-1,2,3,4-tetrahydro-6-nitro-2,4-dioxoquinazoline (Compound x) was used in place of Compound a, whereby 71.2 mg (yield: 53%) of Compound 32 was obtained as pale yellow crystals.

$^1$H-NMR (CDCl$_3$) δ (ppm): 9.09 (d, 1H, J=2.5 Hz), 8.68 (s, 1H), 8.45 (dd, 1H, J=9.5, 2.5 Hz), 7.47 (d, 1H, J=9.5 Hz), 7.36 (s, 1H), 7.18 (s, 1H), 5.30–5.15 (m, 1H), 5.00–4.60 (m, 1H), 4.44–4.39 (br.-d, 2H), 4.04 and 4.02 (s for each, 3H), 3.28–3.19 (br.-t, 2H), 3.07–2.95 (m, 2H), 2.30–2.00 (m, 2H), 1.89–1.85 (br.-d, 2H), 1.62 (d, 3H, J=6.5 Hz), 0.92 (t, 3H, J=7.5 Hz).

IR (KBr tab.) (cm$^{-1}$): 1716, 1671, 1614, 1454, 1330, 1208.

Melting Point (ethyl acetate-ether): 156°–158° C.

Example 44

3-[1-(6,7-Dimethoxy-4-quinazolinyl)-4-piperidinyl]-1-ethyl-1,2,3,4-tetrahydro-6,8-dinitro-2,4-dioxoquinazoline (Compound 39)

The procedure similar to that described in Example 15 was repeated, except that 360.0 mg (0.89 mmol) of 3-(1-ethoxycarbonyl-4-piperidinyl)-1-ethyl-1,2,3,4-tetrahydro-6,8-dinitro-2,4-dioxoquinazoline (Compound y) was used in place of Compound a, whereby 429.3 mg of crude 1-ethyl-1,2,3,4-tetrahydro-6,8-dinitro-2,4-dioxo-3-(4-piperidinyl) quinazoline hydrobromide was obtained. The product (200.0 mg) was treated in the similar manner as in Example 40 to give 71.0 mg (yield: 31%) of Compound 39 as pale yellow crystals.

$^1$H-NMR (CDCl$_3$) δ (ppm): 9.23 (d, 1H, J=2.5 Hz), 8.72 (d, 1H, J=2.5 Hz), 8.69 (s, 1H), 7.40 (s, 1H), 7.16 (s, 1H), 5.23–5.14 (m, 1H), 4.47–4.42 (br. -d, 2H), 4.06 and 4.02 (s for each, 3H), 3.96 (q, 2H, J=7.3 Hz), 3.31–3.22 (br.-t, 2H), 3.03–2.91 (m, 2H), 1.93–1.90 (br.-d, 2H), 1.33 (d, 3H, J=7.3 Hz).

IR (KBr tab.) (cm$^{-1}$): 1674, 1612, 1341.

Melting Point (ethyl acetate-ether): 223°–224° C.

Example 45

6-Bromo-7-chloro-3-[1-(6,7-dimethoxy-4-quinazolinyl)-4-piperidinyl]-1-ethyl-1,2,3,4-tetrahydro-2,4-dioxo-quinazoline (Compound 47)

The procedure similar to that described in Example 15 was repeated, except that 200.0 mg (0.44 mmol) of 6-bromo-7-chloro-3-(1-ethoxycarbonyl-4-piperidinyl)-1-ethyl-1,2,3,4-tetrahydro-2,4-dioxoquinazoline (Compound z) was used in place of Compound a, whereby 90.4 mg of crude 6-bromo-7-chloro-1-ethyl-1,2,3,4-tetrahydro-2,4-dioxo-3-(4-piperidinyl)quinazoline hydrobromide was obtained. The product (85.0 mg) was treated in the similar manner as in Example 40 to give 69.0 mg (yield: 30%) of Compound 47 as white crystals.

$^1$H-NMR (CDCl$_3$) δ (ppm): 8.83 (s, 1H), 8.69 (s, 1H), 7.32 (s, 1H), 7.31 (s, 1H), 7.17 (s, 1H), 5.28–5.19 (m, 1H), 4.40–4.35 (br.-d, 2H), 4.19 (q, 2H, J=7.4 Hz), 4.04 and 4.01 (s for each, 3H), 3.26–3.17 (br.-t, 2H), 3.07–2.97 (m, 2H), 1.88–1.84 (br.-d, 2H), 1.40 (t, 3H, J=7.4 Hz).

IR (KBr tab.) (cm$^{-1}$): 1715, 1662, 1610, 1502, 1449, 1335.

Melting Point (methanol-water): 216°–217° C.

Example 46

7-Chloro-3-[1-(6,7-dimethoxy-4-quinazolinyl)-4-piperidinyl]-1-ethyl-1,2,3,4-tetrahydro-2,4-dioxo-quinazoline (Compound 49)

The procedure similar to that described in Example 15 was repeated, except that 200.0 mg (0.53 mmol) of 7-chloro-3-(1-ethoxycarbonyl-4-piperidinyl)-1-ethyl-1,2,3,4-tetrahydro-2,4-dioxoquinazoline (Compound aa) was used in place of Compound a, whereby 178.3 mg of crude 7-chloro-1-ethyl-1,2,3,4-tetrahydro-2,4-dioxo-3-(4-piperidinyl)-quinazoline hydrobromide was obtained. The product (170.0 mg) was treated in the similar manner as in Example 40 to give 134.2 mg (yield: 57%) of Compound 49 as white crystals.

$^1$H-NMR (CDCl$_3$) δ (ppm): 8.65 (s, 1H), 8.15 (d, 1H, J=8.5 Hz), 7.25–7.17 (m, 4H), 5.35–5.18 (m, 1H), 4.50–4.35 (br.-d, 2H), 4.13 (q, 2H, J=7.0 Hz), 4.06 and 4.00 (s for each, 3H), 3.27–3.23 (br.-t, 2H), 3.03–2.99 (m, 2H), 1.95–1.86 (br.-d, 2H), 1.37 (t, 3H, J=7.0 Hz).

IR (KBr tab.) (cm$^{-1}$): 1712, 1663, 1606, 1465.

Melting Point (isopropyl alcohol): 183°–184° C.

Example 47

3-[1-(6,7-Dimethoxy-4-quinazolinyl)-4-piperidinyl]-6-ethyl-1,2,3,4-tetrahydro-1-methyl-2,4-dioxoquinazoline (Compound 54)

The procedure similar to that described in Example 15 was repeated, except that 250.0 mg (0.73 mmol) of 3-(1-ethoxycarbonyl-4-piperidinyl)-6-ethyl-1,2,3,4-tetrahydro-1-methyl-2,4-dioxoquinazoline (Compound bb) was used in place of Compound a, whereby 270.0 mg of crude 6-ethyl-1,2,3,4-tetrahydro-1-methyl-2,4-dioxo-3-(4-piperidinyl) quinazoline hydrobromide was obtained. The product (260.0 mg) was treated in the similar manner as in Example 40 to give 256.3 mg (yield: 76%) of Compound 54 as white crystals.

$^1$H-NMR (CDCl$_3$) δ (ppm): 8.69 (s, 1H), 8.04 (d, 1H, J=1.5 Hz), 7.52 (dd, 1H, J=8.5, 1.5 Hz), 7.26 (s, 1H), 7.19 (s, 1H), 7.12 (d, 1H, J=8.5 Hz), 5.35–5.15 (m, 1H), 4.35–4.30 (br.-d, 2H), 4.03, 4.01, and 3.59 (s for each, 3H), 3.18–3.05 (m, 14H), 2.72 (q, 2H, J=7.0 Hz), 1.87–1.79 (br.-d, 2H), 1.27 (t, 3H, J=7.0 Hz).

IR (KBr tab.) (cm$^{-1}$): 1700, 1652, 1512, 1506, 1331, 1213.

Melting Point (ethyl acetate): 202°–203° C.

Example 48

3-[1-(6,7-Dimethoxy-4-quinazolinyl)-4-piperidinyl]-1,2,3,4-tetrahydro-1-methyl-2,4-dioxo-6-propyl-quinazoline (Compound 55)

The procedure similar to that described in Example 15 was repeated, except that 84.0 mg (0.23 mmol) of 3-(1-ethoxycarbonyl-4-piperidinyl)-1,2,3,4-tetrahydro-1-methyl-2,4-dioxo-6-propylquinazoline (Compound cc) was used in place of Compound a, whereby 103.0 mg of crude 1,2,3,4-tetrahydro-1-methyl-2,4-dioxo-3-(4-piperidinyl)-6-propylquinazoline hydrobromide was obtained. The product was treated in the similar manner as in Example 40 to give 42.1 mg (yield: 37%) of Compound 55 as white crystals.

$^1$H-NMR (CDCl$_3$) δ (ppm): 8.67 (s, 1H), 8.02 (d, 1H, J=2.0 Hz), 7.50 (dd, 1H, J=8.5, 2.0 Hz), 7.35 (s, 1H), 7.19 (s, 1H), 7.12 (d, 1H, J=8.5 Hz), 5.36–5.27 (m, 1H), 4.43–4.38 (br.-d, 2H), 4.04, 4.01, and 3.58 (s for each, 3H), 3.28–3.18 (br.-t, 2H), 3.12–3.00 (m, 2H), 2.67 (t, 2H, J=7.5 Hz), 1.89–1.85 (br.-d, 2H), 1.67 (sext, 2H, J=7.5 Hz), 0.94 (t, 3H, J=7.5 Hz).

IR (KBr tab.) (cm$^{-1}$): 1696, 1651, 1501, 1338.

Melting Point (ether): 130°–133° C.

Example 49

3-[1-(6,7-Dimethoxy-4-quinazolinyl)-4-piperidinyl]-1,2,3,4-tetrahydro-6-isopropyl-1-methyl-2,4-dioxo-quinazoline (Compound 56)

The procedure similar to that described in Example 15 was repeated, except that 150.0 mg (0.40 mmol) of 3-(1-ethoxycarbonyl-4-piperidinyl)-1,2,3,4-tetrahydro-6-isopropyl-1-methyl-2,4-dioxoquinazoline (Compound dd) was used in place of Compound a, whereby 155.1 mg of crude 1,2,3,4-tetrahydro-6-isopropyl-1-methyl-2,4-dioxo-3-(4-piperidinyl)quinazoline hydrobromide was obtained. The product (150.0 mg) was treated in the similar manner as in Example 40 to give 118.1 mg (yield: 62%) of Compound 56 as white crystals.

$^1$H-NMR (CDCl$_3$) δ (ppm): 8.68 (s, 1H), 8.07 (d, 1H, J=1.5 Hz), 7.55 (dd, 1H, J=8.5, 1.5 Hz), 7.24 (s, 1H), 7.19 (s, 1H), 7.12 (d, 1H, J=8.5 Hz), 5.32–5.24 (m, 1H), 4.33–4.29 (br.-d, 2H), 4.02, 4.00, and 3.58 (s for each, 3H), 3.22–2.94 (m, 5H), 1.86–1.81 (br.-d, 2H), 1.28 (d, 6H, J=7.0 Hz).

IR (KBr tab.) (cm$^{-1}$): 1701, 1657, 1510, 1475, 1426, 1334, 1212.

Melting Point (ethyl acetate-ether): 195°–196° C.

Example 50

6-Acetyl-3-[1-(6,7-dimethoxy-4-quinazolinyl)-4-piperidinyl]-1,2,3,4-tetrahydro-1-methyl-2,4-dioxo-quinazoline (Compound 63)

The procedure similar to that described in Example 15 was repeated, except that 200.0 mg (0.54 mmol) of 6-acetyl-3-(1-ethoxycarbonyl-4-piperidinyl)-1,2,3,4-tetrahydro-1-methyl-2,4-dioxoquinazoline (Compound ee) was used in place of Compound a, whereby 146.2 mg of crude 6-acetyl-1,2,3,4-tetrahydro-1-methyl-2,4-dioxo-3-(4-piperidinyl) quinazoline hydrobromide was obtained. The product (140.0 mg) was treated in the similar manner as in Example 40 to give 163.7 mg (yield: 64%) of Compound 63 as white crystals.

$^1$H-NMR (CDCl$_3$) δ (ppm): 8.76 (d, 1H, J=2.0 Hz), 8.69 (s, 1H), 8.32 (dd, 1H, J=8.5, 2.0 Hz), 7.34 (s, 1H), 7.28 (d, 1H, J=8.5 Hz), 7.18 (s, 1H), 5.35–5.26 (m, 1H), 4.43–4.38 (br.-d, 2H), 4.06, 4.02, and 3.65 (s for each, 3H), 3.28–3.19 (br.-t, 2H), 3.10–2.98 (m, 2H), 2.67 (s, 3H), 1.90–1.86 (br.-d, 2H).

IR (KBr tab.) (cm$^{-1}$): 1700, 1665, 1610, 1500, 1460, 1340, 1235, 831.

Melting Point (methanol-water): 216°–218° C.

Example 51

3-[1-(6,7-Dimethoxy-4-quinazolinyl)-4-piperidinyl]-1-ethyl-1,2,3,4-tetrahydro-6-hydroxy-2,4-dioxoquinazoline (Compound 66)

The procedure similar to that described in Example 15 was repeated, except that 490.0 mg (1.31 mmol) of 3-(1-ethoxycarbonyl-4-piperidinyl)-1-ethyl-1,2,3,4-tetrahydro-6-methoxy-2,4-dioxoquinazoline (Compound ff) was used in place of Compound a, whereby 284.1 mg of crude 1-ethyl-1,2,3,4-tetrahydro-6-hydroxy-2,4-dioxo-3-(4-piperidinyl) quinazoline hydrobromide was obtained. The product (270.0 mg) was treated in the similar manner as in Example 40 to give 203.5 mg (yield: 34%) of Compound 66 as white crystals.

$^1$H-NMR (CDCl$_3$) δ (ppm): 8.67 (s, 1H), 7.78 (d, 1H, J=3.0 Hz), 7.30–7.27 (m, 2H), 7.18 (s, 1H), 7.09 (d, 1H, J=8.5 Hz), 5.27–5.23 (m, 1H), 4.46–4.42 (br.-d, 2H), 4.16 (dist.-q, 2H), 3.99 (s, 6H), 3.29–3.20 (br.-t, 2H), 3.10–2.98 (m, 2H), 1.86–1.82 (br.-d, 2H), 1.35 (dist.-t, 3H).

IR (KBr tab. ) (cm$^{-1}$): 1694, 1648, 1505, 1476.

Melting Point (ether): 290°–291° C. (decomposition)

Example 52

3-[1-(6,7-Dimethoxy-4-quinazolinyl)-4-piperidinyl]-1,2,3,4-tetrahydro-6-hydroxy-2,4-dioxo-1-propyl-quinazoline (Compound 67)

The procedure similar to that described in Example 15 was repeated, except that 265.0 mg (0.68 mmol) of 3-(1-ethoxycarbonyl-4-piperidinyl)-1,2,3,4-tetrahydro-6-methoxy-2,4-dioxo-1-propylquinazoline (Compound gg) was used in place of Compound a, whereby 216.1 mg of crude 1,2,3,4-tetrahydro-6-hydroxy-2,4-dioxo-3-(4-piperidinyl)-1-propylquinazoline hydrobromide was obtained. The product (200.0 mg) was treated in the similar manner as in Example 40 to give 170.5 mg (yield: 55%) of Compound 67 as white crystals.

$^1$H-NMR (CDCl$_3$) δ (ppm): 8.66 (s, 1H), 7.77 (d, 1H, J=3.0 Hz), 7.28–7.25 (m, 2H), 7.17 (s, 1H), 7.07 (d, 1H, J=8.9 Hz), 5.32–5.23 (m, 1H), 4.46–4.42 (br.-d, 2H), 4.04 (dist.-t, 2H), 4.00 (s, 6H), 3.29–3.21 (br.-t, 2H), 3.07–3.01 (m, 2H), 1.86–1.73 (m, 4H), 1.04 (t, 3H, J=7.3 Hz).

IR (KBr tab.) (cm$^{-1}$): 1695, 1646, 1504, 1480, 1343.

Melting Point (ether): 263°–264° C.

Example 53

3-[1-(6,7-Dimethoxy-4-quinazolinyl)-4-piperidinyl]-1,2,3,4-tetrahydro-7-methoxy-1-methyl-2,4-dioxo-quinazoline (Compound 74)

The procedure similar to that described in Example 15 was repeated, except that 750.0 mg (2.08 mmol) of 3-(1- ethoxycarbonyl-4-piperidinyl)-1,2,3,4-tetrahydro-7-methoxy-1-methyl-2,4-dioxoquinazoline (Compound hh) was used in place of Compound a, whereby crude 1,2,3,4-tetrahydro-7-methoxy-1-methyl-2,4-dioxo-3-(4-piperidinyl) quinazoline hydrobromide was obtained. The product was used in the similar manner as in Example 40 to give 193.5 mg (yield: 20%) of Compound 74 as white crystals.

$^1$H-NMR (CDCl$_3$) δ (ppm): 8.69 (s, 1H), 8.15 (d, 1H, J=9.0 Hz), 7.25 (s, 1H), 7.19 (s, 1H), 6.80 (dd, 1H, J=9.0, 2.0 Hz), 6.60 (d, 1H, J=2.0 Hz), 5.33–5.23 (m, 1H), 4.34–4.30 (br.-d, 2H), 4.03, 4.01, 3.93, and 3.57 (s for each, 3H), 3.17–3.03 (m, 4H), 1.87–1.82 (br.-d, 2H).

IR (KBr tab.) (cm$^{-1}$): 1695, 1655, 1620, 1502, 1422, 1365, 1338, 1230.

Melting Point (ethyl acetate-ether): 214°–216° C.

Example 54

3-[1-(6,7-Dimethoxy-4-quinazolinyl)-4-piperidinyl]-1,2,3,4-tetrahydro-7-hydroxy-1-methyl-2,4-dioxo-quinazoline (Compound 68)

The procedure similar to that described in Example 15 was repeated, except that 320.0 mg (0.89 mmol) of Compound hh was used in place of Compound a and the reaction was carried out for 3 hours, whereby a mixture of 1,2,3,4-tetrahydro-7-methoxy-1-methyl-2,4-dioxo-3-(4-piperidinyl)-quinazoline hydrobromide and 1,2,3,4-tetrahydro-7-hydroxy-1-methyl-2,4-dioxo-3-(4-piperidinyl)quinazoline hydrobromide at a ratio of about 1:1 was obtained. This crude product was treated in the similar manner as in Example 40 to give a mixture of Compound 74 and Compound 68. The obtained mixture was purified by silica gel column chromatography (eluent: chloroform/methanol= 100/1) to give 55.6 mg (yield: 13%) of white crystals of Compound 68 as a second eluted component.

$^1$H-NMR (CDCl$_3$) δ (ppm): 8.66 (s, 1H), 8.07 (d, 1H, J=9.0 Hz), 7.23 (s, 1H), 7.18 (s, 1H), 6.77 (dd, 1H, J=9.0, 2.0 Hz), 6.65 (d, 1H, J=2.0 Hz), 5.35–5.26 (m, 1H), 4.47–4.42 (br.-d, 2H), 4.00, 3.99, and 3.51 (s for each, 3H), 3.30–3.21 (br.-t, 2H), 3.08–2.96 (m, 2H), 1.85–1.81 (br.-d, 2H).

IR (KBr tab.) (cm$^{-1}$): 1694, 1653, 1622, 1503, 1426, 1342.

Melting Point (ethyl acetate-ether): 226°–270° C.

Example 55

3-[1-(2-Chloro-6,7-dimethoxy-4-quinazolinyl)-4-piperidinyl]-1-ethyl-1,2,3,4-tetrahydro-6-nitro-2,4-dioxoquinazoline (Compound 79)

The procedure similar to that described in Example 15 was repeated, except that 3.62 g (9.4 mmol) of 3-(1-ethoxycarbonyl-4-piperidinyl)-1-ethyl-1,2,3,4-tetrahydro-6-nitro-2,4-dioxoquinazoline (Compound ii) was used in place of Compound a, whereby 3.20 g of crude 1-ethyl-1,2,3,4-tetrahydro-6-nitro-2,4-dioxo-3-(4-piperidinyl)quinazoline hydrobromide (Compound jj) was obtained. The product (198.0 mg) was treated in the similar manner as in Example 40, except for the use of 2,4-dichloro-6,7-dimethoxyquinazoline in place of 4-chloro-6,7-dimethoxyquinazoline, to give 220.7 mg (yield: 78%) of Compound 79 as pale yellow crystals.

$^1$H-NMR (CDCl$_3$) δ (ppm): 9.09 (d, 1H, J=3.0 Hz), 8.50 (dd, 1H, J=9.0, 3.0 Hz), 7.32 (d, 1H, J=9.0 Hz), 7.24 (s, 1H), 7.13 (s, 1H), 5.33–5.22 (m, 1H), 4.49–4.44 (br.-d, 2H), 4.24 (q, 2H, J=7.0 Hz), 4.01 and 4.00 (s for each, 3H), 3.30–3.21 (br.-t, 2H), 3.03–2.98 (m, 2H), 1.90–1.87 (br.-d, 2H), 1.40 (t, 3H, J=7.0 Hz).

IR (KBr tab.) (cm$^{-1}$): 1715, 1664, 1617, 1501, 1340.

Melting Point (ether): 295°–296° C.

Example 56

3-[1-(6,7-Dimethoxy-2-methyl-4-quinazolinyl)-4-piperidinyl]-1-ethyl-1,2,3,4-tetrahydro-6-nitro-2,4-dioxoquinazoline (Compound 81)

The procedure similar to that described in Example 40 was repeated, except that 198.0 mg of crude 1-ethyl-1,2,3,4-tetrahydro-6-nitro-2,4-dioxo-3-(4-piperidinyl)-quinazoline hydrobromide (Compound jj) obtained in Example 55 was used and 4-chloro-6,7-dimethoxy-2-methylquinazoline was used in place of 4-chloro-6,7-dimethoxyquinazoline. As a result, 114.0 mg (yield from Compound ii: 44%) of Compound 81 was obtained as pale yellow crystals.

$^1$H-NMR (CDCl$_3$) δ (ppm): 9.08 (d, 1H, J=2.5 Hz), 8.50 (dd, 1H, J=9.0, 2.5 Hz), 7.31 (d, 1H, J=9.0 Hz), 7.25 (s, 1H), 7.14 (s, 1H), 5.26–5.21 (m, 1H), 4.45–4.40 (br.-d, 2H), 4.23 (q, 2H, J=7.0 Hz), 4.02 and 3.98 (s for each, 3H), 3.26–3.16 (br.-t, 2H), 3.06–2.98 (m, 2H), 2.70 (s, 3H), 1.89–1.84 (br.-d, 2H), 1.39 (t, 3H, J=7.0 Hz).

IR (KBr tab.) (cm$^{-1}$): 1715, 1663, 1616, 1502, 1328.

Melting Point (ether): 246°–247° C.

Example 57

3-[1-(6,7-Dimethoxy-1,2,3-benzotriazin-4-yl)-4-piperidinyl]-1,2,3,4-tetrahydro-1,6-dimethyl-2,4-dioxo-quinazoline (Compound 75)

The procedure similar to that described in Example 40 was repeated, except that 354.0 mg (1.0 mmol) of 1,2,3,4-tetrahydro-1,6-dimethyl-2,4-dioxo-3-(4-piperidinyl)-quinazoline hydrobromide (Compound v) obtained in Example 41 was used, 4-methanesulfonyl-6,7-dimethoxy-1,2,3-benzotriazine was used in place of 4-chloro-6,7-dimethoxyquinazoline, DMSO was used as a reaction solvent in place of methanol, and the reaction was conducted at room temperature. As a result, 307.6 mg (yield: 67%) of Compound 75 was obtained as white crystals.

$^1$H-NMR (CDCl$_3$) δ (ppm): 7.98 (d, 1H, J=1.5 Hz), 7.55 (s, 1H), 7.56 (dd, 1H, J=7.5, 1.5 Hz), 7.14 (d, 1H, J=7.5 Hz), 7.13 (s, 1H), 5.40–5.25 (m, 1H), 4.51–4.47 (br.-d, 2H), 4.10, 4.07, and 3.58 (s for each, 3H), 3.36–3.27 (br.-t, 2H), 3.09–3.05 (m, 2H), 2.43 (s, 3H), 1.91–1.87 (br.-d, 2H).

IR (KBr tab.) (cm$^{-1}$): 1700, 1656, 1497, 1466, 1428, 1291.

Melting Point (DMF-water): 236°–237° C. (decomposition)

Example 58

3-[1-(4-Chloro-6,7-dimethoxy-1-phthalazinyl)-4-piperidinyl]-1,2,3,4-tetrahydro-1,6-dimethyl-2,4-dioxo-quinazoline (Compound 76)

The procedure similar to that described in Example 15 was repeated, except that 354.0 mg (1.0 mmol) of 1,2,3,4-tetrahydro-1,6-dimethyl-2,4-dioxo-3-(4-piperidinyl)-quinazoline hydrobromide (Compound v) obtained in Example 41 was used, 1,4-dichloro-6,7-dimethoxyphthalazine was used in place of 4-chloro-6,7-dimethoxyquinazoline, and a catalytic amount of potassium iodide was added. As a result, 243.7 mg (yield: 49%) of Compound 76 was obtained as white crystals.

¹H-NMR (CDCl₃) δ (ppm): 8.02 (d, 1H, J=1.5 Hz), 7.49 (dd, 1H, J=8.5, 1.5 Hz), 7.43 (s, 1H), 7.39 (s, 1H), 7.09 (d, 1H, J=8.5 Hz), 5.30–5.25 (m, 1H), 4.09 (s, 6H), 3.94–3.90 (br.-d, 2H), 3.59 (s, 3H), 3.24–3.09 (m, 4H), 2.43 (s, 3H), 1.88–1.85 (br.-d, 2H).

IR (KBr tab.) (cm⁻¹): 1702, 1653, 1649, 1510, 1421, 1315, 1211.

Melting Point (ethyl acetate-ether): 202°–205° C.

Example 59

3-[1-(2-Chloro-6,7-dimethoxy-4-quinazolinyl)-4-piperidinyl]-1,2,3,4-tetrahydro-1,6-dimethyl-2,4-dioxo-quinazoline (Compound 78)

The procedure similar to that described in Example 40 was repeated, except that 354.0 mg (1.0 mmol) of 1,2,3,4-tetrahydro-1,6-dimethyl-2,4-dioxo-3-(4-piperidinyl)-quinazoline hydrobromide (Compound v) obtained in Example 41 was used and 2,4-dichloro-6,7-dimethoxyquinazoline was used in place of 4-chloro-6,7-dimethoxyquinazoline. As a result, 239.2 mg (yield: 48%) of Compound 78 was obtained as white crystals.

¹H-NMR (CDCl₃) δ (ppm): 8.01 (d, 1H, J=1.0 Hz), 7.55 (dd, 1H, J=8.5, 1.0 Hz), 7.26 (s, 1H), 7.14 (s, 1H), 7.10 (d, 1H, J=8.5 Hz), 5.38–5.26 (m, 1H), 4.50–4.45 (br.-d, 2H), 4.01, 3.99, and 3.58 (s for each, 3H), 3.29–3.20 (br.-t, 2H), 3.11–2.96 (m, 2H), 2.42 (s, 3H), 1.90–1.85 (br.-d, 2H).

IR (KBr tab.) (cm⁻¹): 1706, 1655, 1512, 1480, 1218.

Melting Point (ether) 234°–236° C.

Example 60

3-[1-(6,7-Dimethoxy-2-methyl-4-quinazolinyl)-4-piperidinyl]-1,2,3,4-tetrahydro-1,6-dimethyl-2,4-dioxo-quinazoline (Compound 80)

The procedure similar to that described in Example 40 was repeated, except that 354.0 mg (1.0 mmol) of 1,2,3,4-tetrahydro-1,6-dimethyl-2,4-dioxo-3-(4-piperidinyl)-quinazoline hydrobromide (Compound v) obtained in Example 41 was used and 4-chloro-6,7-dimethoxy-2-methylquinazoline was used in place of 4-chloro-6,7-dimethoxyquinazoline. As a result, 53.1 mg (yield: 10%) of Compound 80 was obtained as white crystals.

¹H-NMR (CDCl₃) δ (ppm): 8.01 (d, 1H, J=2.0 Hz), 7.49 (dd, 1H, J=8.5, 2.0 Hz), 7.26 (s, 1H), 7.17 (s, 1H), 7.09 (d, 1H, J=8.5 Hz), 5.32–5.24 (m, 1H), 4.36–4.32 (br.-d, 2H), 4.01, 3.99, and 3.58 (s for each, 3H), 3.21–2.99 (m, 4H), 2.67 and 2.42 (s for each, 3H), 1.87–1.82 (br.-d, 2H).

IR (KBr tab.) (cm⁻¹): 1698, 1658, 1509, 1432, 1242.

Melting Point (ether): 253°–254° C.

Example 61

3-[1-(6,7-Dimethoxy-2-propyl-4-quinazolinyl)-4-piperidinyl]-1,2,3,4-tetrahydro-1,6-dimethyl-2,4-dioxo-quinazoline (Compound 82)

The procedure similar to that described in Example 40 was repeated, except that 354.0 mg (1.0 mmol) of 1,2,3,4-tetrahydro-1,6-dimethyl-2,4-dioxo-3-(4-piperidinyl)-quinazoline hydrobromide (Compound v) obtained in Example 41 was used, 4-chloro-6,7-dimethoxy-2-propylquinazoline was used in place of 4-chloro-6,7-dimethoxyquinazoline, and isopropyl alcohol was used as a reaction solvent in place of methanol. As a result, 174.3 mg (yield: 35%) of Compound 82 was obtained as white crystals.

¹H-NMR (CDCl₃) δ (ppm): 8.02 (d, 1H, J=1.0 Hz), 7.49 (dd, 1H, J=8.0, 1.0 Hz), 7.22 (s, 1H), 7.17 (s, 1H), 7.08 (d, 1H, J=8.0 Hz), 5.31–5.23 (m, 1H), 4.34–4.30 (br.-d, 2H), 4.01, 3.99, and 3.58 (s for each, 3H), 3.20–3.02 (m, 4H), 2.86 (dist.-t, 2H), 2.42 (s, 3H), 1.93–1.81 (br.-d, 2H), 1.24 (t, 3H, J=7.0 Hz).

IR (KBr tab.) (cm⁻¹): 1704, 1659, 1507, 1476, 1435, 1210.

Melting Point (ethyl acetate-ether): 206°–207° C.

Example 62

1,2,3,4-Tetrahydro-3-[1-(2-isopropyl-6,7-dimethoxy-4-quinazolinyl)-4-piperidinyl]-1,6-dimethyl-2,4-dioxo-quinazoline (Compound 83)

The procedure similar to that described in Example 40 was repeated, except that 354.0 mg (1.0 mmol) of 1,2,3,4-tetrahydro-1,6-dimethyl-2,4-dioxo-3-(4-piperidinyl)-quinazoline hydrobromide (Compound v) obtained in Example 41 was used and 4-chloro-2-isopropyl-6,7-dimethoxyquinazoline was used in place of 4-chloro-6,7-dimethoxyquinazoline. As a result, 50.3 mg (yield: 10%) of Compound 83 was obtained as white crystals.

¹H-NMR (CDCl₃) δ (ppm): 8.02 (d, 1H, J=1.5 Hz), 7.49 (dd, 1H, J=8.5, 1.5 Hz), 7.23 (s, 1H), 7.17 (s, 1H), 7.09 (d, 1H, J=8.5 Hz), 5.33–5.23 (m, 1H), 4.36–4.31 (br.-d, 2H), 4.01, 3.99, and 3.57 (s for each, 3H), 3.21–2.98 (m, 5H), 2.42 (s, 3H), 1.84–1.79 (br.-d, 2H), 1.37 (d, 6H, J=6.9 Hz).

IR (KBr tab.) (cm⁻¹): 1698, 1652, 1501, 1421, 1241, 1208.

Melting Point (hexane-ether): 172°–173° C.

Example 63

1,2,3,4-Tetrahydro-3-[1-(6-methoxy-4-quinazolinyl)-4-piperidinyl]-1,6-dimethyl-2,4-dioxoquinazoline (Compound 84)

The procedure similar to that described in Example 57 was repeated, except that 1.06 g (3.0 mmol) of 1,2,3,4-tetrahydro-1,6-dimethyl-2,4-dioxo-3-(4-piperidinyl)-quinazoline hydrobromide (Compound v) obtained in Example 41 was used and 4-chloro-6-methoxyquinazoline was used in place of 4-chloro-6,7-dimethoxy-quinazoline. As a result, 154.4 mg (yield: 12%) of Compound 84 was obtained as white crystals.

¹H-NMR (CDCl₃) δ (ppm): 8.69 (s, 1H), 8.01 (d, 1H, J=2.0 Hz), 7.98 (d, 1H, J=9.0 Hz), 7.49 (dd, 1H, J=8.5, 2.0 Hz), 7.41 (dd, 1H, J=9.0, 2.5 Hz), 7.24 (d, 1H, J=2.5 Hz), 7.08 (d, 1H, J=8.5 Hz), 5.40–5.25 (m, 1H), 4.44–4.40 (br.-d, 2H), 3.93 and 3.57 (s for each, 3H), 3.48–3.04 (m, 4H), 2.41 (s, 3H), 1.89–1.84 (br.-d, 2H).

IR (KBr tab.) (cm⁻¹): 1699, 1655, 1505, 1453, 1331, 1211, 1038.

Melting Point (methanol): 203°–205° C.

Example 64

1,2,3,4-Tetrahydro-3-[1-(7-methoxy-4-quinazolinyl)-4-piperidinyl]-1,6-dimethyl-2,4-dioxoquinazoline (Compound 85)

The procedure similar to that described in Example 57 was repeated, except that 354.0 g (1.0 mmol) of 1,2,3,4-tetrahydro-1,6-dimethyl-2,4-dioxo-3-(4-piperidinyl)-quinazoline hydrobromide (Compound v) obtained in Example 41 was used and 4-chloro-7-methoxyquinazoline was used in place of 4-chloro-6,7-dimethoxyquinazoline. As a result, 96.2 mg (yield: 22%) of Compound 85 was obtained as white crystals.

¹H-NMR (CDCl₃) δ (ppm): 8.67 (s, 1H), 8.01 (d, 1H, J=1.5 Hz), 7.85 (d, 1H, J=9.2 Hz), 7.49 (dd, 1H, J=8.0, 1.5 Hz), 7.28 (d, 1H, J=2.5 Hz), 7.09 (d, 1H, J=8.0 Hz), 7.06 (dd, 1H, J=9.2, 2.5 Hz), 5.37–5.25 (m, 1H), 4.50–4.45 (br.-d, 2H), 3.95 and 3.58 (s for each, 3H), 3.27–3.18 (br.-t, 2H), 3.12–2.96 (m, 2H), 2.42 (s, 3H), 1.88–1.84 (br.-d, 2H).

IR (KBr tab.) (cm⁻¹): 1699, 1654, 1610, 1436, 1333, 1219.

Melting Point (ethyl acetate-ether): 232°–233° C.

Example 65

1,2,3,4-Tetrahydro-1,6-dimethyl-2,4-dioxo-3-[1-(6,7, 8-trimethoxy-4-quinazolinyl)-4-piperidinyl] quinazoline (Compound 86)

The procedure similar to that described in Example 57 was repeated, except that 1.06 g (3.0 mmol) of 1,2,3,4-tetrahydro-1,6-dimethyl-2,4-dioxo-3-(4-piperidinyl)-quinazoline hydrobromide (Compound v) obtained in Example 41 was used and 4-chloro-6,7,8-trimethoxyquinazoline was used in place of 4-chloro-6,7-dimethoxyquinazoline. As a result, 365.1 mg (yield: 25%) of Compound 86 was obtained as white crystals.

¹H-NMR (CDCl₃) δ (ppm): 8.73 (s, 1H), 8.00 (d, 1H, J=1.5 Hz), 7.48 (dd, 1H, J=8.5, 1.5 Hz), 7.07 (d, 1H, J=8.5 Hz), 7.01 (s, 1H), 5.34–5.24 (m, 1H), 4.35–4.31 (br.-d, 2H), 4.13, 4.05, 3.97, and 3.57 (s for each, 3H), 3.21–3.02 (m, 4H), 2.41 (s, 3H), 1.86–1.81 (br.-d, 2H).

IR (KBr tab.) (cm⁻¹): 1700, 1654, 1480, 1339, 1128, 810.

Melting Point (ethyl acetate-ether): 172°–175° C.

Example 66

3-[1-(7-Benzyloxy-6-methoxy-4-quinazolinyl)-4-piperidinyl]-1,2,3,4-tetrahydro-1,6-dimethyl-2,4-dioxo-quinazoline (Compound 87)

The procedure similar to that described in Example 57 was repeated, except that 369.0 mg (1.05 mmol) of 1,2,3,4-tetrahydro-1,6-dimethyl-2,4-dioxo-3-(4-piperidinyl)-quinazoline hydrobromide (Compound v) obtained in Example 41 was used and 7-benzyloxy-4-chloro-6-methoxyquinazoline was used in place of 4-chloro-6,7-dimethoxyquinazoline. As a result, 233.8 mg (yield: 42%) of Compound 87 was obtained as white crystals.

¹H-NMR (CDCl₃) δ (ppm): 8.66 (s, 1H), 8.01 (d, 1H, J=1.5 Hz), 7.50–7.28 (m, 7H), 7.21 (s, 1H), 7.08 (d, 1H, J=8.5 Hz), 5.30 (s, 2H), 5.29–5.24 (m, 1H), 4.34–4.30 (br.-d, 2H), 4.01 and 3.58 (s for each, 3H), 3.22–3.04 (m, 4H), 2.42 (s, 3H), 1.86–1.82 (br.-d, 2H).

IR (KBr tab.) (cm⁻¹): 1697, 1655, 1513, 1506, 1329, 754.

Melting Point (ether): 164°–168° C.

Example 67

3-[1-(6,7-Dibenzyloxy-4-quinazolinyl)-4-piperidinyl]-1,2,3,4-tetrahydro-1,6-dimethyl-2,4-dioxoquinazoline (Compound 88)

The procedure similar to that described in Example 61 was repeated, except that 836.0 mg (2.36 mmol) of 1,2,3,4-tetrahydro-1,6-dimethyl-2,4-dioxo-3-(4-piperidinyl)-quinazoline hydrobromide (Compound v) obtained in Example 41 was used and 6,7-dibenzyloxy-4-chloroquinazoline was used in place of 4-chloro-6,7-dimethoxyquinazoline. As a result, 786.3 mg (yield: 54%) of Compound 88 was obtained as white crystals.

¹H-NMR (CDCl₃) δ (ppm): 8.62 (s, 1H), 8.02 (d, 1H, J=1.5 Hz), 7.53–7.21 (m, 12H), 7.16 (s, 1H), 7.09 (d, 1H, J=8.5 Hz), 5.33 (s, 4H), 5.21–5.19 (m, 1H), 4.10–4.06 (br.-d, 2H), 3.59 (s, 3H), 3.06–2.95 (m, 4H), 2.43 (s, 3H), 1.72–1.68 (br.-d, 2H).

IR (KBr tab.) (cm⁻¹): 1702, 1658, 1511, 1445, 1339, 1246, 1204.

Melting Point (ethyl acetate-ether): 172°–174° C.

Example 68

3-[1-(6,7-Diethoxy-4-quinazolinyl)-4-piperidinyl]-1, 2,3,4-tetrahydro-1,6-dimethyl-2,4-dioxoquinazoline (Compound 98)

The procedure similar to that described in Example 57 was repeated, except that 354.0 mg (1.00 mmol) of 1,2,3, 4-tetrahydro-1,6-dimethyl-2,4-dioxo-3-(4-piperidinyl)-quinazoline hydrobromide (Compound v) obtained in Example 41 was used and 4-chloro-6,7-diethoxyquinazoline was used in place of 4-chloro-6,7-dimethoxyquinazoline. As a result, 116.8 mg (yield: 24%) of Compound 98 was obtained as white crystals.

¹H-NMR (CDCl₃) δ (ppm): 8.65 (s, 1H), 8.02 (d, 1H, J=1.5 Hz), 7.49 (dd, 1H, J=8.5, 1.5 Hz), 7.28 (s, 1H), 7.19 (s, 1H), 7.09 (d, 1H, J=8.5 Hz), 5.33–5.25 (m, 1H), 4.38–4.33 (br.-d, 2H), 4.26 (q, 2H, J=7.0 Hz), 4.20 (q, 2H, J=7.0 Hz), 3.58 (s, 3H), 3.24–2.99 (m, 4H), 2.42 (s, 3H), 1.87–1.83 (br.-d, 2H), 1.55 (t, 3H, J=7.0 Hz), 1.54 (t, 3H, J=7.0 Hz).

IR (KBr tab.) (cm⁻¹): 1709, 1656, 1505, 1440, 1035.

Melting Point (ethyl acetate-ether): 173°–175° C.

Example 69

1,2,3,4-Tetrahydro-1,6-dimethyl-3-[1- (6,7-methylene-dioxy-4-quinazolinyl)-4-piperidinyl]-2,4-dioxo-quinazoline (Compound 99)

The procedure similar to that described in Example 40 was repeated, except that 262.0 mg (0.74 mmol) of 1,2,3, 4-tetrahydro-1,6-dimethyl-2,4-dioxo-3-(4-piperidinyl)-quinazoline hydrobromide (Compound v) obtained in Example 41 was used and 4-chloro-6,7-methylenedioxyquinazoline was used in place of 4-chloro-6,7-dimethoxyquinazoline. As a result, 65.8 mg (yield: 20%) of Compound 99 was obtained as white crystals.

¹H-NMR (CDCl₃) δ (ppm): 8.63 (s, 1H), 8.02 (d, 1H, J=2.0 Hz), 7.50 (dd, 1H, J=8.5, 2.0 Hz), 7.38 (s, 1H), 7.23 (s, 1H), 7.10 (d, 1H, J=8.5 Hz), 6.14 (s, 2H), 5.35–5.26 (m, 1H), 4.39–4.34 (br.-d, 2H), 3.58 (s, 3H), 3.24–3.16 (br.-t, 2H), 3.10–2.98 (m, 2H), 2.43 (s, 3H), 1.88–1.84 (br.-d, 2H).

IR (KBr tab.) (cm⁻¹): 1695, 1648, 1490, 1448, 1035.

Melting Point (ethyl acetate-ether): 219°–220° C. (decomposition)

Example 70

3-[1-(6,7-Dimethoxy-4-quinazolinyl)-4-piperidinyl]-1,2,3,4-tetrahydro-6-nitro-2,4-dioxo-1-(2-phthalimido-ethyl)quinazoline (Compound 33)

The procedure similar to that described in Example 1 was repeated, except that 478.0 mg (1.00 mol) of Compound 24 was used and N-(2-bromoethyl)phthalimide was used in place of methyl iodide. As a result, 200 mg (yield: 31%) of Compound 33 was obtained as pale yellow crystals.

¹H-NMR (CDCl₃) δ (ppm): 9.04 (d, 1H, J=2.5 Hz), 8.65 (s, 1H), 8.41 (dd, 1H, J=8.9, 2.5 Hz), 7.81–7.78 (m, 2H), 7.72–7.69 (m, 2H), 7.46 (s, 1H), 7.44 (d, 1H, J=8.9 Hz), 7.14 (s, 1H), 5.26–5.17 (m, 1H), 4.48 (t, 2H, J=6.0 Hz), 4.42–4.38 (br.-d, 2H), 4.12 (t, 2H, J=6.0 Hz), 4.06 and 4.01 (s for each, 3H), 3.26–3.16 (br.-t, 2H), 2.95–2.83 (m, 2H), 1.82–1.79 (br.-d, 2H).

IR (KBr tab.) (cm$^{-1}$): 1710, 1669, 1616, 1504, 1457, 1428, 1395, 1333, 1212, 719.

Melting Point (chloroform-methanol): 143° C.

Example 71

3-[1-(6,7-Dimethoxy-4-quinazolinyl)-4-piperidinyl]-1,2,3,4-tetrahydro-6-nitro-2,4-dioxo-1-(3-phthalimido-propyl) quinazoline (Compound 34)

The procedure similar to that described in Example 1 was repeated, except that 478.0 mg (1.00 mol) of Compound 24 was used and N-(3-bromopropyl)phthalimide was used in place of methyl iodide. As a result, 280 mg (yield: 42%) of Compound 34 was obtained as a pale yellow amorphous solid.

$^{1}$H-NMR (CDCl$_3$) δ (ppm): 9.05 (d, 1H, J=2.5 Hz), 8.68 (s, 1H), 8.47 (dd, 1H, J=8.9, 2.5 Hz), 7.86–7.81 (m, 2H), 7.76–7.71 (m, 2H), 7.34 (s, 1H), 7.26 (d, 1H, J=8.9 Hz), 7.16 (s, 1H), 5.27–5.19 (m, 1H), 4.41–4.36 (br.-d, 2H), 4.30–4.25 (dist.-t, 2H), 4.04 and 4.01 (s for each, 3H), 3.87 (t, 2H, J=7.0 Hz), 3.25–3.16 (br.-t, 2H), 3.01–2.88 (m, 2H), 2.25–2.14 (m, 2H), 1.89–1.85 (br.-d, 2H).

IR (KBr tab. ) (cm$^{-1}$): 1702, 1657, 1615, 1498, 1430, 1330, 1214, 717.

Example 72

1-(2-Aminoethyl)-3-[1-(6,7-dimethoxy-4-quinazolinyl)-4-piperidinyl]-1,2,3,4-tetrahydro-6-nitro-2,4-dioxo-quinazoline (Compound 29)

In a solvent mixture of 5 ml of ethanol and 5 ml of chloroform was dissolved 160.0 mg (0.25 mmol) of Compound 33 obtained in Example 70, and 0.04 ml (0.81 mmol) of hydrazine hydrate was added thereto, followed by heating at 60° C. for 1 hour. The solvent was distilled off under reduced pressure, and chloroform was added to the residue. The precipitated crystals were filtered off, and the filtrate was evaporated under reduced pressure. The residue was dissolved in a small amount of chloroform, and a saturated solution of hydrogen chloride in ethyl acetate was added thereto. The precipitated crystals were collected by filtration and purified by washing with chloroform and diethyl ether to give 113.7 mg (yield: 78%) of the dihydrochloride of Compound 29 as pale yellow crystals.

$^{1}$H-NMR (DMSO-d$_6$) δ (ppm): 8.83 (s, 1H), 8.76 (d, 1H, J=2.5 Hz), 8.53 (dd, 1H, J=9.0, 2.5 Hz), 7.86 (d, 1H, J=9.0 Hz), 7.38 (s, 1H), 7.37 (s, 1H), 5.32–5.25 (m, 1H), 4.86–4.81 (br.-d, 2H), 4.50–4.40 (br.-t, 2H), 4.00 and 3.96 (s for each, 3H), 3.74–3.65 (br.-t, 2H), 3.10–3.00 (m, 2H), 2.70–2.67 (m, 2H), 2.00–1.96 (br.-d, 2H).

IR (KBr tab.) (cm$^{-1}$): 3400 (br), 1710, 1659, 1615, 1499, 1334.

Melting Point (chloroform-ether): 263° C.

Example 73

1-(2-Aminopropyl)-3-[1-(6,7-dimethoxy-4-quinazolinyl)-4-piperidinyl]-1,2,3,4-tetrahydro-6-nitro-2,4-dioxo-quinazoline (Compound 30)

The procedure similar to that described in Example 72 was repeated using 128.1 mg (0.19 mmol) of Compound 34 obtained in Example 71, whereby 46.4 mg (yield: 40%) of the dihydrochloride of Compound 30 was obtained as pale yellow crystals.

$^{1}$H-NMR (DMSO-d$_6$) δ (ppm): 8.83 (s, 1H), 8.76 (d, 1H, J=2.5 Hz), 8.51 (dd, 1H, J=9.0, 2.5 Hz), 7.83 (d, 1H, J=9.0 Hz), 7.40 (s, 1H), 7.38 (s, 1H), 5.38–5.22 (m, 1H), 4.86–4.82 (br.-d, 2H), 4.30–4.20 (br.-t, 2H), 4.00 and 3.97 (s for each, 3H), 3.75–3.66 (br.-t, 2H), 2.96–2.94 (m, 2H), 2.75–2.67 (m, 2H), 1.98–1.95 (br.-d, 4H).

IR (KBr tab.) (cm$^{-1}$): 3400 (br), 1711, 1656, 1614, 1500, 1330.

Melting Point (chloroform-ether): 260° C.

Example 74

3-[1-(6,7-Dimethoxy-4-quinazolinyl)-4-piperidinyl]-1,2,3,4-tetrahydro-6-methoxy-1-methyl-2,4-dioxo-quinazoline (Compound 69)

The procedure similar to that described in Example 1 was repeated, except that 251.0 mg (0.56 mmol) of 3-[1-(6,7-dimethoxy-4-quinazolinyl)-4-piperidinyl]-1,2,3,4-tetrahydro-6-hydroxy-2,4-dioxoquinazoline (Compound 102) obtained in Reference Example 13 was used in place of Compound 24 and 3 equivalents of methyl iodide and 3 equivalents of sodium hydride were used. As a result, 197.2 mg (yield: 74%) of Compound 69 was obtained as white crystals.

$^{1}$H-NMR (CDCl$_3$) δ (ppm): 8.68 (s, 1H), 7.66 (d, 1H, J=2.5 Hz), 7.31 (s, 1H), 7.27 (dd, 1H, J=8.5, 2.5 Hz), 7.19 (s, 1H), 7.13 (d, 1H, J=8.5 Hz), 5.34–5.26 (m, 1H), 4.41–4.36 (br.-d, 2H), 4.04, 4.01, 3.88, and 3.59 (s for each, 3H), 3.26–3.00 (m, 4H), 1.88–1.85 (br.-d, 2H).

IR (KBr tab. ) (cm$^{-1}$): 1696, 1653, 1502.

Melting Point (ethyl acetate-ether): 211°–212° C. (decomposition)

Example 75

3-[1-(6,7-Dimethoxy-4-quinazolinyl)-4-piperidinyl]-6-ethoxy-1-ethyl-1,2,3,4-tetrahydro-2,4-dioxoquinazoline (Compound 72)

The procedure similar to that described in Example 74 was repeated, except that 150.0 mg (0.33 mmol) of Compound 102 was used and ethyl iodide was used in place of methyl iodide. As a result, 121.2 mg (yield: 73%) of Compound 72 was obtained as white crystals.

$^{1}$H-NMR (CDCl$_3$) δ (ppm): 8.67 (s, 1H), 7.65 (d, 1H, J=2.5 Hz), 7.31 (s, 1H), 7.26 (dd, 1H, J=9.0, 2.5 Hz), 7.19 (s, 1H), 7.14 (d, 1H, J=9.0 Hz), 5.33–5.24 (m, 1H), 4.40–4.36 (br.-d, 2H), 4.17 (q, 2H, J=7.0 Hz), 4.10 (q, 2H, J=7.0 Hz), 4.04 and 4.01 (s for each, 3H), 3.26–3.00 (m, 4H), 1.90–1.89 (br.-d, 2H), 1.44 (t, 3H, J=7.0 Hz), 1.35 (t, 3H, J=7.0 Hz).

IR (KBr tab.) (cm$^{-1}$): 1696, 1657, 1506, 1341.

Melting Point (ethyl acetate-ether): 207°–209° C.

Example 76

3-[1-(6,7-Dimethoxy-4-quinazolinyl)-4-piperidinyl]-1,2,3,4-tetrahydro-2,4-dioxo-6-propoxy-1-propyl-quinazoline (Compound 73)

The procedure similar to that described in Example 74 was repeated, except that 150.0 mg (0.33 mmol) of Compound 102 was used and propyl iodide was used in place of methyl iodide. As a result, 110.2 mg (yield: 63%) of Compound 73 was obtained as white crystals.

¹H-NMR (CDCl₃) δ (ppm): 8.67 (s, 1H), 7.65 (d, 1H, J=3.0 Hz), 7.33 (s, 1H), 7.26 (dd, 1H, J=9.0, 3.0 Hz), 7.19 (s, 1H), 7.09 (d, 1H, J=9.0 Hz), 5.30–5.25 (m, 1H), 4.41–4.36 (br.-d, 2H), 4.07–3.96 (m, 4H), 4.04 and 4.01 (s for each, 3H), 3.26–3.03 (m, 4H), 1.88–1.72 (m, 6H), 1.05 (t, 3H, J=7.0 Hz), 1.03 (t, 3H, J=7.0 Hz).

IR (KBr tab.) (cm⁻¹): 1691, 1652, 1503, 1208.

Melting Point (ethyl acetate-ether): 179°–180° C.

Example 77

3-[1-(6,7-Dimethoxy-4-quinazolinyl)-4-piperidinyl]-1-ethyl-1,2,3,4-tetrahydro-6-methoxy-2,4-dioxoquinazoline (Compound 70)

The procedure similar to that described in Example 1 was repeated, except that 100.0 mg (0.21 mmol) of Compound 66 obtained in Example 51 was used in place of Compound 24. As a result, 65.6 mg (yield: 64%) of Compound 70 was obtained as white crystals.

¹H-NMR (CDCl₃) δ (ppm): 8.68 (s, 1H), 7.67 (d, 1H, J=2.9 Hz), 7.28–7.25 (m, 2H), 7.19 (s, 1H), 7.15 (d, 1H, J=8.5 Hz), 5.34–5.24 (m, 1H), 4.38–4.33 (br.-d, 2H), 4.17 (q, 2H, J=7.0 Hz), 4.03, 4.01, and 3.88 (s for each, 3H), 3.25–3.02 (m, 4H), 1.89–1.84 (br.-d, 2H), 1.36 (t, 3H, J=7.0 Hz).

IR (KBr tab.) (cm⁻¹): 1699, 1654, 1505, 1426.

Melting Point (ethyl acetate-ether): 227°–229° C.

Example 78

3-[1-(6,7-Dimethoxy-4-quinazolinyl)-4-piperidinyl]-1,2,3,4-tetrahydro-6-methoxy-2,4-dioxo-1-propyl-quinazoline (Compound 71)

The procedure similar to that described in Example 1 was repeated, except that 100.0 mg (0.20 mmol) of Compound 67 obtained in Example 52 was used in place of Compound 24. As a result, 51.1 mg (yield: 50%) of Compound 71 was obtained as white crystals.

¹H-NMR (CDCl₃) δ (ppm): 8.68 (s, 1H), 7.66 (d, 1H, J=3.0 Hz), 7.29–7.26 (m, 2H), 7.19 (s, 1H), 7.11 (d, 1H, J=9.0 Hz), 5.35–5.24 (m, 1H), 4.39–4.35 (br.-d, 2H), 4.08 (dist.-t, 2H), 4.04, 4.01, and 3.88 (s for each, 3H), 3.25–3.04 (m, 4H), 1.88–1.73 (m, 4H), 1.04 (t, 3H, J=7.0 Hz).

IR (KBr tab.) (cm⁻¹): 1699, 1654, 1502, 1476, 1428, 1327, 1213.

Melting Point (ethyl acetate-ether): 171°–172° C.

Example 79

1,2,3,4-Tetrahydro-3-[1-(7-hydroxy-6-methoxy-4-quinazolinyl)-4-piperidinyl]-1,6-dimethyl-2,4-dioxoquinazoline (Compound 89)

In 10 ml of ethanol was dissolved 150 mg (0.28 mmol) of Compound 87 obtained in Example 66, and 30 mg of 10% palladium on carbon was added thereto, followed by vigorous stirring at room temperature for 6 hours under a hydrogen atmosphere at atmospheric pressure. The reaction mixture was filtered using a filter aid, and the filtrate was concentrated under reduced pressure. To the residue were added ethanol and ethyl acetate. The precipitated crystals were collected by filtration, washed, and dried to give 105.2 mg (yield: 84%) of Compound 89 as white crystals.

¹H-NMR (CDCl₃) δ (ppm): 8.69 (s, 1H), 8.01 (d, 1H, J=1.5 Hz), 7.49 (dd, 1H, J=8.5, 1.5 Hz), 7.34 (s, 1H), 7.19 (s, 1H), 7.08 (d, 1H, J=8.5 Hz), 5.33–5.24 (m, 1H), 4.32–4.29 (br.-d, 2H), 4.03 and 3.58 (s for each, 3H), 3.22–3.04 (m, 4H), 2.42 (s, 3H), 1.87–1.83 (br.-d, 2H).

IR (KBr tab.) (cm⁻¹): 1701, 1657, 1511, 1463, 1424, 799.

Melting Point (ethyl acetate-ether): 265°–266° C. (decomposition)

Example 80

1,2,3,4-Tetrahydro-3-[1-(6-hydroxy-7-methoxy-4-quinazolinyl)-4-piperidinyl]-1,6-dimethyl-2,4-dioxoquinazoline (Compound 90)

In 5 ml of DMF was suspended 360 mg (9.0 mmol) of 60% sodium hydride, and a solution of 0.92 ml (9.0 mmol) of thiophenol in 10 ml of DMF was added dropwise to the suspension under ice cooling. After stirring for 10 minutes, a solution of 1.38 g (3.0 mmol) of Compound 50 obtained in Example 41 in 10 ml of DMF was added thereto under ice cooling, followed by stirring at 100° C. for 10 hours. After the reaction mixture was cooled to room temperature, water was added thereto, and the mixture was extracted with chloroform. The aqueous layer was adjusted to pH 5 by addition of 4N hydrochloric acid and extracted with chloroform. The combined organic layer was washed with an aqueous solution of sodium chloride and dried. The solvent was distilled off, and the residue was purified by silica gel column chromatography (eluent: chloroform/methanol=50/1). The compound eluted as a component with low polarity was recrystallized from ether to give 302.8 mg (yield: 23%) of Compound 90 as white crystals. The substance eluted as a component with high polarity was recrystallized from ether/ethanol to give 787.9 mg (yield: 59%) of Compound 89 as white crystals.

¹H-NMR (CDCl₃) δ (ppm): 8.64 (s, 1H), 8.01 (d, 1H, J=1.5 Hz), 7.48 (dd, 1H, J=9.0, 1.5 Hz), 7.36 (s, 1H), 7.25 (s, 1H), 7.08 (d, 1H, J=9.0 Hz), 5.30–5.22 (m, 1H), 4.37–4.33 (br.-d, 2H), 4.04 and 3.57 (s for each, 3H), 3.19–3.01 (m, 4H), 2.42 (s, 3H), 1.83–1.78 (br.-d, 2H).

IR (KBr tab.) (cm⁻¹): 1703, 1655, 1509, 1492, 1443, 1211.

Melting Point (ether): 265°–267° C. (decomposition)

Example 81

3-[1-(6,7-Dihydroxy-4-quinazolinyl)-4-piperidinyl]-1,2,3,4-tetrahydro-1,6-dimethyl-2,4-dioxoquinazoline (Compound 97)

The procedure similar to that described in Example 79 was repeated, except that 200.0 mg (0.33 mmol) of Compound 88 obtained in Example 67 was used in place of Compound 87 and DMF was used as a reaction solvent in place of ethanol. As a result, 98.5 mg (yield: 70%) of Compound 97 was obtained as white crystals.

¹H-NMR (DMSO-d₆) δ (ppm): 10.4–9.8 (br, 2H), 8.43 (s, 1H), 7.87 (d, 1H, J=1.5 Hz), 7.60 (dd, 1H, J=8.5, 1.5 Hz), 7.57 (d, 1H, J=8.5 Hz), 7.26 (s, 1H), 7.06 (s, 1H), 5.20–5.05 (m, 1H), 4.23–4.18 (br.-d, 2H), 3.51 (s, 3H), 3.10–2.80 (m, 4H), 2.39 (s, 3H), 1.76–1.73 (br.-d, 2H).

IR (KBr tab.) (cm⁻¹): 3400 (br), 1698, 1658, 1480, 1350.

Melting Point (DMF-water): 240°–245° C.

Example 82

1,2,3,4-Tetrahydro-3-[1-(6-methoxy-7-propoxy-4-quinazolinyl)-4-piperidinyl]-1,6-dimethyl-2,4-dioxoquinazoline (Compound 91)

The procedure similar to that described in Example 1 was repeated, except that 223.5 mg (0.50 mmol) of Compound 89 obtained in Example 79 was used in place of Compound 24 and propyl iodide was used in place of methyl iodide. As a result, a free base of Compound 91 was obtained, which was then converted to the hydrochloride in the similar manner as in Example 41 to give 229.9 mg (yield: 87%) of the hydrochloride of Compound 91 as white crystals.

$^1$H-NMR (CDCl$_3$) δ (ppm): 8.54 (s, 1H), 7.99 (d, 1H, J=2.0 Hz), 7.91 (s, 1H), 7.51 (dd, 1H, J=8.0, 2.0 Hz), 7.16 (s, 1H), 7.11 (d, 1H, J=8.0 Hz), 5.48–5.44 (m, 1H), 4.91–4.87 (br.-d, 2H), 4.24 (t, 2H, J=7.0 Hz), 3.98 and 3.57 (s for each, 3H), 3.57–3.46 (br.-t, 2H), 3.11–2.92 (m, 2H), 2.42 (s, 3H), 1.99–1.88 (m, 4H), 1.09 (t, 3H, J=7.0 Hz).

IR (KBr tab.) (cm$^{-1}$): 1697, 1657, 1510.

Melting Point (ether): 202°–203° C.

Example 83

1,2,3,4-Tetrahydro-3-[1-(7-methoxy-6-propoxy-4-quinazolinyl)-4-piperidinyl]-1,6-dimethyl-2,4-dioxo-quinazoline (Compound 92)

The procedure similar to that described in Example 1 was repeated, except that 100.0 mg (0.22 mmol) of Compound 90 obtained in Example 80 was used in place of Compound 24 and propyl iodide was used in place of methyl iodide. As a result, 69.0 mg (yield: 64%) of Compound 92 was obtained as white crystals.

$^1$H-NMR (CDCl$_3$) δ (ppm): 8.67 (s, 1H), 8.01 (d, 1H, J=1.5 Hz), 7.48 (dd, 1H, J=8.5, 1.5 Hz), 7.24 (s, 1H), 7.19 (s, 1H), 7.08 (d, 1H, J=8.5 Hz), 5.28–5.24 (m, 1H), 4.35–4.30 (br.-d, 2H), 4.10 (dist.-t, 2H), 4.01 and 3.58 (s for each, 3H), 3.22–3.02 (m, 4H), 2.42 (s, 3H), 1.99–1.81 (m, 4H), 1.10 (t, 3H, J=7.0 Hz).

IR (KBr tab.) (cm$^{-1}$): 1703, 1652, 1503, 1329, 1210.

Melting Point (ether): 187°–188° C.

Example 84

3-[1-(7-Ethoxycarbonylmethoxy-6-methoxy-4-quinazolinyl)-4-piperidinyl]-1,2,3,4-tetrahydro-1,6-dimethyl-2,4-dioxoquinazoline (Compound 93)

The procedure similar to that described in Example 1 was repeated, except that 500.0 mg (1.12 mmol) of Compound 89 obtained in Example 79 was used in place of Compound 24 and ethyl bromoacetate was used in place of methyl iodide. As a result, 530.0 mg (yield: 89%) of Compound 93 was obtained as white crystals.

$^1$H-NMR (CDCl$_3$) δ (ppm): 8.67 (s, 1H), 8.02 (d, 1H, J=1.5 Hz), 7.49 (dd, 1H, J=8.5, 1.5 Hz), 7.23 (s, 1H), 7.12 (s, 1H), 7.09 (d, 1H, J=8.5 Hz), 5.33–5.24 (m, 1H), 4.83 (s, 2H), 4.35–4.25 (m, 4H), 4.02 and 3.58 (s for each, 3H), 3.23–3.04 (m, 4H), 2.42 (s, 3H), 1.87–1.83 (br.-d, 2H), 1.31 (t, 3H, J=7.0 Hz).

IR (KBr tab.) (cm$^{-1}$): 1700, 1658, 1514, 1506.

Melting Point (DMF-water): 122°–124° C.

Example 85

3-[1-(6-Ethoxycarbonylmethoxy-7-methoxy-4-quinazolinyl)-4-piperidinyl]-1,2,3,4-tetrahydro-1,6-dimethyl-2,4-dioxoquinazoline (Compound 94)

The procedure similar to that described in Example 1 was repeated, except that 500.0 mg (1.12 mmol) of Compound 90 obtained in Example 80 was used in place of Compound 24 and ethyl bromoacetate was used in place of methyl iodide. As a result, 323.3 mg (yield: 54%) of Compound 94 was obtained as white crystals.

$^1$H-NMR (CDCl$_3$) δ (ppm): 8.67 (s, 1H), 8.01 (d, 1H, J=1.5 Hz), 7.49 (dd, 1H, J=8.5, 1.5 Hz), 7.29 (s, 1H), 7.19 (s, 1H), 7.09 (d, 1H, J=8.5 Hz), 5.27–5.23 (m, 1H), 4.78 (s, 2H), 4.32–4.24 (m, 4H), 4.03 and 3.58 (s for each, 3H), 3.21–2.99 (m, 4H), 2.42 (s, 3H), 1.84–1.81 (br.-d, 2H), 1.29 (t, 3H, J=7.0 Hz ).

IR (KBr tab.) (cm$^{-1}$): 1700, 1649, 1511.

Melting Point (ether): 187°–188° C.

Example 86

3-{1-[7-(2-Dimethylaminoethyl)oxy-6-methoxy-4-quinazolinyl]-4-piperidinyl}-1,2,3,4-tetrahydro-1,6-dimethyl-2,4-dioxoquinazoline (Compound 96)

The procedure similar to that described in Example 1 was repeated, except that 223.5 mg (0.50 mmol) of Compound 89 obtained in Example 79 was used in place of Compound 24, dimethylaminoethyl chloride hydrochloride was used in place of methyl iodide, 2 equivalents of sodium hydride was used, and the reaction was conducted at 60° C., whereby 192.2 mg (yield: 74%) of a free base of Compound 96 was obtained as an amorphous substance. The obtained free base (160.5 mg, 0.31 mmol) was dissolved in 5 ml of acetone, and 0.04 ml (0.62 mmol) of methanesulfonic acid was added thereto, followed by stirring at room temperature for 30 minutes. The solvent was distilled off under reduced pressure, and ether was added to the residue. The precipitated crystals were collected by filtration to give 208.1 mg (yield: 95%) of the dimethanesulfonate of Compound 96 as white crystals.

$^1$H-NMR (CDCl$_3$) δ (ppm) (for free base): 8.68 (s, 1H), 8.01 (d, 1H, J=1.5 Hz), 7.49 (dd, 1H, J=8.5, 1.5 Hz), 7.25 (s, 1H), 7.18 (s, 1H), 7.09 (d, 1H, J=8.5 Hz), 5.33–5.24 (m, 1H), 4.34–4.28 (m, 4H), 3.98 and 3.58 (s for each, 3H), 3.18–3.03 (m, 4H), 2.94 (t, 2H, J=6.0 Hz), 2.43 (s, 3H), 2.42 (s, 6H), 1.87–1.83 (br.-d, 2H).

IR (KBr tab.) (cm$^{-1}$) (for dimethanesulfonate): 1705, 1654, 1549, 1511, 769.

Melting Point (ether): 181°–183° C.

Example 87

3-[1-(7-Carboxymethyloxy-6-methoxy-4-quinazolinyl)-4-piperidinyl]-1,2,3,4-tetrahydro-1,6-dimethyl-2,4-dioxo-quinazoline (Compound 95)

In 10 ml of methanol was dissolved 250.0 mg (0.47 mmol) of Compound 93 obtained in Example 84, and 5 ml of a 2N aqueous solution of sodium hydroxide was added thereto, followed by heating under reflux for 6 hours. After cooling, the reaction mixture was neutralized by addition of 4N hydrochloric acid, and extracted with chloroform. The organic layer was washed and dried, and the solvent was distilled off under reduced pressure. To the residue was added ether, and the precipitated crystals were collected by filtration and dried to give 77.8 mg (yield: 33%) of Compound 95 as white crystals.

$^1$H-NMR (CDCl$_3$) δ (ppm): 8.51 (s, 1H), 7.99 (d, 1H, J=1.5 Hz), 7.65 (s, 1H), 7.49 (dd, 1H, J=8.5, 1.5 Hz), 7.13 (s, 1H), 7.08 (d, 1H, J=8.5 Hz), 5.40–5.25 (m, 1H), 4.97 (s, 2H), 4.65–4.60 (br.-d, 2H), 4.00 and 3.56 (s for each, 3H), 3.35–3.26 (br.-t, 2H), 3.03–2.95 (m, 2H), 2.41 (s, 3H), 1.89–1.85, (br.-d, 2H).

IR (KBr tab.) (cm$^{-1}$): 3600 (br), 1698, 1651, 1510.

Melting Point (ether): 199°–203° C.

Example 88

3-[1-(6,7-Dimethoxy-1-phthalazinyl)-4-piperidinyl]-1,2,3,4-tetrahydro-1,6-dimethyl-2,4-dioxoquinazoline (Compound 77)

In 10 ml of acetic acid was dissolved 300 mg (0.61 mmol) of Compound 76 obtained in Example 58, and 40 mg of 10% palladium on carbon suspended in a small amount of water was added to the solution, followed by vigorous stirring at 40° C. for 3 hours under a hydrogen atmosphere at atmospheric pressure. The reaction mixture was filtered using a filter aid, and the filtrate was neutralized by addition of a saturated aqueous solution of sodium bicarbonate and extracted with ethyl acetate. The organic layer was washed successively with water and a saturated aqueous solution of sodium chloride, and then dried. The solvent was distilled off under reduced pressure, and the residue was purified by silica gel column chromatography (eluent: chloroform/methanol=50/1). Ether was added to the product, and the precipitated crystals were collected by filtration, washed, and dried to give 52.9 mg (yield: 19%) of Compound 77 as white crystals.

$^1$H-NMR (CDCl$_3$) δ (ppm): 9.08 (s, 1H), 8.03 (d, 1H, J=2.0 Hz), 7.50 (dd, 1H, J=9.0, 2.0 Hz), 7.39 (s, 1H), 7.16 (s, 1H), 7.10 (d, 1H, J=9.0 Hz), 5.31–5.24 (m, 1H), 4.09 and 4.07 (s for each, 3H), 4.00–3.96 (br.-d, 2H), 3.60 (s, 3H), 3.27–3.07 (m, 4H), 2.43 (s, 3H), 1.90–1.86 (br.-d, 2H).

IR (KBr tab.) (cm$^{-1}$): 1699, 1660, 1648, 1505, 1422, 1311, 1118.

Melting Point (ether): 173°–175° C.

Example 89

3-[1-(6,7-Dimethoxy-4-quinazolinyl)-4-piperidinyl]-1,2,3,4-tetrahydro-6-(1-hydroxyethyl)-1-methyl-2,4-dioxoquinazoline (Compound 60)

In a solvent mixture of 3 ml of methanol and 3 ml of chloroform was dissolved 200.0 mg (0.41 mmol) of Compound 63 obtained in Example 50, and sodium borohydride was added thereto in excess, followed by heating at 60° C. for 30 minutes. After cooling, water was added to the reaction mixture, and the mixture was extracted with chloroform. The organic layer was washed and dried, and the solvent was distilled off under reduced pressure. To the residue was added ether, and the precipitated crystals were collected by filtration and dried to give 146.4 mg (yield: 73%) of Compound 60 as white crystals.

$^1$H-NMR (CDCl$_3$) δ (ppm): 8.67 (s, 1H), 8.19 (d, 1H, J=2.0 Hz), 7.76 (dd, 1H, J=8.5, 2.0 Hz), 7.24 (s, 1H), 7.19 (d, 1H, J=8.5 Hz), 7.18 (s, 1H), 5.32–5.24 (m, 1H), 5.01 (q, 1H, J=6.3 Hz), 4.34–4.30 (br.-d, 2H), 4.03, 4.01, and 3.60 (s for each, 3H), 3.22–3.00 (m, 4H), 1.87–1.82 (br.-d, 2H), 1.53 (d, 3H, J=6.3 Hz).

IR (KBr tab.) (cm$^{-1}$): 3400 (br), 1703, 1647, 1504, 1212.

Melting Point (ether): 215°–217° C.

Example 90

3-[1-(6,7-Dimethoxy-4-quinazolinyl)-4-piperidinyl]-1,2,3,4-tetrahydro-6-(2-hydroxy-2-propyl)-1-methyl-2,4-dioxoquinazoline (Compound 61)

In 3 ml of THF was suspended 246.5 mg (1.0 mmol) of thoroughly dried cerium chloride, and 1 ml of a 1M solution of methylmagnesium bromide in THF was added thereto under an argon gas atmosphere, followed by stirring at room temperature for 1 hour. To the reaction mixture was dropwise added a solution of 245.0 mg (0.50 mmol) of Compound 63 obtained in Example 50 in 5 ml of THF, and the mixture was stirred at room temperature for 3 hours. A saturated aqueous solution of ammonium chloride was added thereto in excess to stop the reaction, followed by extraction with chloroform. The organic layer was washed and dried, and the solvent was distilled off under reduced pressure. The residue was purified by silica gel column chromatography (eluent: chloroform/methanol=100/1) and recrystallized from ether to give 78.8 mg (yield: 31%) of Compound 61 as white crystals.

$^1$H-NMR (CDCl$_3$) δ (ppm): 8.67 (s, 1H), 8.28 (d, 1H, J=2.5 Hz), 7.90 (dd, 1H, J=9.0, 2.5 Hz), 7.24 (s, 1H), 7.19 (s, 1H), 7.17 (d, 1H, J=9.0 Hz), 5.29–5.24 (m, 1H), 4.35–4.30 (br.-d, 2H), 4.03, 4.01, and 3.60 (s for each, 3H), 3.23–3.00 (m, 4H), 1.87–1.82 (br.-d, 2H), 1.63 (s, 6H).

IR (KBr tab.) (cm$^{-1}$): 3500 (br), 1703, 1647, 1501, 1472, 1427, 1030, 984.

Melting Point (ether): 234°–236° C.

Example 91

6-Carboxy-3-[1-(6,7-dimethoxy-4-quinazolinyl)-4-piperidinyl]-1,2,3,4-tetrahydro-1-methyl-2,4-dioxoquinazoline (Compound 62)

In a solvent mixture of 30 ml of 1,4-dioxane and 5 ml of chloroform was suspended 245.0 mg (0.50 mmol) of Compound 63 obtained in Example 50. The suspension was added to a solution of hypobromous acid (3 mmol) which was prepared by adding 0.15 ml of bromine to a solvent mixture of 3 ml of a 2N aqueous solution of sodium hydroxide and 1 ml of 1,4-dioxane under ice cooling. The mixture was stirred at room temperature for one day, and then neutralized by addition of 4N hydrochloric acid, followed by extraction with chloroform. The organic layer was washed and dried, and the solvent was distilled off under reduced pressure. To the residue was added ether, and the precipitated crystals were collected by filtration and dried to give 52.4 mg (yield: 21%) of Compound 62 as white crystals.

$^1$H-NMR (DMSO-d$_6$) δ (ppm): 8.73 (s, 1H), 8.57 (d, 1H, J=2.0 Hz), 8.23 (dd, 1H, J=8.5, 2.0 Hz), 7.53 (d, 1H, J=8.5 Hz), 7.30 (s, 1H), 7.24 (s, 1H), 5.35–5.20 (m, 1H), 4.68–4.63 (br.-d, 2H), 3.98, 3.95, and 3.54 (s for each, 3H), 3.45–3.30 (m, 2H), 2.80–2.65 (m, 2H), 1.90–1.85 (br.-d, 2H).

IR (KBr tab.) (cm$^{-1}$): 3400–2800 (br), 1706, 1657, 1608, 1510, 1501, 1210.

Melting Point (ether): 230° C. (decomposition)

Example 92

6-Amino-3-[1-(6,7-dimethoxy-4-quinazolinyl)-4-piperidinyl]-1-ethyl-1,2,3,4-tetrahydro-2,4-dioxoquinazoline (Compound 64)

The procedure similar to that described in Example 14 was repeated, except that 5.6 g (11.1 mmol) of Compound 2 obtained in Example 2 was used in place of Compound 1. As a result, 3.4 g (yield: 64%) of Compound 64 was obtained as white crystals.

$^1$H-NMR (CDCl$_3$) δ (ppm): 8.68 (s, 1H), 7.49 (m, 1H), 7.28 (s, 1H), 7.21 (s, 1H), 7.04 (m, 2H), 5.32–5.23 (m, 1H), 4.37–4.33 (br.-d, 2H), 4.13 (q, 2H, J=7.0 Hz), 4.03 and 4.01 (s for each, 3H), 3.23–3.01 (m, 4H), 1.88–1.83 (br.-d, 2H), 1.33 (t, 3H, J=7.0 Hz).

IR (KBr tab.) (cm$^{-1}$): 3410, 1695, 1645, 1506, 1333, 1244.

Melting Point (ether): 243°–245° C.

Example 93

6-Acetylamino-3-[1-(6,7-dimethoxy-4-quinazolinyl)-4-piperidinyl]-1-ethyl-1,2,3,4-tetrahydro-2,4-dioxoquinazoline (Compound 65)

The procedure similar to that described in Reference Example 2 was repeated, except that 300.0 mg (0.63 mmol)

of Compound 64 obtained in Example 92 was used in place of Compound 19. As a result, 248.6 mg (yield: 76%) of Compound 65 was obtained as white crystals.

$^1$H-NMR (CDCl$_3$) δ (ppm): 8.67 (s, 1H), 8.25 (dd, 1H, J=8.9, 2.5 Hz), 8.00 (d, 1H, J=2.5 Hz), 7.67 (br.-s, 1H, NH), 7.34 (s, 1H), 7.18 (d, 1H, J=8.9 Hz), 7.18 (s, 1H), 5.32–5.23 (m, 1H), 4.43–4.38 (br.-d, 2H), 4.17 (q, 2H, J=7.3 Hz), 4.04 and 4.01 (s for each, 3H), 3.26–3.17 (br.-t, 2H), 3.11–2.98 (m, 2H), 2.23 (s, 3H), 1.89–1.84 (br.-d, 2H), 1.35 (t, 3H, J=7.3 Hz).

IR (KBr tab.) (cm$^{-1}$): 1690, 1660, 1649, 1502.

Melting Point (ethyl acetate): 203°–206° C.

Example 94

Diastereomixture of 3-[1-(6,7-dimethoxy-4-quinazolinyl)-3-methyl-4-piperidinyl]-1-ethyl-1,2,3,4-tetrahydro-6-nitro-2,4-dioxoquinazoline
(Compound 103)

The procedure similar to that described in Example 15 was repeated, except that 210 mg (0.52 mmol) of 3-(1-ethoxycarbonyl-3-methyl-4-piperidinyl)-1-ethyl-1,2,3,4-tetrahydro-6-nitro-2,4-dioxoquinazoline (Compound kk; diastereomixture) was used in place of Compound a, whereby 203 mg of crude 1-ethyl-1,2,3,4-tetrahydro-3-(3-methyl-4-piperidinyl)-6-nitro-2,4-dioxoquinazoline hydrobromide was obtained. The product was treated in the similar manner as in Example 15 to give 193 mg (yield: 72%) of Compound 103 as a 6:4 diastereomixture.

$^1$H-NMR (CDCl$_3$) δ (ppm): 9.09 (d, 1H, J=2.6 Hz), 8.69 (s, 1H), 8.51 (dd, 1H, J=9.2, 2.6 Hz), 7.35 (s, 0.6H), 7.32 (d, 1H, J=9.2 Hz), 7.29 (s, 1H), 7.17 (s, 0.4H), 5.25–5.15 (m, 0.6H), 5.1–4.8 (m, 0.4H), 4.45–4.1 (m, 4H), 4.04 (s, 3H), 4.02 (s, 1.8H), 4.01 (s, 1.2H), 3.7–3.4 (m, 1.2H), 3.3–3.15 (m, 1.4H), 3.0–2.8 (m, 0.8H), 2.55–2.45 (m, 0.6H), 2.0–1.8 (m, 1H), 1.41 (t, 3H, J=7.3 Hz), 1.27 (d, 1.8H, J=7.3 Hz), 0.90 (d, 1.2H, J=7.0 Hz).

IR (KBr tab.) (cm$^{-1}$): 1716, 1666, 1613, 1573, 1525, 1452, 1331.

Example 95

Diastereomixture of 3-[1-(6,7-dimethoxy-4-quinazolinyl)-3-ethyl-4-piperidinyl]-1,2,3,4-tetrahydro-1-methyl-6-nitro-2,4-dioxoquinazoline
(Compound 104)

The procedure similar to that described in Example 15 was repeated, except that 61.1 mg (0.15 mmol) of 3-(1-ethoxycarbonyl-3-ethyl-4-piperidinyl)-1,2,3,4-tetrahydro-1-methyl-6-nitro-2,4-dioxoquinazoline (Compound ll; diastereo-mixture) was used in place of Compound a, whereby 70.4 mg of crude 3-(3-ethyl-4-piperidinyl)-1,2,3,4-tetrahydro-1-methyl-6-nitro-2,4-dioxoquinazoline hydrobromide was obtained. The product was treated in the similar manner as in Example 15 to give 30.4 mg (yield: 39%) of Compound 104 as a 6:4 diastereo-mixture.

$^1$H-NMR (CDCl$_3$) δ (ppm): 9.09 (d, 1H, J=2.4 Hz), 8.70 (s, 0.4H), 8.65 (s, 0.6H), 8.53 (dd, 1H, J=8.9, 2.4 Hz), 7.41 (s, 0.6H), 7.33 (d, 1H, J=8.9 Hz), 7.32 (s, 0.4H), 7.25 (s, 0.6H), 7.17 (s, 0.4H), 5.35–5.25 (m, 1H), 4.45–4.25 (m, 2H), 4.05 (s, 3H), 4.03 (s, 3H), 3.68 (s, 3H), 3.8–3.5 (m, 2H), 3.5–3.25 (m, 1H), 2.25–2.15 (m, 1H), 2.0–1.8 (m, 1H), 1.7–1.5 (m, 1H), 1.5–1.3 (m, 1H), 0.92 (t, 1.2H, J=7.4 Hz), 0.80 (t, 1.5 H, J=7.4 Hz).

IR (KBr tab.) (cm$^{-1}$): 1711, 1657, 1605, 1505, 1425, 1324.

Example 96

Diastereomixture of 3-[1-(6,7-dimethoxy-4-quinazolinyl)-3-ethyl-4-piperidinyl]-1-ethyl-1,2,3,4-tetrahydro-6,8-dinitro-2,4-dioxoquinazoline
(Compound 105)

The procedure similar to that described in Example 15 was repeated, except that 132.2 mg (0.29 mmol) of 3-(1-ethoxycarbonyl-3-ethyl-4-piperidinyl)-1-ethyl-1,2,3,4-tetrahydro-6,8-dinitro-2,4-dioxoquinazoline (Compound mm; diastereomixture) was used in place of Compound a, whereby 164.9 mg of crude 1-ethyl-3-(3-ethyl-4-piperidinyl)-1,2,3,4-tetrahydro-6,8-dinitro-2,4-dioxoquinazoline hydrobromide was obtained. The product was treated in the similar manner as in Example 15 to give 75.8 mg (yield: 38%) of Compound 105 as a 7:3 diastereomixture.

$^1$H-NMR (CDCl$_3$) δ (ppm): 9.24 (d, 1H, J=2.5 Hz), 8.72 (d, 1H, J=2.5 Hz), 8.67 (s, 1H), 7.34 (s, 0.7H), 7.30 (s, 0.3H), 7.22 (s, 0.7H), 7.16 (s, 0.3H), 5.25–5.15 (m, 0.7H), 5.0–4.85 (m, 0.3H), 4.5–4.3 (m, 2H), 4.15–3.9 (m, 3H), 4.04 (s, 3H), 4.03 (s, 3H), 3.6–3.1 (m, 1.4H), 3.1–2.7 (m, 0.6H), 2.3–2.15 (m, 1H), 2.0–1.85 (m, 1H), 1.8–1.6 (m, 1H), 1.5–1.3 (m, 1H), 1.33 (t, 2.1H, J=6.9 Hz), 1.21 (t, 0.9H, J=6.9 Hz), 0.93 (t, 0.9 Hz, J=7.4 Hz), 0.80 (t, 2.1H, J=7.2 Hz).

IR (KBr tab.) (cm$^{-1}$): 1724, 1674, 1614, 1542, 1498, 1448, 1333.

Example 97
Tablets:

Tablets having the following composition were prepared in a conventional manner.

Compound 50 (100 g) obtained in Example 41, 226.8 g of lactose, and 60 g of potato starch were mixed, and 120 g of a 10% aqueous solution of hydroxypropyl cellulose was added thereto. The resulting mixture was kneaded, granulated, dried, and subjected to size reduction in a usual manner to prepare granules for tableting. The granules were mixed with 1.2 g of magnesium stearate, and the mixture was tableted by means of a tableting machine (Model RT-15 manufactured by Kikusui K.K.) having pestles of 8 mm diameter to give tablets each containing 50 mg of the active ingredient.

| Prescription: | |
| --- | --- |
| Compound 50 | 50 mg |
| Lactose | 113.4 mg |
| Potato starch | 30 mg |
| Hydroxypropyl cellulose | 6 mg |
| Magnesium stearate | 0.6 mg |
| | 200 mg |

Example 98
Tablets:

Tablets having the following composition were prepared in a conventional manner.

Compound 24 (100 g) obtained in Reference Example 6, 226.8 g of lactose, and 60 g of potato starch were mixed, and 120 g of a 10% aqueous solution of hydroxypropyl cellulose was added thereto. The resulting mixture was kneaded, granulated, dried, and subjected to size reduction in a usual manner to prepare granules for tableting. The granules were mixed with 1.2 g of magnesium stearate, and the mixture was tableted by means of a tableting machine (Model RT-15 manufactured by Kikusui K.K.) having pestles of 8 mm diameter to give tablets each containing 50 mg of the active ingredient.

| Prescription: | |
|---|---|
| Compound 24 | 50 mg |
| Lactose | 113.4 mg |
| Potato starch | 30 mg |
| Hydroxypropyl cellulose | 6 mg |
| Magnesium stearate | 0.6 mg |
| | 200 mg |

Reference Example 1

6-Amino-3-[1-(6,7-dimethoxy-4-quinazolinyl)-4-piperidinyl]-1,2,3,4-tetrahydro-2,4-dioxoquinazoline (Compound 19)

The procedure similar to that described in Example 14 was repeated, except that 450.0 mg (0.94 mmol) of Compound 24 was used in place of Compound 1. As a result, 150.0 mg (yield: 35.6%) of Compound 19 was obtained as white crystals.

$^1$H-NMR (DMSO-d$_6$) δ (ppm): 10.99 (s, 1H, NH), 8.56 (s, 1H), 7.23 (s, 1H), 7.15 (s, 1H), 7.13 (d, 1H, J=7.4 Hz), 6.93–6.89 (m, 2H), 5.40–5.05 (br.-s, 2H, NH$_2$), 5.20–5.05 (m, 1H), 4.36–4.32 (br.-d, 2H), 3.95 (s, 3H), 3.93 (s, 3H), 3.22–3.12 (br.-t, 2H), 2.95–2.82 (m, 2H), 1.75–1.71 (br.-d, 2H).

IR (KBr tab.) (cm$^{-1}$): 3430, 3356, 1711, 1655, 1509, 1351, 1216.

Melting Point (ether): 278°–280° C.

Reference Example 2

6-Acetylamino-3-[1-(6,7-dimethoxy-4-quinazolinyl)-4-piperidinyl]-1,2,3,4-tetrahydro-2,4-dioxoquinazoline (Compound 20)

In 10 ml of dichloromethane was dissolved 100 mg (0.22 mmol) of Compound 19 obtained in Reference Example 1, and 0.06 ml (0.45 mmol) of triethylamine and 0.02 ml (0.24 mmol) of acetic anhydride were added thereto, followed by stirring at room temperature for 2 hours. Water was added to the reaction mixture, and the mixture was extracted with chloroform. The organic layer was washed and dried. The solvent was distilled off, and ether was added to the residual oily substance. The precipitated crystals were collected by filtration to give 69.1 mg (yield: 64%) of Compound 20 as white crystals.

$^1$H-NMR (CDCl$_3$) δ (ppm): 9.90 (br.-s, 1H, NH), 8.66 (s, 1H), 8.03 (s, 1H), 7.97 (d, 1H, J=8.4 Hz), 7.25 (s, 1H), 7.15 (s, 1H), 6.97 (d, 1H, J=8.4 Hz), 5.35–5.25 (m, 1H), 4.40–4.35 (br.-d, 2H), 4.01 (s, 3H), 3.97 (s, 3H), 3.27–3.18 (br.-t, 2H), 3.09–3.01 (m, 2H), 2.20 (s, 3H), 1.84–1.80 (br.-d, 2H).

IR (KBr tab.) (cm$^{-1}$): 3400, 1711, 1663, 1504, 1430.

Melting Point (ether): 249°–250° C.

Reference Example 3

7-Chloro-3-[1-(6,7-dimethoxy-4-quinazolinyl)-4-piperidinyl]-1,2,3,4-tetrahydro-2,4-dioxoquinazoline (Compound 21)

The procedure similar to that described in Example 15 was repeated, except that 110.0 mg (0.31 mmol) of 7-chloro-3-(1-ethoxycarbonyl-4-piperidinyl)-1,2,3,4-tetrahydro-2,4-dioxoquinazoline (Compound e) was used in place of Compound a, whereby 86.3 mg of crude 7-chloro-1,2,3,4-tetrahydro-2,4-dioxo-3-(4-piperidinyl)quinazoline hydrobromide was obtained. The product (76.2 mg) was treated in the similar manner as in Example 15 to give 61.3 mg (yield: 48.2%) of Compound 21 as white crystals.

$^1$H-NMR (DMSO-d$_6$) δ (ppm): 11.42 (s, 1H, NH), 8.55 (s, 1H), 7.92 (d, 1H, J=8.4 Hz), 7.25–7.21 (m, 2H), 7.18 (s, 1H), 7.15 (s, 1H), 5.12–5.06 (m, 1H), 4.35–4.30 (br.-d, 2H), 3.94 (s, 3H), 3.92 (s, 3H), 3.21–3.12 (br.-t, 2H), 2.83–2.78 (m, 2H), 1.78–1.74 (br.-d, 2H).

IR (KBr tab.) (cm$^{-1}$): 1718, 1668, 1607, 1477, 1347.

Melting Point (ethyl acetate-ether): 277°–279° C.

Reference Example 4

3-[1-(6,7-Dimethoxy-4-quinazolinyl)-4-piperidinyl]-1,2,3,4-tetrahydro-6-methyl-2,4-dioxoquinazoline (Compound 22)

The procedure similar to that described in Example 15 was repeated, except that 1.0 g (3.02 mmol) of 3-(1-ethoxycarbonyl-4-piperidinyl)-1,2,3,4-tetrahydro-6-methyl-2,4-dioxoquinazoline (Compound f) was used in place of Compound a, whereby 876.3 mg of crude 6-methyl-3-(4-piperidinyl)-1,2,3,4-tetrahydro-2,4-dioxoquinazoline hydrobromide was obtained. The product (300.0 mg) was treated in the similar manner as in Example 15 to give 356.3 mg (yield: 77.6%) of Compound 22 as white crystals.

$^1$H-NMR (CDCl$_3$) δ (ppm): 8.93 (s, 1H, NH), 8.69 (s, 1H), 7.92 (s, 1H), 7.42 (d, 1H, J=8.5 Hz), 7.34 (s, 1H), 7.19 (s, 1H), 6.92 (d, 1H, J=8.5 Hz), 5.35–5.20 (m, 1H), 4.43–4.38 (br.-d, 2H), 4.04 (s, 3H), 4.00 (s, 3H), 3.29–3.19 (br.-t, 2H), 3.13–3.04 (m, 2H), 2.41 (s, 3H), 1.89–1.84 (br.-d, 2H).

IR (KBr tab.) (cm$^{-1}$): 3400, 1712, 1621, 1503, 1430.

Melting Point (DMF-water): >280° C.

Reference Example 5

8-Chloro-3-[1-(6,7-dimethoxy-4-quinazolinyl)-4-piperidinyl]-1,2,3,4-tetrahydro-6-nitro-2,4-dioxoquinazoline (Compound 23)

The procedure similar to that described in Example 15 was repeated, except that 700.0 mg (1.77 mmol) of 8-chloro-3-(1-ethoxycarbonyl-4-piperidinyl)-1,2,3,4-tetrahydro-6-nitro-2,4-dioxoquinazoline (Compound g) was used in place of Compound a, whereby 462.2 mg of crude 8-chloro-1,2,3,4-tetrahydro-6-nitro-2,4-dioxo-3-(4-piperidinyl)quinazoline hydrobromide was obtained. The product (300.0 mg) was treated in the similar manner as in Example 15 to give 330.8 mg (yield: 56.5%) of Compound 23 as pale yellow crystals.

$^1$H-NMR (CDCl$_3$-DMSO-d$_6$) δ (ppm): 8.87 (d, 1H, J=2.5 Hz), 8.64 (s, 1H), 8.50 (d, 1H, J=2.5 Hz), 7.29 (s, 1H), 7.18 (s, 1H), 5.26–5.17 (m,1H), 4.44–4.39 (br.-d, 2H), 4.04 (s, 3H), 4.01 (s, 3H), 3.28–3.19 (br.-t, 2H), 3.12–3.02 (m, 2H), 1.90–1.86 (br. -d, 2H).

IR (KBr tab.) (cm$^{-1}$): 1723, 1663, 1619, 1509, 1342.

Melting Point (ether): >280° C.

Reference Example 6

3-[1-(6,7-Dimethoxy-4-quinazolinyl)-4-piperidinyl]-1,2,3,4-tetrahydro-6-nitro-2,4-dioxoquinazoline (Compound 24)

In 150 ml of DMF was dissolved 3.0 g (8.09 mmol) of 1,2,3,4-tetrahydro-6-nitro-2,4-dioxo-3-(4-piperidinyl)-quinazoline hydrobromide, and 1.7 g (8.09 mmol) of 4-chloro-6,7-dimethoxyquinazoline and 1.1 g (24 mmol) of potassium carbonate were added to the solution, followed by heating at 80° C. for 2 hours. Water was added to the reaction mixture, and the mixture was extracted with chloroform. The organic layer was washed with an aqueous solution of sodium chloride and dried. After the solvent was distilled off, ethanol and ether were added to the residue. The precipitated crystals were collected by filtration and washed with ether to give 3.28 g (yield: 85%) of Compound 24 as white crystals.

$^1$H-NMR (DMSO-d$_6$) δ (ppm): 12.01 (s, 1H, NH), 8.67 (d, 1H, J=2.5 Hz), 8.55 (s, 1H), 8.45 (dd, 1H, J=9.0, 2.5 Hz), 7.34 (d, 1H, J=9.0 Hz), 7.23 (s, 1H), 7.15 (s, 1H), 5.09–5.04 (m, 1H), 4.37–4.32 (br.-d, 2H), 3.95 (s, 3H), 3.93 (s, 3H), 3.27–3.23 (br.-t, 2H), 2.87–2.78 (m, 2H), 1.81–1.77 (br.-d, 2H).

IR (KBr tab.) (cm$^{-1}$): 1721, 1661, 1506, 1484, 1446, 1338.

Melting Point (ether): 290°–292° C.

Reference Example 7

8-Chloro-3-(1-ethoxycarbonyl-4-piperidinyl)-1,2,3,4-tetrahydro-1-methyl-2,4-dioxoquinazoline
(Compound a)

The procedure similar to that described in Example 1 was repeated, except that 2.0 g (5.69 mmol) of 8-chloro-3-(1-ethoxycarbonyl-4-piperidinyl)-1,2,3,4-tetrahydro-2,4-dioxoquinazoline was used in place of Compound 24, whereby 890.0 mg (yield: 43%) of Compound a was obtained as a white amorphous substance.

$^1$H-NMR (CDCl$_3$) δ (ppm): 8.11 (dd, 1H, J=7.5, 1.5 Hz), 7.65 (dd, 1H, J=7.5, 1.7 Hz), 7.18 (dd, 1H, J=7.5, 7.5 Hz), 4.99–4.93 (m, 1H), 4.43–4.21 (br.-s, 2H), 4.14 (q, 2H, J=7.5 Hz), 3.80 (s, 3H), 2.95–2.85 (br.-t, 2H), 2.73–2.60 (m, 2H), 1.67–1.62 (br.-d, 2H), 1.27 (t, 3H, J=7.5 Hz).

Reference Example 8

3-(1-Ethoxycarbonyl-4-piperidinyl)-1-ethyl-1,2,3,4-tetrahydro-6-methyl-2,4-dioxoquinazoline
(Compound b)

The procedure similar to that described in Example 1 was repeated, except that 1.0 g (3.02 mmol) of 3-(1-ethoxycarbonyl-4-piperidinyl)-1,2,3,4-tetrahydro-6-methyl-2,4-dioxoquinazoline (Compound f) was used in place of Compound 24 and ethyl iodide was used in place of methyl iodide, whereby 855.0 mg (yield: 79%) of Compound b was obtained as white crystals.

$^1$H-NMR (CDCl$_3$) δ (ppm): 7.99 (d, 1H, J=1.5 Hz), 7.46 (dd, 1H, J=8.0, 1.5 Hz), 7.07 (d, 1H, J=8.0 Hz), 5.16–5.05 (m, 1H), 4.41–4.25 (br.-s, 2H), 4.18–4.10 (m, 4H), 2.96–2.63 (m, 4H), 2.40 (s, 3H), 1.66–1.62 (br.-d, 2H), 1.32 (t, 3H, J=7.9 Hz), 1.27 (t, 3H, J=7.2 Hz).

Reference Example 9

3-(1-Ethoxycarbonyl-4-piperidinyl)-1,2,3,4-tetrahydro-6-methyl-2,4-dioxo-1-propylquinazoline
(Compound c)

The procedure similar to that described in Example 1 was repeated, except that 1.0 g (3.02 mmol) of 3-(1-ethoxycarbonyl-4-piperidinyl)-1,2,3,4-tetrahydro-6-methyl-2,4-dioxoquinazoline (Compound f) was used in place of Compound 24 and propyl iodide was used in place of methyl iodide, whereby 1.09 g (yield: 97%) of Compound c was obtained as a colorless oily substance.

$^1$H-NMR (CDCl$_3$) δ (ppm): 7.99 (d, 1H, J=1.5 Hz), 7.45 (dd, 1H, J=8.0, 1.5 Hz), 7.04 (d, 1H, J=8.0 Hz), 5.16–5.07 (m, 1H), 4.46–4.25 (br.-s, 2H), 4.14 (q, 2H, J=7.0 Hz), 4.05–3.99 (dist.-t, 2H), 2.96–2.63 (m, 4H), 2.40 (s, 3H), 1.81–1.61 (m, 4H), 1.27 (t, 3H, J=7.0 Hz), 1.02 (t, 3H, J=7.3 Hz).

Reference Example 10

8-Chloro-3-(1-ethoxycarbonyl-4-piperidinyl)-1,2,3,4-tetrahydro-1-methyl-6-nitro-2,4-dioxoquinazoline
(Compound d)

The procedure similar to that described in Example 1 was repeated, except that 1.1 g (2.77 mmol) of 8-chloro-3-(1-ethoxycarbonyl-4-piperidinyl)-1,2,3,4-tetrahydro-6-nitro-2,4-dioxoquinazoline (Compound g) was used in place of Compound 24, whereby 259.8 mg (yield: 23%) of Compound d was obtained as white crystals.

$^1$H-NMR (CDCl$_3$) δ (ppm): 8.95 (d, 1H, J=3.0 Hz), 8.51 (d, 1H, J=3.0 Hz), 4.99–4.94 (m, 1H), 4.35–4.31 (m, 2H), 4.15 (q, 2H, J=7.0 Hz), 3.86 (s, 3H), 2.90–2.80 (br.-t, 2H), 2.69–2.55 (m, 2H), 1.68–1.63 (br.-d, 2H), 1.28 (t, 3H, J=7.0 Hz).

Reference Example 11

3-[1-(6,7-Dimethoxy-4-quinazolinyl)-4-piperidinyl]-1,2,3,4-tetrahydro-5-methyl-2,4-dioxoquinazoline
(Compound 100)

The procedure similar to that described in Example 15 was repeated, except that 1.00 g (3.17 mmol) of 3-(1-ethoxycarbonyl-4-piperidinyl)-1,2,3,4-tetrahydro-5-methyl-2,4-dioxoquinazoline (Compound nn) was used in place of Compound a, whereby 854.1 mg of crude 1,2,3,4-tetrahydro-5-methyl-2,4-dioxo-3-(4-piperidinyl)quinazoline hydrobromide was obtained. The product (850.0 mg) was treated in the similar manner as in Example 40 to give 1.02 g (yield: 72%) of Compound 100 as white crystals.

$^1$H-NMR (DMSO-d$_6$) δ (ppm): 11.2 (br, 1H, NH), 8.56 (s, 1H), 7.46 (dd, 1H, J=8.2, 7.5 Hz), 7.23 (s, 1H), 7.15 (s, 1H), 7.01 (d, 1H, J=8.2 Hz), 6.97 (d, 1H, J=7.5 Hz), 5.15–5.05 (m, 1H), 4.36–4.31 (br.-d, 2H), 3.94 and 3.92 (s for each, 3H), 3.18–3.12 (br.-t, 2H), 2.82–2.78 (m, 2H), 1.75–1.71 (br.-d, 2H).

IR (KBr tab.) (cm$^{-1}$): 1708, 1661, 1505, 1477, 1352.

Melting Point (methanol-water): 283°–284° C. (decomposition)

Reference Example 12

3-[1-(6,7-Dimethoxy-4-quinazolinyl)-4-piperidinyl]-1,2,3,4-tetrahydro-8-methyl-2,4-dioxoquinazoline
(Compound 101)

The procedure similar to that described in Example 15 was repeated, except that 1.00 g (3.17 mmol) of 3-(1-ethoxycarbonyl-4-piperidinyl)-1,2,3,4-tetrahydro-8-methyl-2,4-dioxoquinazoline (Compound oo) was used in place of Compound a, whereby 960.0 mg of crude 1,2,3,4-tetrahydro-8-methyl-2,4-dioxo-3-(4-piperidinyl) quinazoline hydrobromide was obtained. The product (900.0 mg) was treated in the similar manner as in Example 40 to give 1.09 g (yield: 82%) of Compound 101 as white crystals.

$^1$H-NMR (DMSO-d$_6$) δ (ppm): 11.4 (br, 1H, NH), 8.56 (s, 1H), 7.80 (d, 1H, J=8.0 Hz), 7.48 (d, 1H, J=7.0 Hz), 7.23 (s, 1H), 7.14 (s, 1H), 7.10 (dd, 1H, J=8.0, 7.0 Hz), 5.20–5.00 (m, 1H), 4.35–4.31 (br.-d, 2H), 3.96 and 3.92 (s for each, 3H), 3.22–3.13 (br.-t, 2H), 2.87–2.83 (m, 2H), 1.78–1.75 (br.-d, 2H).

IR (KBr tab.) (cm$^{-1}$): 1706, 1651, 1506, 1418.

Melting Point (methanol-water): 267°–268° C. (decomposition)

Reference Example 13

3-[1-(6,7-Dimethoxy-4-quinazolinyl)-4-piperidinyl]-1,2,3,4-tetrahydro-6-hydroxy-2,4-dioxoquinazoline (Compound 102)

The procedure similar to that described in Example 15 was repeated, except that 500.0 mg (1.44 mmol) of 3-(1-ethoxycarbonyl-4-piperidinyl)-1,2,3,4-tetrahydro-6-methoxy-2,4-dioxoquinazoline (Compound pp) was used in place of Compound a, whereby 338.6 mg of crude 1,2,3,4-tetrahydro-6-hydroxy-2,4-dioxo-3-(4-piperidinyl) quinazoline hydrobromide was obtained. The product (330.0 mg) was treated in the similar manner as in Example 40 to give 362.0 mg (yield: 57%) of Compound 102 as white crystals.

$^1$H-NMR (DMSO-d$_6$) δ (ppm): 11.1 (br, 1H, NH), 9.58 (s, 1H, OH), 8.54 (s, 1H), 7.28 (d, 1H, J=2.5 Hz), 7.22 (s, 1H), 7.15 (s, 1H), 7.10 (dd, 1H, J=9.0, 2.5 Hz), 7.02 (d, 1H, J=9.0 Hz), 5.14–5.05 (m, 1H), 4.35–4.31 (br.-d, 2H), 3.95 and 3.93 (s for each, 3H), 3.21–3.11 (br.-t, 2H), 2.91–2.79 (m, 2H), 1.75–1.71 (br.-d, 2H).

IR (KBr tab.) (cm$^{-1}$): 1703, 1662, 1506, 1482, 1433.

Melting Point (ether). 297°–298° C. (decomposition)

Reference Example 14

Diastereomixture of 3-[1-(6,7-dimethoxy-4-quinazolinyl)-3-methyl-4-piperidinyl]-1,2,3,4-tetrahydro-6-nitro-2,4-dioxoquinazoline (Compound 106)

The procedure similar to that described in Example 15 was repeated, except that 500 mg (1.33 mmol) of 3-(1-ethoxycarbonyl-3-methyl-4-piperidinyl)-1,2,3,4-tetrahydro-6-nitro-2,4-dioxoquinazoline (Compound qq; diastereomixture) was used in place of Compound a, whereby 514.3 mg of crude 1,2,3,4-tetrahydro-3-(3-methyl-4-piperidinyl)-6-nitro-2,4-dioxoquinazoline hydrobromide was obtained. The product (254.3 mg) was treated in the similar manner as in Example 15 to give 100.5 mg (yield: 31%) of Compound 106 as a 7:3 diastereomixture.

$^1$H-NMR (CDCl$_3$) δ (ppm): 8.97 (d, 1H, J=2.6 Hz), 8.68 (s, 1H), 8.38 (dd, 1H, J=9.1, 2.6 Hz), 7.31 (d, 1H, J=9.1 Hz), 7.28 (s, 1H), 7.17 (s, 1H), 5.2–5.1 (m, 0.3H), 5.0–4.7 (m, 0.7H), 4.45–4.2 (m, 1H), 4.06 (s, 3H), 4.02 (s, 0.9H), 4.01 (s, 2.1H), 3.65–3.4 (m, 1H), 3.3–3.1 (m, 2H), 3.0–2.85 (m, 1H), 2.0–1.8 (m, 1H), 1.22 (d, 0.9H, J=6.9 Hz), 0.92 (d, 2.1H, J=7.4 Hz).

IR (KBr tab.) (cm$^{-1}$): 1726, 1675, 1511, 1480, 1433, 1338.

Reference Example 15

Diastereomixture of 3-[1-(6,7-dimethoxy-4-quinazolinyl)-3-ethyl-4-piperidinyl]-1,2,3,4-tetrahydro-6-nitro-2,4-dioxoquinazoline (Compound 107)

The procedure similar to that described in Example 15 was repeated, except that 300 mg (0.77 mmol) of 3-(1-ethoxycarbonyl-3-ethyl-4-piperidinyl)-1,2,3,4-tetrahydro-6-nitro-2,4-dioxoquinazoline (Compound rr; diastereomixture) was used in place of Compound a, whereby 315 mg of crude 3-(3-ethyl-4-piperidinyl)-1,2,3,4-tetrahydro-6-nitro-2,4-dioxoquinazoline hydrobromide was obtained. The product was treated in the similar manner as in Example 15 to give 167 mg (yield: 43%) of Compound 107 as a 6:4 diastereomixture.

$^1$H-NMR (CDCl$_3$) δ (ppm): 9.03 (d, 1H, J=2.6 Hz), 8.72 (s, 0.4H), 8.70 (s, 0.6H), 8.46 (dd, 1H, J=8.9, 2.4 Hz), 7.33 (s, 1H), 7.24 (s, 0.6H), 7.22 (d, 1H, J=8.9 Hz), 7.18 (s, 0.4H), 5.35–5.2 (m, 1H), 4.5–4.3 (m, 2H), 4.03 (s, 6H), 3.6–3.4 (m, 2H), 3.4–3.25 (m, 1H), 2.25–2.15 (m, 1H), 2.05–1.9 (m, 1H), 1.8–1.55 (m, 1H), 1.55–1.35 (m, 1H), 0.92 (t, 1.2H, J=7.3 Hz), 0.78 (t, 1.8H, J=7.4 Hz).

IR (KBr tab.) (cm$^{-1}$): 1722, 1657, 1610, 1510, 1429, 1332.

Reference Example 16

3-[1-(6,7-Dimethoxy-4-quinazolinyl)-3-piperidinyl]-1,2,3,4-tetrahydro-6-nitro-2,4-dioxoquinazoline (Compound 108)

The procedure similar to that described in Example 15 was repeated, except that 184 mg (0.51 mmol) of 3-(1-ethoxycarbonyl-3-piperidinyl)-1,2,3,4-tetrahydro-6-nitro-2,4-dioxoquinazoline (Compound ss) was used in place of Compound a, whereby 173 mg of crude 1,2,3,4-tetrahydro-6-nitro-2,4-dioxo-3-(3-piperidinyl)quinazoline hydrobromide was obtained. The product was treated in the similar manner as in Example 15 to give 193 mg (yield: 80%) of Compound 108.

$^1$H-NMR (DMSO-d$_6$) δ (ppm): 12.01 (s, 1H), 8.63 (s, 1H), 8.54 (s, 1H), 8.44 (d, 1H, J=8.9 Hz), 7.32 (d, 1H, J=8.9 Hz), 7.20 (s, 1H), 7.15 (s, 1H), 5.25–5.05 (m, 1H), 4.2–4.05 (m, 2H), 4.05–3.9 (m, 1H), 3.93 (s, 6H), 3.1–2.9 (m, 1H), 2.75–2.55 (m, 1H), 2.0–1.8 (m, 3H).

IR (KBr tab.) (cm$^{-1}$): 1724, 1667, 1610, 1503, 1481, 1429, 1333.

Industrial Applicability

According to the present invention, there is provided a drug containing a 1,2,3,4-tetrahydro-2,4-dioxoquinazoline derivative or a pharmaceutically acceptable salt thereof as an active ingredient, which has an adenosine uptake inhibitory activity and is useful for the protection of myocardium and for the prevention or suppression of inflammation such as leg and foot edema.

We claim:

1. An adenosine uptake inhibitor containing a 1,2,3,4-tetrahydro-2,4-dioxoquinazoline derivative represented by formula (I):

wherein R$^1$ represents hydrogen, substituted or unsubstituted lower alkyl, alkenyl, or substituted or unsubstituted aralkyl; R$^2$, R$^3$, R$^4$, and R$^5$ independently represent hydrogen, halogen, amino, mono- or di(lower alkyl)amino, lower alkanoylamino, nitro, cyano, substituted or unsubstituted lower alkyl, hydroxy, lower alkoxy, lower alkylthio, carboxy, lower alkoxycarbonyl, lower alkanoyl, aralkyloxy, or lower alkanoyloxy; R$^6$, R$^7$, R$^8$, and R$^9$ independently represent hydrogen, hydroxy, substituted or unsubstituted lower alkoxy, or aralkyloxy, or any adjoining two of them are combined to form methylenedioxy; $R^{10}$ represents hydrogen or lower alkyl; and Y and Z independently represent C—$R^{11}$ (wherein $R^{11}$ represents hydrogen, substituted or unsubstituted lower alkyl, or halogen),
or a pharmaceutically acceptable salt thereof as an active ingredient.

2. An adenosine uptake inhibitor according to claim 1, wherein $R^1$ represents hydrogen, substituted or unsubstituted lower alkyl, allyl, or substituted or unsubstituted aralkyl; $R^2$, $R^3$, $R^4$, and $R^5$ independently represent hydrogen, halogen, amino, mono- or di(lower alkyl)amino, lower alkanoylamino, nitro, cyano, substituted or unsubstituted lower alkyl, hydroxy, lower alkoxy, lower alkoxycarbonyl, aralkyloxy, or lower alkanoyloxy; $R^6$ and $R^9$ each represents hydrogen; $R^7$ and $R^8$ independently represent hydroxy or lower alkoxy; $R^{10}$ represents hydrogen; Y represents CH; and the 3-position of the 2,4-dioxoquinazoline ring and the 4-position of the piperidine ring are directly connected.

3. A 1,2,3,4-tetrahydro-2,4-dioxoquinazoline derivative represented by formula (I-a):

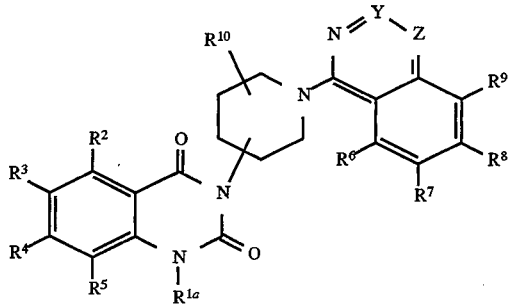

wherein $R^{1a}$ represents substituted or unsubstituted lower alkyl, alkenyl, or substituted or unsubstituted aralkyl; and $R^2$, $R^3$, $R^4$, $R^5$, $R^6$, $R^7$, $R^8$, $R^9$, $R^{10}$, Y, and Z have the same meanings as defined in claim 1,
or a pharmaceutically acceptable salt thereof.

4. A 1,2,3,4-tetrahydro-2,4-dioxoquinazoline derivative according to claim 3 wherein $R^{1a}$ represents substituted or unsubstituted lower alkyl, allyl, or substituted or unsubstituted aralkyl; $R^2$, $R^3$, $R^4$, and $R^5$ independently represent hydrogen, halogen, amino, mono- or di(lower alkyl)amino, lower alkanoylamino, nitro, cyano, substituted or unsubstituted lower alkyl, hydroxy, lower alkoxy, lower alkoxycarbonyl, aralkyloxy, or lower alkanoyloxy; $R^6$ and $R^9$ each represents hydrogen; $R^7$ and $R^8$ independently represent hydroxy or lower alkoxy; $R^{10}$ represents hydrogen; Y represents CH; and the 3-position of the 2,4-dioxoquinazoline ring and the 4-position of the piperidine ring are directly connected, or a pharmaceutically acceptable salt thereof.

5. A 1,2,3,4-tetrahydro-2,4-dioxoquinazoline derivative according to claim 4 wherein $R^7$ and $R^8$ each represents methoxy, or a pharmaceutically acceptable salt thereof.

6. A 1,2,3,4-tetrahydro-2,4-dioxoquinazoline derivative according to claim 5 wherein $R^{1a}$ represents substituted or unsubstituted lower alkyl, or a pharmaceutically acceptable salt thereof.

7. A 1,2,3,4-tetrahydro-2,4-dioxoquinazoline derivative according to claim 6 wherein $R^2$, $R^3$, $R^4$, and $R^5$ independently represent hydrogen or substituted or unsubstituted lower alkyl, or a pharmaceutically acceptable salt thereof.

8. A 1,2,3,4-tetrahydro-2,4-dioxoquinazoline derivative according to claim 7 wherein $R^{1a}$ and $R^3$ each represents methyl, and $R^2$, $R^4$, and $R^5$ each represents hydrogen, or a pharmaceutically acceptable salt thereof.

* * * * *

UNITED STATES PATENT AND TRADEMARK OFFICE
CERTIFICATE OF CORRECTION

PATENT NO. : 5,658,917

DATED : August 19, 1997

INVENTOR(S) : SHIGEKI FUJIWARA, ET AL

It is certified that error appears in the above-identified patent and that said Letters Patent is hereby corrected as shown below:

TITLE PAGE AT [30]
   Foreign Application Priority Data, add
      --Feb. 16, 1994 [PCT] PCT ................ JP94/00229--.

COLUMN 20
   Line 20, "($cm^1$" should read --($cm^{-1}$)--.

COLUMN 35
   Line 3, "(m, 14H)" should read --(m, 4H)--.

COLUMN 51
   Line 65, "(t, 1.5H" should read -- (t, 1.8H--.

Signed and Sealed this

Tenth Day of March, 1998

*Attest:*

BRUCE LEHMAN

*Attesting Officer*  Commissioner of Patents and Trademarks